US009937171B2

(12) United States Patent
Izumi et al.

(10) Patent No.: US 9,937,171 B2
(45) Date of Patent: Apr. 10, 2018

(54) METHODS OF BLOCKING THE CXCR-4/SDF-1 SIGNALING PATHWAY WITH INHIBITORS OF BRUTON'S TYROSINE KINASE

(71) Applicant: Acerta Pharma B.V., Oss (NL)

(72) Inventors: Raquel Izumi, San Carlos, CA (US); Francisco Salva, San Francisco, CA (US); Ahmed Hamdy, Santa Cruz, CA (US)

(73) Assignee: ACERTA PHARMA B.V., Oss (NL)

( * ) Notice: Subject to any disclaimer, the term of this patent is extended or adjusted under 35 U.S.C. 154(b) by 0 days.

(21) Appl. No.: 15/303,502

(22) PCT Filed: Apr. 10, 2015

(86) PCT No.: PCT/IB2015/001418
§ 371 (c)(1),
(2) Date: Oct. 11, 2016

(87) PCT Pub. No.: WO2015/181633
PCT Pub. Date: Dec. 3, 2015

(65) Prior Publication Data
US 2017/0035756 A1 Feb. 9, 2017

Related U.S. Application Data

(60) Provisional application No. 61/978,759, filed on Apr. 11, 2014.

(51) Int. Cl.
A61K 31/4985 (2006.01)
A61K 31/454 (2006.01)
(Continued)

(52) U.S. Cl.
CPC ........ A61K 31/4985 (2013.01); A61K 31/454 (2013.01); A61K 31/519 (2013.01); A61K 31/52 (2013.01)

(58) Field of Classification Search
None
See application file for complete search history.

(56) References Cited

U.S. PATENT DOCUMENTS 7,459,554 B2   12/2008   Dong et al.
7,825,118 B2   11/2010   Honigberg et al.
(Continued)

FOREIGN PATENT DOCUMENTS

EP    2548877       1/2013
WO    2001019828    3/2001
(Continued)

OTHER PUBLICATIONS

Chen et al., BioMed Research International vol. 2014 (2014), Article ID 814869, 1-6.*
(Continued)

Primary Examiner — Karl J Puttlitz
(74) Attorney, Agent, or Firm — Morgan Lewis & Bockius LLP

(57) ABSTRACT

In some embodiments, the present invention relates to novel small molecule inhibitors that block the CXCR4-SDF-1 signaling pathway by directly inhibiting members of the Tec family of kinases, namely Bruton's tyrosine kinase (BTK), and their use in treating diseases in which pathogenesis is mediated by the CXCR4/SDF-1 signaling pathway.

17 Claims, 9 Drawing Sheets

(51) Int. Cl.
  A61K 31/519      (2006.01)
  A61K 31/52       (2006.01)

(56) References Cited

U.S. PATENT DOCUMENTS

| | | |
|---|---|---|
| 7,960,396 B2 | 6/2011 | Honigberg et al. |
| 8,377,946 B1 | 2/2013 | Chen et al. |
| 8,658,794 B2 | 2/2014 | deMan et al. |
| 9,290,504 B2 | 3/2016 | Barf et al. |
| 2006/0084654 A1 | 4/2006 | Beck et al. |
| 2008/0076921 A1 | 3/2008 | Honigberg et al. |
| 2009/0181987 A1* | 7/2009 | Honigberg ............ A61K 31/00 514/262.1 |
| 2011/0257203 A1 | 10/2011 | Honigberg et al. |
| 2012/0053189 A1 | 3/2012 | Loury |
| 2012/0095026 A1 | 4/2012 | Honigberg et al. |
| 2012/0129821 A1 | 5/2012 | Honigberg et al. |
| 2012/0135944 A1 | 5/2012 | Honigberg et al. |
| 2012/0165328 A1 | 6/2012 | Honigberg et al. |
| 2013/0018032 A1 | 1/2013 | Chen et al. |
| 2013/0079327 A1 | 3/2013 | Yamamoto et al. |
| 2013/0217880 A1 | 8/2013 | Yamamoto et al. |
| 2014/0073593 A1 | 3/2014 | Conklin et al. |
| 2014/0206681 A1 | 7/2014 | Kim et al. |
| 2014/0212425 A1 | 7/2014 | Chang et al. |

FOREIGN PATENT DOCUMENTS

| | | |
|---|---|---|
| WO | 2007064993 | 6/2001 |
| WO | 2002080926 | 10/2002 |
| WO | 2003065995 | 8/2003 |
| WO | 2005037836 | 4/2005 |
| WO | 2005097800 | 10/2005 |
| WO | 2007061737 | 5/2007 |
| WO | 2007064883 | 6/2007 |
| WO | 2007106503 | 9/2007 |
| WO | 2008121742 | 10/2008 |
| WO | 2009076170 | 6/2009 |
| WO | 2010126960 | 11/2010 |
| WO | 2011095556 | 8/2011 |
| WO | 2011119663 | 9/2011 |
| WO | 2011152351 | 12/2011 |
| WO | 2011153514 | 12/2011 |
| WO | 2012158843 | 11/2012 |
| WO | 2013003629 | 1/2013 |
| WO | 2013010380 | 1/2013 |
| WO | 2013010868 A1 | 1/2013 |
| WO | 2013010869 | 1/2013 |
| WO | 2013059738 | 4/2013 |
| WO | 2014143807 | 9/2014 |
| WO | 2014159745 | 10/2014 |
| WO | 2014168975 | 10/2014 |
| WO | 2015018522 | 2/2015 |

OTHER PUBLICATIONS

Bam et al., "Bruton's Tyrosine Kinase (BTK) is Indispensable for Myeloma Cell Migration towards SDF-1 and Induction of Osteoclastogenesis and Osteolytic Bone Disease", Blood, vol. 116, p. 447 (2010).
Bam et al., "Role of Bruton's tyrosine kinase in myeloma cell migration and induction of bone disease", Am. J. Hematol., vol. 88, pp. 463-471 (2013).
Cao et al., "CXCR4 WHIM-like frameshift and nonsense mutations promote ibrutinib resistance but do not supplant MYD88L265P-directed survival signalling in Waldenstrom macroglobulinaemia cells", British Journal of Haematology, vol. 168, pp. 701-707 (2015).
Written Opinion for PCT/IB2015/001418.
International Search Report for PCT/IB2015/001418 dated Dec. 16, 2015.
Berge et al. "Pharmaceutical salts" 66(1) J. Pharm. Sci. 1-19 (1977).
Bingham et al., "Over one hundred solvates of sulfathlazole" Chem. Commun. 603-04 (2001).
Caira et al., "Preparation and Crystal Characterization of a Polymorph, a Monohydrate, and an Ethyl Acetate Solvate of the Antifungal Fluconazole," 93(3) J. Pharma. Sci. 601-11 (2004).
Davis et al., "Chronic active B-cell-receptor signaling in diffuse large B-cell lymphoma," 463 Nature 88-92 (2010).
Dhar et al., "Synthesis and SAR of p38a MAP kinase inhibitors based on heterobicyclic scaffolds," 17 Bioorg. & Med. Chem. Lett. 5019-24 (2007).
Gaudet et al., "A Homogeneous Fluorescence Polarization Assay Adaptable for a Range of Protein Serine/Threonine and Tyrosine Kinases," 8(2) J. Biomol. Screening 164-75 (2003).
Gilfillan et al., "The tyrosine kinase network regulating mast cell activation," 288 Immun. Rev. 149-69 (2009).
Gould "Salt selection for basic drugs" 33 Int'l J. Pharmaceutics 201-217 (1986).
Harder et al., "Gain- and Loss-of-Function Lyn Mutant Mice Define a Critical Inhibitory Role for Lyn in the Myeloid Lineage" 15 immunity 603-15 (2001).
Hartz et al., "Synthesis and Evaluation of imidazo[1,5-a]pyrazines as Corticotrophin Releasing Hormone Receptor Ligands," 12 Bioorg. & Med. Chem. Lett. 291-94 (2002).
Ji et al., "A novel, potent, and selective insulin-like growth factor-I receptor kinase inhibitor blocks insulin-like growth factor-I receptor signaling in vitro and inhibits insulin-like growth factor-Ireceptor-dependent tumor growth in vivo," 6(8) Mol. Cancer Ther. 2158-67 (2007).
King et al., "Nucleofugality effects in the pyridine promoted formation of esters from 2-substituted ethanesulfonyl chlorides," 66 Can. J. Chem. 1109-16 (1988).
Klinghoffer et al., "Src family kinases are required for integrin but not PDGFR signal transduction," 18(9) EMBO J. 2459-71 (1999).
Lim et al., "Anti-CD20 monoclonal antibodies: historical and future perspectives," 95(1) Haematologica 135-43 (2010).
Lowell et al., "Deficiency of the Hck and Src Tyrosine Kinases Results in Extreme Levels of Extramedullary Hematopoiesis," 87(5) Blood 1780-92 (1996).
Mitchell et al., "Synthesis of C-nucleoside isosteres of 9-(2-hydroxyethoxymethyl)guanine (acyclovir)," 21 (3) J. Heterocyclic Chem. 697-99 (1984).
Mukaiyama et al., "Synthesis and c-Src inhibitory activity of imidazo[1,5-a]pyrazine derivatives as an agent for treatment of acute ischemic stroke," 15 Bioorg. & Med. Chem. 868-85 (2007).
Mulvihill et al., "1,3-Disubstituted-imidazo[1,5-a]pyrazines as insulin-like growth-factor-I receptor (IGF-IR) inhibitors", 17 Bioorg. & Med. Chem. Lett. 1091-97 (2007).
Mulvihill et al., "Novel 2-phenylquinolin-7-yl-derived imidazo[1,5-a]pyrazines as potent insulin-growth factor-I receptor (IGF-IR) inhibitors", 16 Bioorg. & Med. Chem. 1359-75 (2008).
Odom et al., "Negative Regulation of immunoglobulin E-dependent Allergic Responses by Lyn Kinase," 199(11) J. Exp. Med. 1491-1502 (2004).
Pan et al., "Discovery of Selective Irreversible Inhibitors for Bruton's Tyrosine Kinase," 2 ChemMedChem 58-61 (2007).
Roby et al., "Alterations in Reproductive Function in Src Tyrosine Kinase Knockout Mice", 26 Endocrine 169-76 (2005).
Shinohara et al., "Tyrosine Kinases Btk and Tec Regulate Osteoclast Differentiation by Linking RANK and ITAM Signals" 132 Cell 794-806 (2008).
van Tonder et al., "Preparation and Physicochemical Characterization of 5 Niclosamide Solvates and 1 Hemisolvate", 5(1) AAPS PharmSciTech Article 12 (2004).
Written Opinion dated Aug. 10, 2016 relating to PCT/IB2016/053988.
International Search Report dated Aug. 10, 2016 relating to PCT/IB2016/053988.

* cited by examiner

METHODS OF BLOCKING THE CXCR-4/SDF-1 SIGNALING PATHWAY WITH INHIBITORS OF BRUTON'S TYROSINE KINASE

FIELD OF THE INVENTION

In some embodiments, the present invention relates to novel small molecule inhibitors that block the CXCR4-SDF-1 signaling pathway by directly inhibiting members of the Tec family of kinases, namely Bruton's tyrosine kinase (BTK), and their use in treating diseases in which pathogenesis is mediated by the CXCR4/SDF-1 signaling pathway.

BACKGROUND OF THE INVENTION

CXCR4, a G-protein-coupled receptor, and its naturally occurring ligand, stromal cell-derived factor-1 (SDF-1; CXCL12), are a chemokine receptor-ligand pair. CXCR4 is constitutively or over-expressed in a wide variety of human cancers (Table 1). SDF-1, the only known ligand of CXCR4, is highly expressed in tumor microenvironments, as well as in bone marrow, lung, liver, and lymph nodes, i.e., organ sites most commonly involved in tumor metastasis. CXCR4/SDF-1 interaction plays important roles in multiple stages of tumorigenesis, including tumor growth, invasion, angiogenesis, and metastasis (Furusato, et al., *Pathology International* 2010, 60, 497-505). The CXCR4/SDF1 axis also serves a role in attraction multiple leukocyte subsets and stimulation B cell production and myelopoeisis, all of which are implicated in autoimmune diseases (Chong and Mohan, *Expert Opin. Ther. Targets* 2009, 13(10), 1147-1153). In view of the involvement of CXCR4/SDF-1 in these serious diseases, the CXCR4/SDF-1 pathway may be an attractive therapeutic target (Tamamura and Fujii, *Expert Opin. Ther. Targets* 2005, 9(6), 1267-1282).

TABLE 1

| CXCR4+ Expressing Tumors. |
| --- |
| Leukemias |
| Brian tumors |
| Small cell lung cancer |
| Breast cancer |
| Prostate cancer |
| Rhabdomyosarcoma |
| Neuroblastoma |
| Wilms' tumor |
| Hepatoblastoma |
| Ovarian cancer |
| Cervical cancer |
| Osteosarcoma |

Sources: Kucia, et al., *Stem Cells* 2005, 23, 879-894; Furusato, et al. 2010, 60, 497-505; Retz, et al., *Int. J. Cancer* 2005, 114, 182-189.

Tec kinases represent the second largest family of non-receptor tyrosine kinases and are activated in response to cellular stimulation by antigen receptors, integrins, growth factors, cytokines and G protein-coupled receptors (Qiu and Kung, *Oncogene* 2000, 19, 5651-5661). The mammalian Tec family consists of five members: Tec, BTK, Itk/Emt/Tsk, Rlk/Txk, and BMX/ETK (Mano, *Cytokine Growth Factor Rev.*, 1999, 10, 267-280). With some exceptions, Tec kinases are expressed primarily in cells of hematopoietic lineages.

BTK (Bruton's Tyrosine Kinase) is a Tec family non-receptor protein kinase expressed in B cells and myeloid cells. BTK is composed of the pleckstrin homology (PH), Tec homology (TH), Src homology 3 (SH3), Src homology 2 (SH2), and tyrosine kinase or Src homology 1 (TK or SH1) domains. Each of these domains has the potential to interact with a plethora of proteins critical for intracellular signaling. Moreover, functional association of BTK with many of its partners is crucial for its activation and regulation. BTK is a metalloprotein enzyme requiring $Zn^{2+}$ for optimal activity and stability (Mohammed, *Immunol. Rev.* 2009, 228, 58-73). The function of BTK in signaling pathways activated by the engagement of the B cell receptor (BCR) in mature B cells and FCER1 on mast cells is well established. Functional mutations in BTK in humans result in a primary immunodeficiency disease (X-linked agammaglobuinaemia) characterized by a defect in B cell development with a block between pro- and pre-B cell stages. The result is an almost complete absence of B lymphocytes, causing a pronounced reduction of serum immunoglobulin of all classes. These findings support a key role for BTK in the regulation of the production of auto-antibodies in autoimmune diseases.

BTK is expressed in numerous B cell lymphomas and leukemias. Other diseases with an important role for dysfunctional B cells are B cell malignancies, as described in Hendriks, et al., *Nat. Rev. Cancer*, 2014, 14, 219-231. The reported role for BTK in the regulation of proliferation and apoptosis of B cells indicates the potential for BTK inhibitors in the treatment of B cell lymphomas. BTK inhibitors have thus been developed as potential therapies for many of these malignancies, as described in D'Cruz, et al., *Onco-Targets and Therapy* 2013, 6, 161-176.

BTK is expressed in most hematopoietic cells except T cells and in osteoclasts but not in osteoblasts. The PH-TH domain of BTK has been shown to bind to $\beta\gamma$, $G\alpha q$ and $G\alpha 12$ subunits of heterotrimeric G-proteins and the association results in elevation of kinase activity. Thus BTK plays an important role in G protein signaling, including signaling downstream of CXCR4 (de Gorter, et al., *Immunity* 2007, 26, 93-104; Ortolano, et al., *Eur. J. Immunol.* 2006, 36, 1285-1295) and makes an attractive target for inhibition of CXCR4 signaling.

SUMMARY OF THE INVENTION

Disclosed herein is the discovery that some BTK inhibitors surprisingly block the CXCR4/SDF-1 signaling pathway. Accordingly, provided herein are methods of blocking the CXCR4/SDF-1 signaling in a subject in need thereof comprising administering to the subject a BTK inhibitor in an amount effective to block said CXCR4/SDF-1 signaling pathway. These methods may be used in the treatment of disorders associated with overexpression of CXCR4 or dysregulation of CXCR4 signaling, e.g., autoimmune disorders or hematologic or nonhematologic malignancies.

In an embodiment, the invention provides a BTK inhibitor capable of blocking the CXCR4/SDF-1 signaling pathway.

In another aspect, the present invention provides a pharmaceutical composition, comprising a BTK inhibitor or pharmaceutically acceptable salt thereof as variously described above, and a pharmaceutically acceptable carrier, diluent, or excipient.

In another aspect, the present invention provides a BTK inhibitor or pharmaceutically acceptable salt thereof as variously described above, for use in therapy.

In another aspect, the present invention provides a BTK inhibitor or pharmaceutically acceptable salt thereof as variously described above, for the treatment of autoimmune disorders or hematologic or nonhematologic malignancies.

In another aspect, the present invention provides the use of a BTK inhibitor or pharmaceutically acceptable salt thereof as variously described above, for the manufacture of a medicament for the treatment of autoimmune disorders or hematologic or nonhematologic malignancies.

In another aspect, the present invention provides a method of treating autoimmune disorders or hematologic or nonhematologic malignancies comprising administering to a patient in need thereof an effective amount of a BTK inhibitor or pharmaceutically acceptable salt thereof as variously described above.

BRIEF DESCRIPTION OF THE DRAWINGS

The foregoing summary, as well as the following detailed description of the invention, will be better understood when read in conjunction with the appended drawings.

DETAILED DESCRIPTION OF THE INVENTION

Figure 1:
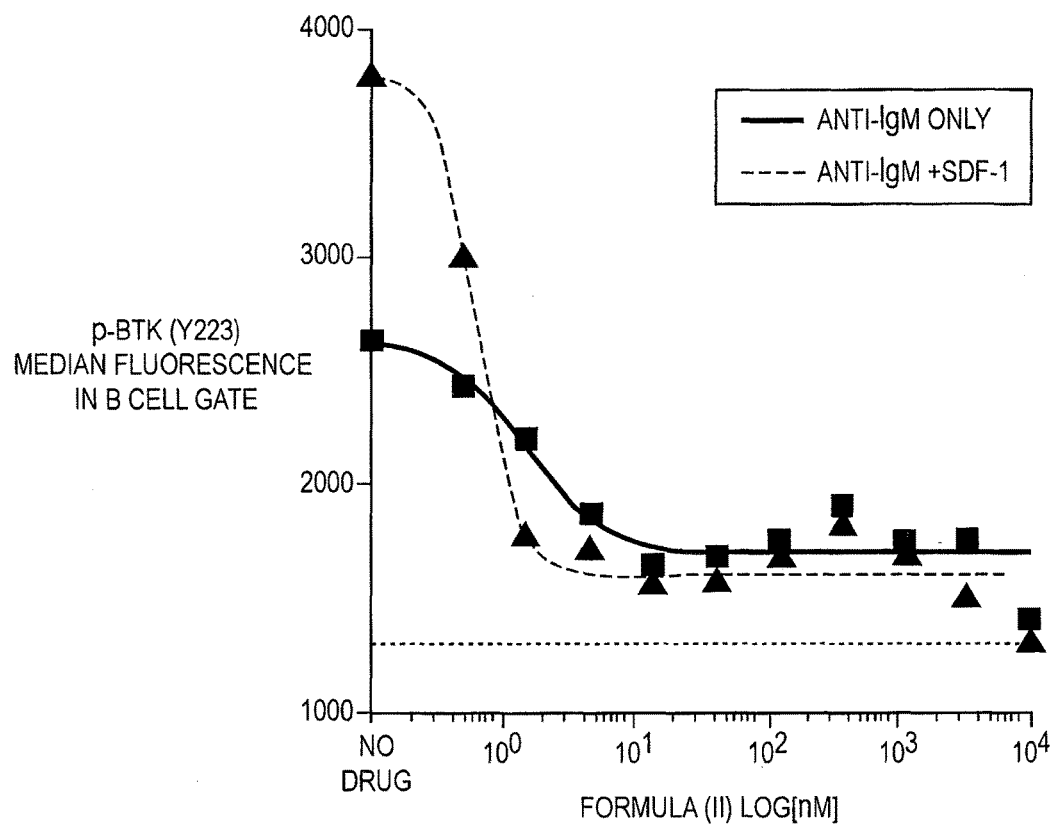
FIG. 1 illustrates $CD20^+$ B cell fluorescence, showing that CXCR-4/SDF-1 signaling is inhibited by the BTK inhibitor of Formula (II).

While preferred embodiments of the invention are shown and described herein, such embodiments are provided by way of example only and are not intended to otherwise limit the scope of the invention. Various alternatives to the described embodiments of the invention may be employed in practicing the invention.

Unless defined otherwise, all technical and scientific terms used herein have the same meaning as is commonly understood by one of skill in the art to which this invention belongs. All patents and publications referred to herein are incorporated by reference in their entireties.

The term "SDF-1" includes two isoforms, SDF-1α and SDF-1β, currently understood to exhibit similar functionality, which are also called CXCL12.

"Treatment" as used herein refers to curative treatment of disorders associated CXCR4 receptor activity. Curative treatment refers to processes involving a slowing, interrupting, arresting, controlling, or stopping of disease progression, but does not necessarily involve a total elimination of all disease-related symptoms, conditions, or disorders.

The terms "co-administration," "co-administering," "administered in combination with," and "administering in combination with" as used herein, encompass administration of two or more agents to a subject so that both agents and/or their metabolites are present in the subject at the same time. Co-administration includes simultaneous administration in separate compositions, administration at different times in separate compositions, or administration in a composition in which two or more agents are present.

The term "effective amount" or "therapeutically effective amount" refers to that amount of a compound or combination of compounds as described herein that is sufficient to effect the intended application including, but not limited to, disease treatment. A therapeutically effective amount may vary depending upon the intended application (in vitro or in vivo), or the subject and disease condition being treated (e.g., the weight, age and gender of the subject), the severity of the disease condition, the manner of administration, etc. which can readily be determined by one of ordinary skill in the art. The term also applies to a dose that will induce a particular response in target cells, (e.g., the reduction of platelet adhesion and/or cell migration). The specific dose will vary depending on the particular compounds chosen, the dosing regimen to be followed, whether the compound is administered in combination with other compounds, timing of administration, the tissue to which it is administered, and the physical delivery system in which the compound is carried.

A "therapeutic effect" as that term is used herein, encompasses a therapeutic benefit and/or a prophylactic benefit as described above. A prophylactic effect includes delaying or eliminating the appearance of a disease or condition, delaying or eliminating the onset of symptoms of a disease or condition, slowing, halting, or reversing the progression of a disease or condition, or any combination thereof.

The term "pharmaceutically acceptable salt" refers to salts derived from a variety of organic and inorganic counter ions known in the art. Pharmaceutically acceptable acid addition salts can be formed with inorganic acids and organic acids. Inorganic acids from which salts can be derived include, for example, hydrochloric acid, hydrobromic acid, sulfuric acid, nitric acid and phosphoric acid. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid and salicylic acid. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese and aluminum. Organic bases from which salts can be derived include, for example, primary, secondary, and tertiary amines, substituted amines including naturally occurring substituted amines, cyclic amines and basic ion exchange resins. Specific examples include isopropylamine, trimethylamine, diethylamine, triethylamine, tripropylamine, and ethanolamine. In selected embodiments, the pharmaceutically acceptable base addition salt is chosen from ammonium, potassium, sodium, calcium, and magnesium salts. The term "cocrystal" refers to a molecular complex derived from a number of cocrystal formers known in the art. Unlike a salt, a cocrystal typically does not involve hydrogen transfer between the cocrystal and the drug, and instead involves intermolecular interactions, such as hydrogen bonding, aromatic ring stacking, or dispersive forces, between the cocrystal former and the drug in the crystal structure.

"Pharmaceutically acceptable carrier" or "pharmaceutically acceptable excipient" is intended to include any and all solvents, dispersion media, coatings, antibacterial and antifungal agents, isotonic and absorption delaying agents. The use of such media and agents for pharmaceutically active substances is well known in the art. Except insofar as any conventional media or agent is incompatible with the active ingredient, its use in the therapeutic compositions of the invention is contemplated. Supplementary active ingredients can also be incorporated into the described compositions.

"Prodrug" is intended to describe a compound that may be converted under physiological conditions or by solvolysis to a biologically active compound described herein. Thus, the term "prodrug" refers to a precursor of a biologically active compound that is pharmaceutically acceptable. A prodrug may be inactive when administered to a subject, but is converted in vivo to an active compound, for example, by hydrolysis. The prodrug compound often offers the advantages of solubility, tissue compatibility or delayed release in a mammalian organism (see, e.g., Bundgaard, H., Design of Prodrugs, Elsevier, Amsterdam, 1985). The term "prodrug" is also intended to include any covalently bonded carriers, which release the active compound in vivo when administered to a subject. Prodrugs of an active compound, as described herein, may be prepared by modifying functional groups present in the active compound in such a way that the modifications are cleaved, either in routine manipulation or in vivo, to yield the active parent compound. Prodrugs include, for example, compounds wherein a hydroxy, amino or mercapto group is bonded to any group that, when the prodrug of the active compound is administered to a mammalian subject, cleaves to form a free hydroxy, free amino or free mercapto group, respectively. Examples of prodrugs include, but are not limited to, acetates, formates and benzoate derivatives of an alcohol, various ester derivatives of a carboxylic acid, or acetamide, formamide and benzamide derivatives of an amine functional group in the active compound.

The term "in vivo" refers to an event that takes place in a subject's body.

The term "in vitro" refers to an event that takes places outside of a subject's body. In vitro assays encompass cell-based assays in which cells alive or dead are employed and may also encompass a cell-free assay in which no intact cells are employed.

The terms "QD," "qd," or "q.d." mean quaque die, once a day, or once daily. The terms "BID," "bid," or "b.i.d." mean bis in die, twice a day, or twice daily. The terms "TID," "tid," or "t.i.d." mean ter in die, three times a day, or three times daily. The terms "QID," "qid," or "q.i.d." mean quater in die, four times a day, or four times daily.

Unless otherwise stated, the chemical structures depicted herein are intended to include compounds which differ only in the presence of one or more isotopically enriched atoms. For example, compounds where one or more hydrogen atoms is replaced by deuterium or tritium, or wherein one or more carbon atoms is replaced by $^{13}$C- or $^{14}$C-enriched carbons, are within the scope of this invention.

When ranges are used herein to describe, for example, physical or chemical properties such as molecular weight or chemical formulae, all combinations and subcombinations of ranges and specific embodiments therein are intended to be included. Use of the term "about" when referring to a number or a numerical range means that the number or numerical range referred to is an approximation within experimental variability (or within statistical experimental error), and thus the number or numerical range may vary from, for example, between 1% and 15% of the stated number or numerical range. The term "comprising" (and related terms such as "comprise" or "comprises" or "having" or "including") includes those embodiments such as, for example, an embodiment of any composition of matter, method or process that "consist of" or "consist essentially of" the described features.

"Alkyl" refers to a straight or branched hydrocarbon chain radical consisting solely of carbon and hydrogen atoms, containing no unsaturation, having from one to ten carbon atoms (e.g., ($C_{1-10}$)alkyl or $C_{1-10}$ alkyl). Whenever it appears herein, a numerical range such as "1 to 10" refers to each integer in the given range—e.g., "1 to 10 carbon atoms" means that the alkyl group may consist of 1 carbon atom, 2 carbon atoms, 3 carbon atoms, etc., up to and including 10 carbon atoms, although the definition is also intended to cover the occurrence of the term "alkyl" where no numerical range is specifically designated. Typical alkyl groups include, but are in no way limited to, methyl, ethyl, propyl, isopropyl, n-butyl, iso-butyl, sec-butyl isobutyl, tertiary butyl, pentyl, isopentyl, neopentyl, hexyl, heptyl, octyl, nonyl and decyl. The alkyl moiety may be attached to the rest of the molecule by a single bond, such as for example, methyl (Me), ethyl (Et), n-propyl (Pr), 1-methylethyl (isopropyl), n-butyl, n-pentyl, 1,1-dimethylethyl (t-butyl) and 3-methylhexyl. Unless stated otherwise specifically in the specification, an alkyl group is optionally substituted by one or more of substituents which are independently alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(N-R$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$ where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Alkylaryl" refers to an -(alkyl)aryl radical where aryl and alkyl are as disclosed herein and which are optionally substituted by one or more of the substituents described as suitable substituents for aryl and alkyl respectively.

"Alkylhetaryl" refers to an -(alkyl)hetaryl radical where hetaryl and alkyl are as disclosed herein and which are optionally substituted by one or more of the substituents described as suitable substituents for aryl and alkyl respectively.

"Alkylheterocycloalkyl" refers to an -(alkyl) heterocycyl radical where alkyl and heterocycloalkyl are as disclosed herein and which are optionally substituted by one or more of the substituents described as suitable substituents for heterocycloalkyl and alkyl respectively.

An "alkene" moiety refers to a group consisting of at least two carbon atoms and at least one carbon-carbon double bond, and an "alkyne" moiety refers to a group consisting of at least two carbon atoms and at least one carbon-carbon triple bond. The alkyl moiety, whether saturated or unsaturated, may be branched, straight chain, or cyclic.

"Alkenyl" refers to a straight or branched hydrocarbon chain radical group consisting solely of carbon and hydrogen atoms, containing at least one double bond, and having from two to ten carbon atoms (i.e., ($C_{2-10}$)alkenyl or $C_{2-10}$ alkenyl). Whenever it appears herein, a numerical range such as "2 to 10" refers to each integer in the given range—e.g., "2 to 10 carbon atoms" means that the alkenyl group may consist of 2 carbon atoms, 3 carbon atoms, etc., up to and including 10 carbon atoms. The alkenyl moiety may be attached to the rest of the molecule by a single bond, such as for example, ethenyl (i.e., vinyl), prop-1-enyl (i.e., allyl), but-1-enyl, pent-1-enyl and penta-1,4-dienyl. Unless stated otherwise specifically in the specification, an alkenyl group is optionally substituted by one or more substituents which are independently alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Alkenyl-cycloalkyl" refers to an -(alkenyl)cycloalkyl radical where alkenyl and cyclo alkyl are as disclosed herein and which are optionally substituted by one or more of the substituents described as suitable substituents for alkenyl and cycloalkyl respectively.

"Alkynyl" refers to a straight or branched hydrocarbon chain radical group consisting solely of carbon and hydrogen atoms, containing at least one triple bond, having from two to ten carbon atoms (i.e., (C$_{2-10}$)alkynyl or C$_{2-10}$ alkynyl). Whenever it appears herein, a numerical range such as "2 to 10" refers to each integer in the given range—e.g., "2 to 10 carbon atoms" means that the alkynyl group may consist of 2 carbon atoms, 3 carbon atoms, etc., up to and including 10 carbon atoms. The alkynyl may be attached to the rest of the molecule by a single bond, for example, ethynyl, propynyl, butynyl, pentynyl and hexynyl. Unless stated otherwise specifically in the specification, an alkynyl group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Alkynyl-cycloalkyl" refers to an -(alkynyl)cycloalkyl radical where alkynyl and cycloalkyl are as disclosed herein and which are optionally substituted by one or more of the substituents described as suitable substituents for alkynyl and cycloalkyl respectively.

"Carboxaldehyde" refers to a —(C═O)H radical.

"Carboxyl" refers to a —(C═O)OH radical.

"Cyano" refers to a —CN radical.

"Cycloalkyl" refers to a monocyclic or polycyclic radical that contains only carbon and hydrogen, and may be saturated, or partially unsaturated. Cycloalkyl groups include groups having from 3 to 10 ring atoms (i.e. (C$_{3-10}$)cycloalkyl or C$_{3-10}$ cycloalkyl). Whenever it appears herein, a numerical range such as "3 to 10" refers to each integer in the given range—e.g., "3 to 10 carbon atoms" means that the cycloalkyl group may consist of 3 carbon atoms, etc., up to and including 10 carbon atoms. Illustrative examples of cycloalkyl groups include, but are not limited to the following moieties: cyclopropyl, cyclobutyl, cyclopentyl, cyclopentenyl, cyclohexyl, cyclohexenyl, cycloheptyl, cyclooctyl, cyclononyl, cyclodecyl, norbornyl, and the like. Unless stated otherwise specifically in the specification, a cycloalkyl group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)R$^a$, —OC(O)N(R$^a$)$_2$, —C(O)N(R$^a$)$_2$, —N(R$^a$)C(O)R$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Cycloalkyl-alkenyl" refers to a -(cycloalkyl)alkenyl radical where cycloalkyl and alkenyl are as disclosed herein and which are optionally substituted by one or more of the substituents described as suitable substituents for cycloalkyl and alkenyl, respectively.

"Cycloalkyl-heterocycloalkyl" refers to a -(cycloalkyl)heterocycloalkyl radical where cycloalkyl and heterocycloalkyl are as disclosed herein and which are optionally substituted by one or more of the substituents described as suitable substituents for cycloalkyl and heterocycloalkyl, respectively.

"Cycloalkyl-heteroaryl" refers to a -(cycloalkyl)heteroaryl radical where cycloalkyl and heteroaryl are as disclosed herein and which are optionally substituted by one or more of the substituents described as suitable substituents for cycloalkyl and heteroaryl, respectively.

The term "alkoxy" refers to the group —O-alkyl, including from 1 to 8 carbon atoms of a straight, branched, cyclic configuration and combinations thereof attached to the parent structure through an oxygen. Examples include, but are not limited to, methoxy, ethoxy, propoxy, isopropoxy, cyclopropyloxy and cyclohexyloxy. "Lower alkoxy" refers to alkoxy groups containing one to six carbons.

The term "substituted alkoxy" refers to alkoxy wherein the alkyl constituent is substituted (i.e., —O-(substituted alkyl)). Unless stated otherwise specifically in the specification, the alkyl moiety of an alkoxy group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

The term "alkoxycarbonyl" refers to a group of the formula (alkoxy)(C═O)— attached through the carbonyl carbon wherein the alkoxy group has the indicated number of carbon atoms. Thus a (C$_{1-6}$)alkoxycarbonyl group is an alkoxy group having from 1 to 6 carbon atoms attached through its oxygen to a carbonyl linker. "Lower alkoxycarbonyl" refers to an alkoxycarbonyl group wherein the alkoxy group is a lower alkoxy group.

The term "substituted alkoxycarbonyl" refers to the group (substituted alkyl)-O—C(O)— wherein the group is attached to the parent structure through the carbonyl functionality. Unless stated otherwise specifically in the specification, the alkyl moiety of an alkoxycarbonyl group is optionally substituted by one or more substituents which independently are: alkyl, heteroalkyl, alkenyl, alkynyl, cycloalkyl, heterocycloalkyl, aryl, aryl alkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Acyl" refers to the groups (alkyl)-C(O)—, (aryl)-C(O)—, (heteroaryl)-C(O)—, (heteroalkyl)-C(O)— and (heterocycloalkyl)-C(O)—, wherein the group is attached to the parent structure through the carbonyl functionality. If the R radical is heteroaryl or heterocycloalkyl, the hetero ring or chain atoms contribute to the total number of chain or ring atoms. Unless stated otherwise specifically in the specification, the alkyl, aryl or heteroaryl moiety of the acyl group is optionally substituted by one or more substituents which are independently alkyl, heteroalkyl, alkenyl, alkynyl, cycloalkyl, heterocycloalkyl, aryl, aryl alkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Acyloxy" refers to a R(C=O)O— radical wherein "R" is alkyl, aryl, heteroaryl, heteroalkyl or heterocycloalkyl, which are as described herein. If the R radical is heteroaryl or heterocycloalkyl, the hetero ring or chain atoms contribute to the total number of chain or ring atoms. Unless stated otherwise specifically in the specification, the "R" of an acyloxy group is optionally substituted by one or more substituents which independently are: alkyl, heteroalkyl, alkenyl, alkynyl, cycloalkyl, heterocycloalkyl, aryl, aryl alkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Amino" or "amine" refers to a —N(R$^a$)$_2$ radical group, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl, unless stated otherwise specifically in the specification. When a —N(R$^a$)$_2$ group has two R$^a$ substituents other than hydrogen, they can be combined with the nitrogen atom to form a 4-, 5-, 6- or 7-membered ring. For example, —N(R$^a$)$_2$ is intended to include, but is not limited to, 1-pyrrolidinyl and 4-morpholinyl. Unless stated otherwise specifically in the specification, an amino group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

The term "substituted amino" also refers to N-oxides of the groups —NHR$^d$, and NR$^d$R$^d$ each as described above. N-oxides can be prepared by treatment of the corresponding amino group with, for example, hydrogen peroxide or m-chloroperoxybenzoic acid.

"Amide" or "amido" refers to a chemical moiety with formula —C(O)N(R)$_2$ or —NHC(O)R, where R is selected from the group consisting of hydrogen, alkyl, cycloalkyl, aryl, heteroaryl (bonded through a ring carbon) and heteroalicyclic (bonded through a ring carbon), each of which moiety may itself be optionally substituted. The R$_2$ of —N(R)$_2$ of the amide may optionally be taken together with the nitrogen to which it is attached to form a 4-, 5-, 6- or 7-membered ring. Unless stated otherwise specifically in the specification, an amido group is optionally substituted independently by one or more of the substituents as described herein for alkyl, cycloalkyl, aryl, heteroaryl, or heterocycloalkyl. An amide may be an amino acid or a peptide molecule attached to a compound disclosed herein, thereby forming a prodrug. The procedures and specific groups to make such amides are known to those of skill in the art and can readily be found in seminal sources such as Greene and Wuts, Protective Groups in Organic Synthesis, 3$^{rd}$ Ed., John Wiley & Sons, New York, 1999, which is incorporated herein by reference in its entirety.

"Aromatic" or "aryl" or "Ar" refers to an aromatic radical with six to ten ring atoms (e.g., C$_6$-C$_{10}$ aromatic or C$_6$-C$_{10}$ aryl) which has at least one ring having a conjugated pi electron system which is carbocyclic (e.g., phenyl, fluorenyl, and naphthyl). Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Whenever it appears herein, a numerical range such as "6 to 10" refers to each integer in the given range; e.g., "6 to 10 ring atoms" means that the aryl group may consist of 6 ring atoms, 7 ring atoms, etc., up to and including 10 ring atoms. The term includes monocyclic or fused-ring polycyclic (i.e., rings which share adjacent pairs of ring atoms) groups. Unless stated otherwise specifically in the specification, an aryl moiety is optionally substituted by one or more substituents which are independently alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroaryl alkyl.

"Aralkyl" or "arylalkyl" refers to an (aryl)alkyl-radical where aryl and alkyl are as disclosed herein and which are optionally substituted by one or more of the substituents described as suitable substituents for aryl and alkyl respectively.

"Ester" refers to a chemical radical of formula —COOR, where R is selected from the group consisting of alkyl, cycloalkyl, aryl, heteroaryl (bonded through a ring carbon) and heteroalicyclic (bonded through a ring carbon). The procedures and specific groups to make esters are known to those of skill in the art and can readily be found in seminal sources such as Greene and Wuts, Protective Groups in Organic Synthesis, 3$^{rd}$ Ed., John Wiley & Sons, New York, N.Y., 1999, which is incorporated herein by reference in its entirety. Unless stated otherwise specifically in the specification, an ester group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(N-R$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Fluoroalkyl" refers to an alkyl radical, as defined above, that is substituted by one or more fluoro radicals, as defined above, for example, trifluoromethyl, difluoromethyl, 2,2,2-trifluoroethyl, 1-fluoromethyl-2-fluoroethyl, and the like. The alkyl part of the fluoroalkyl radical may be optionally substituted as defined above for an alkyl group.

"Halo", "halide", or, alternatively, "halogen" is intended to mean fluoro, chloro, bromo or iodo. The terms "haloalkyl," "haloalkenyl," "haloalkynyl" and "haloalkoxy" include alkyl, alkenyl, alkynyl and alkoxy structures that are substituted with one or more halo groups or with combinations thereof. For example, the terms "fluoroalkyl" and "fluoroalkoxy" include haloalkyl and haloalkoxy groups, respectively, in which the halo is fluorine.

"Heteroalkyl", "heteroalkenyl" and "heteroalkynyl" include optionally substituted alkyl, alkenyl and alkynyl radicals and which have one or more skeletal chain atoms selected from an atom other than carbon, e.g., oxygen, nitrogen, sulfur, phosphorus or combinations thereof. A numerical range may be given—e.g., C$_1$-C$_4$ heteroalkyl which refers to the chain length in total, which in this example is 4 atoms long. A heteroalkyl group may be substituted with one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, nitro, oxo, thioxo, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(N-R$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclyl alkyl, aryl, aralkyl, heterocycloalkyl, heterocycloalkylalkyl, heteroaryl or heteroarylalkyl.

"Heteroalkylaryl" refers to an -(heteroalkyl)aryl radical where heteroalkyl and aryl are as disclosed herein and which are optionally substituted by one or more of the substituents described as suitable substituents for heteroalkyl and aryl, respectively.

"Heteroalkylheteroaryl" refers to an -(heteroalkyl)heteroaryl radical where heteroalkyl and heteroaryl are as disclosed herein and which are optionally substituted by one or more of the substituents described as suitable substituents for heteroalkyl and heteroaryl, respectively.

"Heteroalkylheterocycloalkyl" refers to an -(heteroalkyl)heterocycloalkyl radical where heteroalkyl and heterocycloalkyl are as disclosed herein and which are optionally substituted by one or more of the substituents described as suitable substituents for heteroalkyl and heterocycloalkyl, respectively.

"Heteroalkylcycloalkyl" refers to an -(heteroalkyl)cycloalkyl radical where heteroalkyl and cycloalkyl are as disclosed herein and which are optionally substituted by one or more of the substituents described as suitable substituents for heteroalkyl and cycloalkyl, respectively.

"Heteroaryl" or "heteroaromatic" or "HetAr" refers to a 5- to 18-membered aromatic radical (e.g., C$_5$-C$_{13}$ heteroaryl) that includes one or more ring heteroatoms selected from nitrogen, oxygen and sulfur, and which may be a monocyclic, bicyclic, tricyclic or tetracyclic ring system. Whenever it appears herein, a numerical range such as "5 to 18" refers to each integer in the given range—e.g., "5 to 18 ring atoms" means that the heteroaryl group may consist of 5 ring atoms, 6 ring atoms, etc., up to and including 18 ring atoms. Bivalent radicals derived from univalent heteroaryl radicals whose names end in "-yl" by removal of one hydrogen atom from the atom with the free valence are named by adding "-idene" to the name of the corresponding univalent radical—e.g., a pyridyl group with two points of attachment is a pyridylidene. A N-containing "heteroaromatic" or "heteroaryl" moiety refers to an aromatic group in which at least one of the skeletal atoms of the ring is a nitrogen atom. The polycyclic heteroaryl group may be fused or non-fused. The heteroatom(s) in the heteroaryl radical are optionally oxidized. One or more nitrogen atoms, if present, are optionally quaternized. The heteroaryl may be attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzoxazolyl, benzopyranyl, benzopyranonyl, benzofuranyl, benzofuranonyl, benzofurazanyl, benzothiazolyl, benzothienyl(benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furazanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyranyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, thiapyranyl, triazolyl, tetrazolyl, triazinyl, thieno[2,3-d]pyrimidinyl, thieno[3,2-d]pyrimidinyl, thieno[2,3-c]pyridinyl, and thiophenyl (i.e. thienyl). Unless stated otherwise specifically in the specification, a heteroaryl moiety is optionally substituted by one or more substituents which are independently: alkyl, heteroalkyl, alkenyl, alkynyl, cycloalkyl, heterocycloalkyl, aryl, arylalkyl, heteroaryl, heteroarylalkyl, hydroxy, halo, cyano, nitro, oxo, thioxo, trimethylsilanyl, —$OR^a$, —$SR^a$, —OC(O)—$R^a$, —$N(R^a)_2$, —C(O)$R^a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, N($R^a$)C(N$R^a$)N($R^a$)$_2$, —N($R^a$)S(O)$_t$$R^a$ (where t is 1 or 2), —S(O)$_t$$R^a$ (where t is 1 or 2), —S(O)$_t$N($R^a$)$_2$ (where t is 1 or 2), or PO$_3$($R^a$)$_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

Substituted heteroaryl also includes ring systems substituted with one or more oxide (—O—) substituents, such as, for example, pyridinyl N-oxides.

"Heteroarylalkyl" refers to a moiety having an aryl moiety, as described herein, connected to an alkylene moiety, as described herein, wherein the connection to the remainder of the molecule is through the alkylene group.

"Heterocycloalkyl" refers to a stable 3- to 18-membered non-aromatic ring radical that comprises two to twelve carbon atoms and from one to six heteroatoms selected from nitrogen, oxygen and sulfur. Whenever it appears herein, a numerical range such as "3 to 18" refers to each integer in the given range—e.g., "3 to 18 ring atoms" means that the heterocycloalkyl group may consist of 3 ring atoms, 4 ring atoms, etc., up to and including 18 ring atoms. Unless stated otherwise specifically in the specification, the heterocycloalkyl radical is a monocyclic, bicyclic, tricyclic or tetracyclic ring system, which may include fused or bridged ring systems. The heteroatoms in the heterocycloalkyl radical may be optionally oxidized. One or more nitrogen atoms, if present, are optionally quaternized. The heterocycloalkyl radical is partially or fully saturated. The heterocycloalkyl may be attached to the rest of the molecule through any atom of the ring(s). Examples of such heterocycloalkyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, a heterocycloalkyl moiety is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, nitro, oxo, thioxo, trimethylsilanyl, —$OR^a$, —$SR^a$, —OC(O)—$R^a$, —$N(R^a)_2$, —C(O)$R^a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, N($R^a$)C(N$R^a$)N($R^a$)$_2$, —N($R^a$)S(O)$_t$$R^a$ (where t is 1 or 2), —S(O)$_t$O$R^a$ (where t is 1 or 2), —S(O)$_t$N($R^a$)$_2$ (where t is 1 or 2), or PO$_3$($R^a$)$_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Heterocycloalkyl" also includes bicyclic ring systems wherein one non-aromatic ring, usually with 3 to 7 ring atoms, contains at least 2 carbon atoms in addition to 1-3 heteroatoms independently selected from oxygen, sulfur, and nitrogen, as well as combinations comprising at least one of the foregoing heteroatoms; and the other ring, usually with 3 to 7 ring atoms, optionally contains 1-3 heteroatoms independently selected from oxygen, sulfur, and nitrogen and is not aromatic.

"Nitro" refers to the —NO$_2$ radical.

"Oxa" refers to the —O— radical.

"Oxo" refers to the =O radical.

"Isomers" are different compounds that have the same molecular formula. "Stereoisomers" are isomers that differ only in the way the atoms are arranged in space—i.e., having a different stereochemical configuration. "Enantiomers" are a pair of stereoisomers that are non-superimposable mirror images of each other. A 1:1 mixture of a pair of enantiomers is a "racemic" mixture. The term "(±)" is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon can be specified by either (R) or (S). Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and can thus give rise to enantiomers, diastereomers, and other stereoisomeric forms that can be defined, in terms of absolute stereochemistry, as (R) or (S). The present chemical entities, pharmaceutical compositions and methods are meant to include all such possible isomers, including racemic mixtures, optically pure forms and intermediate mixtures. Optically active (R)- and (S)-isomers can be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers.

"Enantiomeric purity" as used herein refers to the relative amounts, expressed as a percentage, of the presence of a specific enantiomer relative to the other enantiomer. For example, if a compound, which may potentially have an (R)- or an (S)-isomeric configuration, is present as a racemic mixture, the enantiomeric purity is about 50% with respect to either the (R)- or (S)-isomer. If that compound has one isomeric form predominant over the other, for example, 80% (S)-isomer and 20% (R)-isomer, the enantiomeric purity of the compound with respect to the (S)-isomeric form is 80%. The enantiomeric purity of a compound can be determined in a number of ways known in the art, including but not limited to chromatography using a chiral support, polarimetric measurement of the rotation of polarized light, nuclear magnetic resonance spectroscopy using chiral shift reagents which include but are not limited to lanthanide containing chiral complexes or Pirkle's reagents, or derivatization of a compounds using a chiral compound such as Mosher's acid followed by chromatography or nuclear magnetic resonance spectroscopy.

In preferred embodiments, the enantiomerically enriched composition has a higher potency with respect to therapeutic utility per unit mass than does the racemic mixture of that composition. Enantiomers can be isolated from mixtures by methods known to those skilled in the art, including chiral high pressure liquid chromatography (HPLC) and the formation and crystallization of chiral salts; or preferred enantiomers can be prepared by asymmetric syntheses. See, for example, Jacques, et al., Enantiomers, Racemates and Resolutions, Wiley Interscience, New York, 1981; Eliel, Stereochemistry of Carbon Compounds, McGraw-Hill, NY, 1962; and Eliel and Wilen, Stereochemistry of Organic Compounds, Wiley-Interscience, New York, 1994.

The terms "enantiomerically enriched" and "non-racemic," as used herein, refer to compositions in which the percent by weight of one enantiomer is greater than the amount of that one enantiomer in a control mixture of the racemic composition (e.g., greater than 1:1 by weight). For example, an enantiomerically enriched preparation of the (S)-enantiomer, means a preparation of the compound having greater than 50% by weight of the (S)-enantiomer relative to the (R)-enantiomer, such as at least 75% by weight, or such as at least 80% by weight. In some embodiments, the enrichment can be significantly greater than 80% by weight, providing a "substantially enantiomerically enriched" or a "substantially non-racemic" preparation, which refers to preparations of compositions which have at least 85% by weight of one enantiomer relative to other enantiomer, such as at least 90% by weight, or such as at least 95% by weight. The terms "enantiomerically pure" or "substantially enantiomerically pure" refers to a composition that comprises at least 98% of a single enantiomer and less than 2% of the opposite enantiomer.

"Moiety" refers to a specific segment or functional group of a molecule. Chemical moieties are often recognized chemical entities embedded in or appended to a molecule.

"Tautomers" are structurally distinct isomers that interconvert by tautomerization. "Tautomerization" is a form of isomerization and includes prototropic or proton-shift tautomerization, which is considered a subset of acid-base chemistry. "Prototropic tautomerization" or "proton-shift tautomerization" involves the migration of a proton accompanied by changes in bond order, often the interchange of a single bond with an adjacent double bond. Where tautomerization is possible (e.g. in solution), a chemical equilibrium of tautomers can be reached. An example of tautomerization is keto-enol tautomerization. A specific example of keto-enol tautomerization is the interconversion of pentane-2,4-dione and 4-hydroxypent-3-en-2-one tautomers. Another example of tautomerization is phenol-keto tautomerization. A specific example of phenol-keto tautomerization is the interconversion of pyridin-4-ol and pyridin-4(1H)-one tautomers.

A "leaving group or atom" is any group or atom that will, under selected reaction conditions, cleave from the starting material, thus promoting reaction at a specified site. Examples of such groups, unless otherwise specified, include halogen atoms and mesyloxy, p-nitrobenzenesulphonyloxy and tosyloxy groups.

"Protecting group" is intended to mean a group that selectively blocks one or more reactive sites in a multifunctional compound such that a chemical reaction can be carried out selectively on another unprotected reactive site and the group can then be readily removed or deprotected after the selective reaction is complete. A variety of protecting groups are disclosed, for example, in T. H. Greene and P. G. M. Wuts, Protective Groups in Organic Synthesis, Third Edition, John Wiley & Sons, New York (1999).

"Solvate" refers to a compound in physical association with one or more molecules of a pharmaceutically acceptable solvent.

"Substituted" means that the referenced group may have attached one or more additional groups, radicals or moieties individually and independently selected from, for example, acyl, alkyl, alkylaryl, cycloalkyl, aralkyl, aryl, carbohydrate, carbonate, heteroaryl, heterocycloalkyl, hydroxy, alkoxy, aryloxy, mercapto, alkylthio, arylthio, cyano, halo, carbonyl, ester, thiocarbonyl, isocyanato, thiocyanato, isothiocyanato, nitro, oxo, perhaloalkyl, perfluoroalkyl, phosphate, silyl, sulfinyl, sulfonyl, sulfonamidyl, sulfoxyl, sulfonate, urea, and amino, including mono- and di-substituted amino groups, and protected derivatives thereof. The substituents themselves may be substituted, for example, a cycloalkyl substituent may itself have a halide substituent at one or more of its ring carbons. The term "optionally substituted" means optional substitution with the specified groups, radicals or moieties.

"Sulfanyl" refers to groups that include —S-(optionally substituted alkyl), —S-(optionally substituted aryl), —S-(optionally substituted heteroaryl) and —S-(optionally substituted heterocycloalkyl).

"Sulfinyl" refers to groups that include —S(O)—H, —S(O)-(optionally substituted alkyl), —S(O)-(optionally substituted amino), —S(O)-(optionally substituted aryl), —S(O)-(optionally substituted heteroaryl) and —S(O)-(optionally substituted heterocycloalkyl).

"Sulfonyl" refers to groups that include —S($O_2$)—H, —S($O_2$)-(optionally substituted alkyl), —S($O_2$)-(optionally substituted amino), —S($O_2$)-(optionally substituted aryl), —S($O_2$)-(optionally substituted heteroaryl), and —S($O_2$)-(optionally substituted heterocycloalkyl).

"Sulfonamidyl" or "sulfonamido" refers to a —S($=O$)$_2$—NRR radical, where each R is selected independently from the group consisting of hydrogen, alkyl, cycloalkyl, aryl, heteroaryl (bonded through a ring carbon) and heteroalicyclic (bonded through a ring carbon). The R groups in —NRR of the —S($=O$)$_2$—NRR radical may be taken together with the nitrogen to which it is attached to form a 4-, 5-, 6- or 7-membered ring. A sulfonamido group is optionally substituted by one or more of the substituents described for alkyl, cycloalkyl, aryl, heteroaryl, respectively.

"Sulfoxyl" refers to a —S($=O$)$_2$OH radical.

"Sulfonate" refers to a —S($=O$)$_2$—OR radical, where R is selected from the group consisting of alkyl, cycloalkyl, aryl, heteroaryl (bonded through a ring carbon) and heteroalicyclic (bonded through a ring carbon). A sulfonate group is optionally substituted on R by one or more of the substituents described for alkyl, cycloalkyl, aryl, heteroaryl, respectively.

Compounds of the invention also include crystalline and amorphous forms of those compounds, including, for example, polymorphs, pseudopolymorphs, solvates, hydrates, unsolvated polymorphs (including anhydrates), conformational polymorphs, and amorphous forms of the compounds, as well as mixtures thereof. "Crystalline form" and "polymorph" are intended to include all crystalline and amorphous forms of the compound, including, for example, polymorphs, pseudopolymorphs, solvates, hydrates, unsolvated polymorphs (including anhydrates), conformational polymorphs, and amorphous forms, as well as mixtures thereof, unless a particular crystalline or amorphous form is referred to.

BTK Inhibitors

Inhibitors of BTK kinase activity include compounds which inhibits BTK activity with an IC$_{50}$ of less than or equal to 10 micromolar, less than or equal to 1 micromolar, less than or equal to 500 nanomolar, less than or equal to 100 nanomolar, or less than or equal to 10 nanomolar in an ADP-GLO™, bioluminescent, homogeneous assay or in a HTRF (Homogeneous Time-Resolved Fluorescence) assay.

Inhibitors of BTK kinase activity may inhibit phosphorylation of Y551 of BTK with an IC$_{50}$ of less than or equal to 10 micromolar, less than or equal to 1 micromolar, less than or equal to 500 nanomolar, less than or equal to 100 nanomolar, or less than or equal to 10 nanomolar.

Inhibitors of BTK kinase activity may inhibit phosphorylation of Y223 of BTK with an IC$_{50}$ of less than or equal to 10 micromolar, less than or equal to 1 micromolar, less than or equal to 500 nanomolar, less than or equal to 100 nanomolar, or less than or equal to 10 nanomolar.

Inhibitors of BTK kinase activity may inhibit phosphorylation of downstream PLCγ2 with an IC$_{50}$ of less than or equal to 10 micromolar, less than or equal to 1 micromolar, less than or equal to 500 nanomolar, less than or equal to 100 nanomolar, or less than or equal to 10 nanomolar in, e.g., a phospho-PLCγ2 assay.

Nonlimiting examples of BTK inhibitors are described in, e.g., U.S. Pat. Nos. 8,088,781; 7,989,465; 7,393,848; 7,405,295; 7,718,662; 7,960,396, and U.S. Patent Publication No. 2007/0293499, the disclosures of which are incorporated herein by reference in their entirety.

In an embodiment, the BTK inhibitor is a compound of Formula (I):

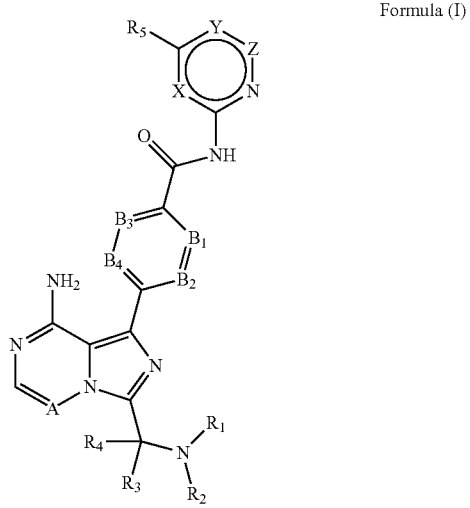

Formula (I)

or a pharmaceutically acceptable salt, solvate, hydrate, cocrystal, or prodrug thereof, wherein:

X is CH, N, O or S;
Y is C(R$_6$), N, O or S;
Z is CH, N or bond;
A is CH or N;
B$_1$ is N or C(R$_7$);
B$_2$ is N or C(R$_8$);
B$_3$ is N or C(R$_9$);
B$_4$ is N or C(R$_{10}$);

R$_1$ is R$_{11}$C(═O), R$_{12}$S(═O), R$_{13}$S(═O)$_2$ or (C$_{1-6}$)alkyl optionally substituted with R$_{14}$;
R$_2$ is H, (C$_{1-3}$)alkyl or (C$_{3-7}$)cycloalkyl;
R$_3$ is H, (C$_{1-6}$)alkyl or (C$_{3-7}$)cycloalkyl); or
R$_2$ and R$_3$ form, together with the N and C atom they are attached to, a (C$_{3-7}$)heterocycloalkyl optionally substituted with one or more fluorine, hydroxyl, (C$_{1-3}$)alkyl, (C$_{1-3}$)alkoxy or oxo;
R$_4$ is H or (C$_{1-3}$)alkyl;
R$_5$ is H, halogen, cyano, (C$_{1-4}$)alkyl, (C$_{1-3}$)alkoxy, (C$_{3-6}$)cycloalkyl, any alkyl group of which is optionally substituted with one or more halogen; or R$_5$ is (C$_{6-10}$)aryl or (C$_{2-6}$)heterocycloalkyl;
R$_6$ is H or (C$_{1-3}$)alkyl; or
R$_5$ and R$_6$ together may form a (C$_{3-7}$)cycloalkenyl or (C$_{2-6}$)heterocycloalkenyl, each optionally substituted with (C$_{1-3}$)alkyl or one or more halogens;
R$_7$ is H, halogen, CF$_3$, (C$_{1-3}$)alkyl or (C$_{1-3}$)alkoxy;
R$_8$ is H, halogen, CF$_3$, (C$_{1-3}$)alkyl or (C$_{1-3}$)alkoxy; or
R$_7$ and R$_8$ together with the carbon atoms they are attached to, form (C$_{6-10}$)aryl or (C$_{1-9}$)heteroaryl;
R$_9$ is H, halogen, (C$_{1-3}$)alkyl or (C$_{1-3}$)alkoxy;
R$_{10}$ is H, halogen, (C$_{1-3}$)alkyl or (C$_{1-3}$)alkoxy;
R$_{11}$ is independently selected from the group consisting of (C$_{1-6}$)alkyl, (C$_{2-6}$)alkenyl and (C$_{2-6}$)alkynyl, where each alkyl, alkenyl or alkynyl is optionally substituted with one or more substituents selected from the group consisting of hydroxyl, (C$_{1-4}$)alkyl, (C$_{3-7}$)cycloalkyl, [(C$_{1-4}$)alkyl]amino, di[(C$_{1-4}$)alkyl]amino, (C$_{1-3}$)alkoxy, (C$_{3-7}$)cycloalkoxy, (C$_{6-10}$)aryl and (C$_{3-7}$)heterocycloalkyl; or R$_{11}$ is (C$_{1-3}$)alkyl-C(O)—S—(C$_{1-3}$)alkyl; or
R$_{11}$ is (C$_{1-5}$)heteroaryl optionally substituted with one or more substituents selected from the group consisting of halogen or cyano;
R$_{12}$ and R$_{13}$ are independently selected from the group consisting of (C$_{2-6}$)alkenyl or (C$_{2-6}$)alkynyl, both optionally substituted with one or more substituents selected from the group consisting of hydroxyl, (C$_{1-4}$)alkyl, (C$_{3-7}$)cycloalkyl, [(C$_{1-4}$)alkyl]amino, di[(C$_{1-4}$)alkyl]amino, (C$_{1-3}$)alkoxy, (C$_{3-7}$)cycloalkoxy, (C$_{6-10}$)aryl and (C$_{3-7}$)heterocycloalkyl; or a (C$_{1-5}$)heteroaryl optionally substituted with one or more substituents selected from the group consisting of halogen and cyano; and
R$_{14}$ is independently selected from the group consisting of halogen, cyano, (C$_{2-6}$)alkenyl and (C$_{2-6}$)alkynyl, both optionally substituted with one or more substituents selected from the group consisting of hydroxyl, (C$_{1-4}$)alkyl, (C$_{3-7}$)cycloalkyl, (C$_{1-4}$)alkylamino, di[(C$_{1-4}$)alkyl]amino, (C$_{1-3}$)alkoxy, (C$_{3-7}$)cycloalkoxy, (C$_{6-10}$)aryl, (C$_{1-5}$)heteroaryl and (C$_{3-7}$)heterocycloalkyl;

with the proviso that:
0 to 2 atoms of X, Y, Z can simultaneously be a heteroatom;
when one atom selected from X, Y is O or S, then Z is a bond and the other atom selected from X, Y cannot be O or S;
when Z is C or N then Y is C(R$_6$) or N and X is C or N;
0 to 2 atoms of B$_1$, B$_2$, B$_3$ and B$_4$ are N;

with the terms used having the following meanings:
(C$_{1-2}$)alkyl means an alkyl group having 1 to 2 carbon atoms, being methyl or ethyl,
(C$_{1-3}$)alkyl means a branched or unbranched alkyl group having 1-3 carbon atoms, being methyl, ethyl, propyl or isopropyl;
(C$_{1-4}$)alkyl means a branched or unbranched alkyl group having 1-4 carbon atoms, being methyl, ethyl, propyl, isopropyl, butyl, isobutyl, sec-butyl and tert-butyl, (C$_{1-3}$) alkyl groups being preferred;

$(C_{1-5})$alkyl means a branched or unbranched alkyl group having 1-5 carbon atoms, for example methyl, ethyl, propyl, isopropyl, butyl, isobutyl, sec-butyl, tert-butyl, pentyl and isopentyl, $(C_{1-4})$alkyl groups being preferred.

$(C_{1-6})$Alkyl means a branched or unbranched alkyl group having 1-6 carbon atoms, for example methyl, ethyl, propyl, isopropyl, butyl, tert-butyl, n-pentyl and n-hexyl. $(C_{1-5})$alkyl groups are preferred, $(C_{1-4})$alkyl being most preferred;

$(C_{1-2})$alkoxy means an alkoxy group having 1-2 carbon atoms, the alkyl moiety having the same meaning as previously defined;

$(C_{1-3})$alkoxy means an alkoxy group having 1-3 carbon atoms, the alkyl moiety having the same meaning as previously defined. $(C_{1-2})$alkoxy groups are preferred;

$(C_{1-4})$alkoxy means an alkoxy group having 1-4 carbon atoms, the alkyl moiety having the same meaning as previously defined. $(C_{1-3})$alkoxy groups are preferred, $(C_{1-2})$alkoxy groups being most preferred;

$(C_{2-4})$alkenyl means a branched or unbranched alkenyl group having 2-4 carbon atoms, such as ethenyl, 2-propenyl, isobutenyl or 2-butenyl;

$(C_{2-6})$alkenyl means a branched or unbranched alkenyl group having 2-6 carbon atoms, such as ethenyl, 2-butenyl, and n-pentenyl, $(C_{2-4})$alkenyl groups being most preferred;

$(C_{2-4})$alkynyl means a branched or unbranched alkynyl group having 2-4 carbon atoms, such as ethynyl, 2-propynyl or 2-butynyl;

$(C_{2-6})$alkynyl means a branched or unbranched alkynyl group having 2-6 carbon atoms, such as ethynyl, propynyl, n-butynyl, n-pentynyl, isopentynyl, isohexynyl or n-hexynyl. $(C_{2-4})$alkynyl groups are preferred; $(C_{3-6})$cycloalkyl means a cycloalkyl group having 3-6 carbon atoms, being cyclopropyl, cyclobutyl, cyclopentyl or cyclohexyl;

$(C_{3-7})$cycloalkyl means a cycloalkyl group having 3-7 carbon atoms, being cyclopropyl, cyclobutyl, cyclopentyl, cyclohexyl or cycloheptyl;

$(C_{2-6})$heterocycloalkyl means a heterocycloalkyl group having 2-6 carbon atoms, preferably 3-5 carbon atoms, and one or two heteroatoms selected from N, O and/or S, which may be attached via a heteroatom if feasible, or a carbon atom; preferred heteroatoms are N or O; also preferred are piperidine, morpholine, pyrrolidine and piperazine; with the most preferred $(C_{2-6})$heterocycloalkyl being pyrrolidine; the heterocycloalkyl group may be attached via a heteroatom if feasible;

$(C_{3-7})$heterocycloalkyl means a heterocycloalkyl group having 3-7 carbon atoms, preferably 3-5 carbon atoms, and one or two heteroatoms selected from N, O and/or S. Preferred heteroatoms are N or O; preferred $(C_{3-7})$ heterocycloalkyl groups are azetidinyl, pyrrolidinyl, piperidinyl, homopiperidinyl or morpholinyl; more preferred $(C_{3-7})$heterocycloalkyl groups are piperidine, morpholine and pyrrolidine; and the heterocycloalkyl group may be attached via a heteroatom if feasible;

$(C_{3-7})$cycloalkoxy means a cycloalkyl group having 3-7 carbon atoms, with the same meaning as previously defined, attached via a ring carbon atom to an exocyclic oxygen atom;

$(C_{6-10})$aryl means an aromatic hydrocarbon group having 6-10 carbon atoms, such as phenyl, naphthyl, tetrahydronaphthyl or indenyl; the preferred $(C_{6-10})$aryl group is phenyl;

$(C_{1-5})$heteroaryl means a substituted or unsubstituted aromatic group having 1-5 carbon atoms and 1-4 heteroatoms selected from N, O and/or S; the $(C_{1-5})$heteroaryl may optionally be substituted; preferred $(C_{1-5})$heteroaryl groups are tetrazolyl, imidazolyl, thiadiazolyl, pyridyl, pyrimidyl, triazinyl, thienyl or furyl, a more preferred $(C_{1-5})$heteroaryl is pyrimidyl;

$(C_{1-9})$heteroaryl means a substituted or unsubstituted aromatic group having 1-9 carbon atoms and 1-4 heteroatoms selected from N, O and/or S; the $(C_{1-9})$heteroaryl may optionally be substituted; preferred $(C_{1-9})$heteroaryl groups are quinoline, isoquinoline and indole;

$[(C_{1-4})$alkyl]amino means an amino group, monosubstituted with an alkyl group containing 1-4 carbon atoms having the same meaning as previously defined; preferred $[(C_{1-4})$alkyl]amino group is methylamino;

di$[(C_{1-4})$alkyl]amino means an amino group, disubstituted with alkyl group(s), each containing 1-4 carbon atoms and having the same meaning as previously defined; preferred di$[(C_{1-4})$alkyl]amino group is dimethylamino;

halogen means fluorine, chlorine, bromine or iodine;

$(C_{1-3})$alkyl-C(O)—S—$(C_{1-3})$alkyl means an alkyl-carbonyl-thio-alkyl group, each of the alkyl groups having 1 to 3 carbon atoms with the same meaning as previously defined;

$(C_{3-7})$cycloalkenyl means a cycloalkenyl group having 3-7 carbon atoms, preferably 5-7 carbon atoms; preferred $(C_{3-7})$cycloalkenyl groups are cyclopentenyl or cyclohexenyl; cyclohexenyl groups are most preferred;

$(C_{2-6})$heterocycloalkenyl means a heterocycloalkenyl group having 2-6 carbon atoms, preferably 3-5 carbon atoms; and 1 heteroatom selected from N, O and/or S; preferred $(C_{2-6})$heterocycloalkenyl groups are oxycyclohexenyl and azacyclohexenyl group.

In the above definitions with multifunctional groups, the attachment point is at the last group.

When, in the definition of a substituent, it is indicated that "all of the alkyl groups" of said substituent are optionally substituted, this also includes the alkyl moiety of an alkoxy group.

A circle in a ring of Formula (I) indicates that the ring is aromatic.

Depending on the ring formed, the nitrogen, if present in X or Y, may carry a hydrogen.

In an embodiment of Formula (I), $B_1$ is $C(R_7)$; $B_2$ is $C(R_8)$; $B_3$ is $C(R_9)$; $B_4$ is $C(R_{10})$; $R_7$, $R_9$, and $R_{10}$ are each H; and $R_8$ is hydrogen or methyl.

In an embodiment of Formula (I), the ring containing X, Y and Z is selected from the group consisting of pyridyl, pyrimidyl, pyridazyl, triazinyl, thiazolyl, oxazolyl and isoxazolyl.

In an embodiment of Formula (I), the ring containing X, Y and Z is selected from the group consisting of pyridyl, pyrimidyl and pyridazyl.

In an embodiment of Formula (I), the ring containing X, Y and Z is selected from the group consisting of pyridyl and pyrimidyl.

In an embodiment of Formula (I), the ring containing X, Y and Z is pyridyl.

In an embodiment of Formula (I), $R_5$ is selected from the group consisting of hydrogen, fluorine, methyl, methoxy and trifluoromethyl.

In an embodiment of Formula (I), $R_5$ is hydrogen.

In an embodiment of Formula (I), $R_2$ and $R_3$ together form a heterocycloalkyl ring selected from the group consisting of azetidinyl, pyrrolidinyl, piperidinyl, homopiperidinyl and morpholinyl, optionally substituted with one or more of fluoro, hydroxyl, $(C_{1-3})$alkyl and $(C_{1-3})$alkoxy.

In an embodiment of Formula (I), $R_2$ and $R_3$ together form a heterocycloalkyl ring selected from the group consisting of azetidinyl, pyrrolidinyl and piperidinyl.

In an embodiment of Formula (I), $R_2$ and $R_3$ together form a pyrrolidinyl ring.

In an embodiment of Formula (I), $R_1$ is independently selected from the group consisting of $(C_{1-6})$alkyl, $(C_{2-6})$alkenyl or $(C_{2-6})$alkynyl, each optionally substituted with one or more substituents selected from the group consisting of hydroxyl, $(C_{1-4})$alkyl, $(C_{3-7})$cycloalkyl, $[(C_{1-4})$alkyl] amino, di$[(C_{1-4})$alkyl] amino, $(C_{1-3})$alkoxy, $(C_{3-7})$cycloalkoxy, $(C_{6-10})$aryl and $(C_{3-7})$heterocycloalkyl.

In an embodiment of Formula (I), $B_1$, $B_2$, $B_3$ and $B_4$ are CH; X is N; Y and Z are CH; $R_5$ is $CH_3$; A is N; $R_2$, $R_3$ and $R_4$ are H; and $R_1$ is CO—$CH_3$.

In an embodiment of Formula (I), $B_1$, $B_2$, $B_3$ and $B_4$ are CH; X and Y are N; Z is CH; $R_5$ is $CH_3$; A is N; $R_2$, $R_3$ and $R_4$ are H; and $R_1$ is CO—$CH_3$.

In an embodiment of Formula (I), $B_1$, $B_2$, $B_3$ and $B_4$ are CH; X and Y are N; Z is CH; $R_5$ is $CH_3$; A is CH; $R_2$ and $R_3$ together form a piperidinyl ring; $R_4$ is H; and $R_1$ is CO-ethenyl.

In an embodiment of Formula (I), $B_1$, $B_2$, $B_3$ and $B_4$ are CH; X, Y and Z are CH; $R_5$ is H; A is CH; $R_2$ and $R_3$ together form a pyrrolidinyl ring; $R_4$ is H; and $R_1$ is CO-propynyl.

In an embodiment of Formula (I), $B_1$, $B_2$, $B_3$ and $B_4$ are CH; X, Y and Z are CH; $R_5$ is $CH_3$; A is CH; $R_2$ and $R_3$ together form a piperidinyl ring; $R_4$ is H; and $R_1$ is CO-propynyl.

In an embodiment of Formula (I), $B_1$, $B_2$, $B_3$ and $B_4$ are CH; X and Y are N; Z is CH; $R_5$ is H; A is CH; $R_2$ and $R_3$ together form a morpholinyl ring; $R_4$ is H; and $R_1$ is CO-ethenyl.

In an embodiment of Formula (I), $B_1$, $B_2$, $B_3$ and $B_4$ are CH; X and Y are N; Z is CH; $R_5$ is $CH_3$; A is CH; $R_2$ and $R_3$ together form a morpholinyl ring; $R_4$ is H; and $R_1$ is CO-propynyl.

In an embodiment, the BTK inhibitor is a compound of Formula (II):

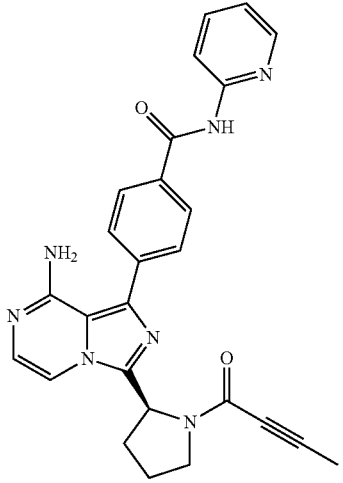

Formula (II)

or a pharmaceutically acceptable salt, solvate, hydrate, cocrystal, or prodrug thereof. The preparation of this compound is described in International Patent Application Publication No. WO 2013/010868, the disclosure of which is incorporated herein by reference.

In an embodiment, the BTK inhibitor is (S)-4-(8-amino-3-(1-(but-2-ynoyl)pyrrolidin-2-yl)imidazo[1,5-a]pyrazin-1-yl)-N-(pyridin-2-yl)benzamide or pharmaceutically acceptable salt, solvate, hydrate, cocrystal, or prodrug thereof. In other embodiments, the BTK inhibitors include, but are not limited to, those compounds described in International Patent Application Publication No. WO 2013/010868, the disclosures of each of which are specifically incorporated by reference herein.

In an embodiment, the BTK inhibitor is a compound of Formula (III) or a pharmaceutically acceptable salt, solvate, hydrate, cocrystal, or prodrug of a compound of Formula (III):

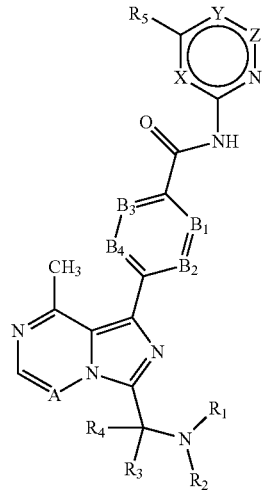

Formula (III)

In Formula (III) the substituents are defined as
X is CH, N, O or S;
Y is $C(R_6)$, N, O or S;
Z is CH, N or bond;
A is CH or N;
$B_1$ is N or $C(R_7)$;
$B_2$ is N or $C(R_8)$;
$B_3$ is N or $C(R_9)$;
$B_4$ is N or $C(R_{10})$;
$R_1$ is $R_{11}C(O)$, $R_{12}S(O)$, $R_{13}SO_2$ or $(C_{1-6})$alkyl optionally substituted with $R_{14}$;
$R_2$ is H, $(C_{1-3})$alkyl or $(C_{3-7})$cycloalkyl;
$R_3$ is H, $(C_{1-6})$alkyl or $(C_{3-7})$cycloalkyl); or
$R_2$ and $R_3$ form, together with the N and C atom they are attached to, a $(C_{3-7})$heterocycloalkyl optionally substituted with one or more fluorine, hydroxyl, $(C_{1-3})$alkyl, $(C_{1-3})$alkoxy or oxo;
$R_4$ is H or $(C_{1-3})$alkyl;
$R_5$ is H, halogen, cyano, $(C_{1-4})$alkyl, $(C_{1-3})$alkoxy, $(C_{3-6})$cycloalkyl; all alkyl groups of R5 are optionally substituted with one or more halogen; or $R_5$ is $(C_{6-10})$aryl or $(C_{2-6})$heterocycloalkyl;
$R_6$ is H or $(C_{1-3})$alkyl; or $R_5$ and $R_6$ together may form a $(C_{3-7})$cycloalkenyl, or $(C_{2-6})$heterocycloalkenyl; each optionally substituted with $(C_{1-3})$alkyl, or one or more halogen;
$R_7$ is H, halogen, $CF_3$, $(C_{1-3})$alkyl or $(C_{1-3})$alkoxy;
$R_8$ is H, halogen, $CF_3$, $(C_{1-3})$alkyl or $(C_{1-3})$alkoxy; or $R_7$ and $R_8$ together with the carbon atoms they are attached to, form $(C_{6-10})$aryl or $(C_{1-5})$heteroaryl;
$R_9$ is H, halogen, $(C_{1-3})$alkyl or $(C_{1-3})$alkoxy;

$R_{10}$ is H, halogen, $(C_{1-3})$alkyl or $(C_{1-3})$alkoxy;

$R_{11}$ is independently selected from a group consisting of $(C_{1-6})$alkyl, $(C_{2-6})$alkenyl and $(C_{2-6})$alkynyl each alkyl, alkenyl or alkynyl optionally substituted with one or more groups selected from hydroxyl, $(C_{1-4})$alkyl, $(C_{3-7})$cycloalkyl, [$(C_{1-4})$alkyl]amino, di[$(C_{1-4})$alkyl]amino, $(C_{1-3})$alkoxy, $(C_{3-7})$cycloalkoxy, $(C_{6-10})$aryl or $(C_{3-7})$heterocycloalkyl, or $R_{11}$ is $(C_{1-3})$alkyl-C(O)—S—$(C_{1-3})$alkyl; or $R_{11}$ is $(C_{1-5})$heteroaryl optionally substituted with one or more groups selected from halogen or cyano.

$R_{12}$ and $R_{13}$ are independently selected from a group consisting of $(C_{2-6})$alkenyl or $(C_{2-6})$alkynyl both optionally substituted with one or more groups selected from hydroxyl, $(C_{1-4})$alkyl, $(C_{3-7})$cycloalkyl, [$(C_{1-4})$alkyl]amino, di[$(C_{1-4})$alkyl]amino, $(C_{1-3})$alkoxy, $(C_{3-7})$cycloalkoxy, $(C_{6-10})$aryl, or $(C_{3-7})$heterocycloalkyl; or $(C_{1-5})$heteroaryl optionally substituted with one or more groups selected from halogen or cyano;

$R_{14}$ is independently selected from a group consisting of halogen, cyano or $(C_{2-6})$alkenyl or $(C_{2-6})$alkynyl both optionally substituted with one or more groups selected from hydroxyl, $(C_{1-4})$alkyl, $(C_{3-7})$cycloalkyl, [$(C_{1-4})$alkyl]amino, di[$(C_{1-4})$alkyl]amino, $(C_{1-3})$alkoxy, $(C_{3-7})$cycloalkoxy, $(C_{6-10})$aryl, $(C_{1-5})$heteroaryl or $(C_{3-7})$heterocycloalkyl;

with the proviso that
  0 to 2 atoms of X, Y, Z can simultaneously be a heteroatom;
  when one atom selected from X, Y is O or S, then Z is a bond and the other atom selected from X, Y cannot be O or S;
  when Z is C or N then Y is $C(R_6)$ or N and X is C or N;
  0 to 2 atoms of $B_1$, $B_2$, $B_3$ and $B_4$ are N;

with the terms used having the following meanings:

$(C_{1-3})$alkyl means a branched or unbranched alkyl group having 1-3 carbon atoms, being methyl, ethyl, propyl or isopropyl;

$(C_{1-4})$alkyl means a branched or unbranched alkyl group having 1-4 carbon atoms, being methyl, ethyl, propyl, isopropyl, butyl, isobutyl, sec-butyl and tert-butyl, $(C_{1-3})$ alkyl groups being preferred;

$(C_{1-6})$alkyl means a branched or unbranched alkyl group having 1-6 carbon atoms, for example methyl, ethyl, propyl, isopropyl, butyl, tert-butyl, n-pentyl and n-hexyl. $(C_{1-5})$alkyl groups are preferred, $(C_{1-4})$alkyl being most preferred;

$(C_{1-2})$alkoxy means an alkoxy group having 1-2 carbon atoms, the alkyl moiety having the same meaning as previously defined;

$(C_{1-3})$alkoxy means an alkoxy group having 1-3 carbon atoms, the alkyl moiety having the same meaning as previously defined, with $(C_{1-2})$alkoxy groups preferred;

$(C_{2-3})$alkenyl means an alkenyl group having 2-3 carbon atoms, such as ethenyl or 2-propenyl;

$(C_{2-4})$alkenyl means a branched or unbranched alkenyl group having 2-4 carbon atoms, such as ethenyl, 2-propenyl, isobutenyl or 2-butenyl;

$(C_{2-6})$alkenyl means a branched or unbranched alkenyl group having 2-6 carbon atoms, such as ethenyl, 2-butenyl, and n-pentenyl, with $(C_{2-4})$alkenyl groups preferred, and $(C_{2-3})$alkenyl groups even more preferred;

$(C_{2-4})$alkynyl means a branched or unbranched alkynyl group having 2-4 carbon atoms, such as ethynyl, 2-propynyl or 2-butynyl;

$(C_{2-3})$alkynyl means an alkynyl group having 2-3 carbon atoms, such as ethynyl or 2-propynyl;

$(C_{2-6})$alkynyl means a branched or unbranched alkynyl group having 2-6 carbon atoms, such as ethynyl, propynyl, n-butynyl, n-pentynyl, isopentynyl, isohexynyl or n-hexynyl, with $(C_{2-4})$alkynyl groups preferred, and $(C_{2-3})$alkynyl groups more preferred;

$(C_{3-6})$cycloalkyl means a cycloalkyl group having 3-6 carbon atoms, being cyclopropyl, cyclobutyl, cyclopentyl or cyclohexyl;

$(C_{3-7})$cycloalkyl means a cycloalkyl group having 3-7 carbon atoms, being cyclopropyl, cyclobutyl, cyclopentyl, cyclohexyl or cycloheptyl;

$(C_{2-6})$heterocycloalkyl means a heterocycloalkyl group having 2-6 carbon atoms, preferably 3-5 carbon atoms, and one or two heteroatoms selected from N, O and/or S, which may be attached via a heteroatom if feasible, or a carbon atom; preferred heteroatoms are N or O; preferred groups are piperidine, morpholine, pyrrolidine and piperazine; a most preferred $(C_{2-6})$heterocycloalkyl is pyrrolidine; and the heterocycloalkyl group may be attached via a heteroatom if feasible;

$(C_{3-7})$heterocycloalkyl means a heterocycloalkyl group having 3-7 carbon atoms, preferably 3-5 carbon atoms, and one or two heteroatoms selected from N, O and/or S; preferred heteroatoms are N or O; preferred $(C_{3-7})$ heterocycloalkyl groups are azetidinyl, pyrrolidinyl, piperidinyl, homopiperidinyl or morpholinyl; more preferred $(C_{3-7})$heterocycloalkyl groups are piperidine, morpholine and pyrrolidine; even more preferred are piperidine and pyrrolidine; and the heterocycloalkyl group may be attached via a heteroatom if feasible;

$(C_{3-7})$cycloalkoxy means a cycloalkyl group having 3-7 carbon atoms, with the same meaning as previously defined, attached via a ring carbon atom to an exocyclic oxygen atom;

$(C_{6-10})$aryl means an aromatic hydrocarbon group having 6-10 carbon atoms, such as phenyl, naphthyl, tetrahydronaphthyl or indenyl; the preferred $(C_{6-10})$aryl group is phenyl;

$(C_{1-5})$heteroaryl means a substituted or unsubstituted aromatic group having 1-5 carbon atoms and 1-4 heteroatoms selected from N, O and/or S, wherein the $(C_{1-5})$heteroaryl may optionally be substituted. preferred $(C_{1-5})$heteroaryl groups are tetrazolyl, imidazolyl, thiadiazolyl, pyridyl, pyrimidyl, triazinyl, thienyl or furyl, and the more preferred $(C_{1-5})$heteroaryl is pyrimidyl;

[$(C_{1-4})$alkyl]amino means an amino group, monosubstituted with an alkyl group containing 1-4 carbon atoms having the same meaning as previously defined; the preferred [$(C_{1-4})$alkyl]amino group is methylamino;

di[$(C_{1-4})$alkyl]amino means an amino group, disubstituted with alkyl group(s), each containing 1-4 carbon atoms and having the same meaning as previously defined; the preferred di[$(C_{1-4})$alkyl]amino group is dimethylamino;

Halogen means fluorine, chlorine, bromine or iodine;

$(C_{1-3})$alkyl-C(O)—S—$(C_{1-3})$alkyl means an alkyl-carbonyl-thio-alkyl group, each of the alkyl groups having 1 to 3 carbon atoms with the same meaning as previously defined;

$(C_{3-7})$cycloalkenyl means a cycloalkenyl group having 3-7 carbon atoms, preferably 5-7 carbon atoms; preferred $(C_{3-7})$cycloalkenyl groups are cyclopentenyl or cyclohexenyl; and cyclohexenyl groups are most preferred;

$(C_{2-6})$heterocycloalkenyl means a heterocycloalkenyl group having 2-6 carbon atoms, preferably 3-5 carbon atoms; and 1 heteroatom selected from N, O and/or S; the preferred $(C_{2-6})$heterocycloalkenyl groups are oxycyclohexenyl and azacyclohexenyl groups.

In the above definitions with multifunctional groups, the attachment point is at the last group.

When, in the definition of a substituent, is indicated that "all of the alkyl groups" of said substituent are optionally substituted, this also includes the alkyl moiety of an alkoxy group.

A circle in a ring of Formula (III) indicates that the ring is aromatic.

Depending on the ring formed, the nitrogen, if present in X or Y, may carry a hydrogen.

In one aspect the invention relates to a compound according to Formula (III) wherein $B_1$ is $C(R_7)$; $B_2$ is $C(R_8)$; $B_3$ is $C(R_9)$ and $B_4$ is $C(R_{10})$.

In other embodiments, the BTK inhibitors include, but are not limited to, those compounds described in International Patent Application Publication No. WO 2013/010869, the disclosures of each of which are specifically incorporated by reference herein.

In an embodiment, the BTK inhibitor is a compound of Formula (IV):

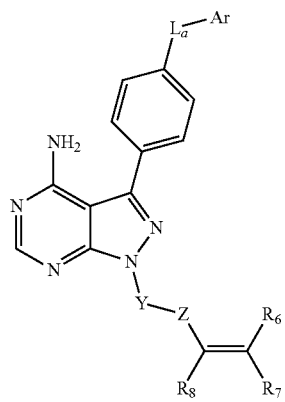

Formula (IV)

or a pharmaceutically acceptable salt, solvate, hydrate, cocrystal, or prodrug thereof, wherein:

$L_a$ is $CH_2$, O, NH or S;

Ar is a substituted or unsubstituted aryl, or a substituted or unsubstituted heteroaryl;

Y is an optionally substituted group selected from the group consisting of alkyl, heteroalkyl, cycloalkyl, heterocycloalkyl, aryl and heteroaryl;

Z is C(=O), OC(=O), NRC(=O), C(=S), S(=O)$_x$, OS(=O)$_x$ or NRS(=O), where x is 1 or 2;

$R^7$ and $R^8$ are each independently H; or $R^7$ and $R^8$ taken together form a bond;

$R^6$ is H; and

R is H or $(C_{1-6})$alkyl.

In an embodiment, the BTK inhibitor is ibrutinib or a pharmaceutically acceptable salt, solvate, hydrate, cocrystal, or prodrug thereof. In an embodiment, the BTK inhibitor is (R)-1-(3-(4-amino-3-(4-phenoxyphenyl)-1H-pyrazolo[3,4-d]pyrimidin-1-yl)piperidin-1-yl)prop-2-en-1-one. In an embodiment, the BTK inhibitor is 1-[(3R)-3-[4-amino-3-(4-phenoxyphenyl)-1H-pyrazolo[3,4-d]pyrimidin-1-yl]piperidin-1-yl]prop-2-en-1-one. In another embodiment, the BTK inhibitor is (S)-1-(3-(4-amino-3-(4-phenoxyphenyl)-1H-pyrazolo[3,4-d]pyrimidin-1-yl)piperidin-1-yl)prop-2-en-1-one. In an embodiment, the BTK inhibitor has the structure of Formula (V), or an enantiomer thereof, or a pharmaceutically acceptable salt, solvate, hydrate, cocrystal, or prodrug thereof.

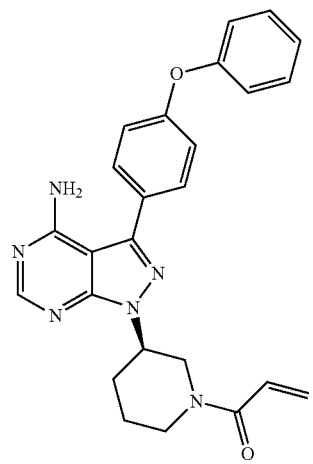

Formula (V)

In an embodiment, the BTK inhibitor is a compound of Formula (VI):

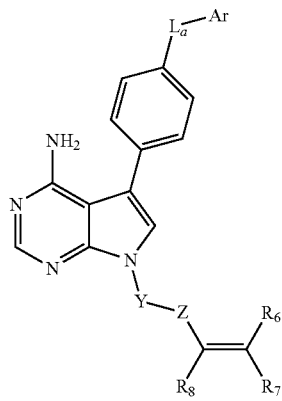

Formula (VI)

or a pharmaceutically acceptable salt, solvate, hydrate, cocrystal, or prodrug thereof, wherein:

$L_a$ is $CH_2$, O, NH or S;

Ar is a substituted or unsubstituted aryl, or a substituted or unsubstituted heteroaryl;

Y is an optionally substituted group selected from the group consisting of alkyl, heteroalkyl, cycloalkyl, heterocycloalkyl, aryl and heteroaryl;

Z is C(=O), OC(=O), NRC(=O), C(=S), S(=O)$_x$, OS(=O)$_x$ or NRS(=O)$_x$, where x is 1 or 2;

$R^7$ and $R^8$ are each H; or $R^7$ and $R^8$ taken together form a bond;

$R^6$ is H; and

R is H or $(C_{1-6})$alkyl.

In an embodiment, the BTK inhibitor is a compound of Formula (VII):

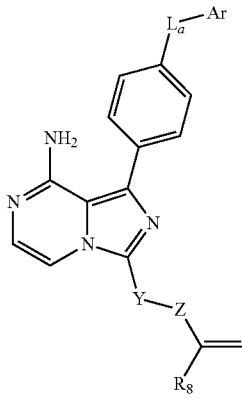

Formula (VII)

or a pharmaceutically acceptable salt, solvate, hydrate, cocrystal, or prodrug thereof,
wherein:
$L_a$ is $CH_2$, O, NH or S;
Ar is a substituted or unsubstituted aryl, or a substituted or unsubstituted heteroaryl;
Y is an optionally substituted group selected from the group consisting of alkyl, heteroalkyl, cycloalkyl, heterocycloalkyl, aryl and heteroaryl;
Z is C(=O), OC(=O), NRC(=O), C(=S), S(=O)$_x$, OS(=O)$_x$ or NRS(=O)$_x$, where x is 1 or 2;
$R^7$ and $R^8$ are each H; or $R^7$ and $R^8$ taken together form a bond;
$R^6$ is H; and
R is H or $(C_{1-6})$alkyl.

In an embodiment, the BTK inhibitor is a compound of Formula (VIII):

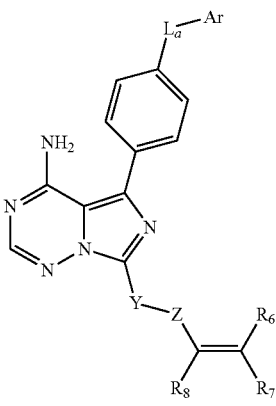

Formula (VIII)

or a pharmaceutically acceptable salt, solvate, hydrate, cocrystal, or prodrug thereof,
wherein:
$L_a$ is $CH_2$, O, NH or S;
Ar is a substituted or unsubstituted aryl, or a substituted or unsubstituted heteroaryl;
Y is an optionally substituted group selected from the group consisting of alkyl, heteroalkyl, cycloalkyl, heterocycloalkyl, aryl and heteroaryl;
Z is C(=O), OC(=O), NRC(=O), C(=S), S(=O)$_x$, OS(=O)$_x$ or NRS(=O)$_x$, where x is 1 or 2;
$R^7$ and $R^8$ are each H; or $R^7$ and $R^8$ taken together form a bond;
$R^6$ is H; and
R is H or $(C_{1-6})$alkyl.

In an embodiment, the BTK inhibitor is a compound disclosed in U.S. Pat. No. 7,459,554, the disclosure of which is specifically incorporated herein by reference. In an embodiment, the BTK inhibitor is a compound of Formula (IX):

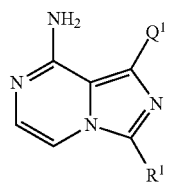

Formula (IX)

or a pharmaceutically acceptable salt, solvate, hydrate, cocrystal, or prodrug thereof, wherein:
$Q^1$ is aryl$^1$, heteroaryl$^1$, cycloalkyl, heterocyclyl, cycloalkenyl, or heterocycloalkenyl, any of which is optionally substituted by one to five independent $G^1$ substituents;
$R^1$ is alkyl, cycloalkyl, bicycloalkyl, aryl, heteroaryl, aralkyl, heteroaralkyl, heterocyclyl, or heterobicycloalkyl, any of which is optionally substituted by one or more independent $G^{11}$ substituents;
$G^1$ and $G^{41}$ are each independently halo, oxo, —$CF_3$, —$OCF_3$, —$OR^2$, —$NR^2R^3(R^{3a})_{j1}$, —$C(O)R^2$, —$CO_2R^2$, —$CONR^2R^3$, —$NO_2$, —CN, —$S(O)_{j1}R^2$, —$SO_2NR^2R^3$, $NR^2(C=O)R^3$, $NR^2(C=O)OR^3$, $NR^2(C=O)NR^2R^3$, $NR^2S(O)_{j1}R^3$, —(C=S)$OR^2$, —(C=O)$SR^2$, —$NR^2(C=NR^3)NR^{2a}R^{3a}$, —$NR^2(C=NR^3)OR^{2a}$, —$NR^2(C=NR^3)SR^{3a}$, —O(C=O)$OR^2$, —O(C=O)$NR^2R^3$, —O(C=O)$SR^2$, —S(C=O)$OR^2$, —S(C=O)$NR^2R^3$, $(C_{0-10})$alkyl, $(C_{2-10})$alkenyl, $(C_{2-10})$alkynyl, $(C_{1-10})$alkoxy$(C_{1-10})$alkyl, $(C_{1-10})$alkoxy$(C_{2-10})$alkenyl, $(C_{1-10})$alkoxy$(C_{2-10})$alkynyl, $(C_{1-10})$alkylthio$(C_{1-10})$alkyl, $(C_{1-10})$alkylthio$(C_{2-10})$alkenyl, $(C_{1-10})$alkylthio$(C_{2-10})$alkynyl, cyclo$(C_{3-8})$alkyl, cyclo$(C_{3-8})$alkenyl, cyclo$(C_{3-8})$alkyl$(C_{1-10})$alkyl, cyclo$(C_{3-8})$alkenyl$(C_{1-10})$alkyl, cyclo$(C_{3-8})$alkyl$(C_{2-10})$alkenyl, cyclo$(C_{3-8})$alkenyl$(C_{2-10})$alkenyl, cyclo$(C_{3-8})$alkyl$(C_{2-10})$alkynyl, cyclo$(C_{3-8})$alkenyl$(C_{2-10})$alkynyl, heterocyclyl-$(C_{0-10})$alkyl, heterocyclyl-$(C_{2-10})$alkenyl, or heterocyclyl-$(C_{2-10})$alkynyl, any of which is optionally substituted with one or more independent halo, oxo, —$CF_3$, —$OCF_3$, —$OR^{222}$, —$NR^{222}R^{333}(R^{333}a)_{j1a}$, —$C(O)R^{222}$, —$CO_2R^{222}$, —$CONR^{222}R^{333}$, —$NO_2$, —CN, —$S(O)_{j1a}R^{222}$, —$SO_2NR^{222}R^{333}$, $NR^{222}(C=O)R^{333}$, $NR^{222}(C=O)OR^{333}$, $NR^{222}(C=O)NR^{222}R^{333}$, $NR^{222}S(O)_{j1a}R^{333}$, —(C=S)$OR^{222}$, —(C=O)$SR^{222}$, —$NR^{222}(C=NR^{333})NR^{222a}R^{333a}$, —$NR^{222}(C=NR^{333})OR^{222a}$, —$NR^{222}(C=NR^{333})SR^{333a}$, —O(C=O)$OR^{222}$, —O(C=O)$NR^{222}R^{333}$, —O(C=O)$SR^{222}$, —S(C=O)$OR^{222}$, or —S(C=O)$NR^{222}R^{333}$ substituents; or —(X$^1$)$_m$—(Y$^1$)$_m$—R$^4$; or aryl-$(C_{0-10})$alkyl, aryl-$(C_{2-10})$alkenyl, or aryl-$(C_{2-10})$ alkynyl, any of which is optionally substituted with one or more independent halo, —$CF_3$, —$OCF_3$, —$OR^{222}$, —$NR^{222}R^{333}(R^{333a})_{j2a}$, —$C(O)R^{222}$, —$CO_2R^{222}$, —$CONR^{222}R^{333}$, —$NO_2$, —CN, —$S(O)_{j2a}R^{222}$, —$SO_2NR^{222}R^{333}$, $NR^{222}(C=O)R^{333}$, $NR^{222}(C=O)OR^{333}$, $NR^{222}(C=O)NR^{222}R^{333}$, $NR^{222}S(O)_{j2a}R^{333}$, —(C=S)$OR^{222}$, —(C=O)$SR^{222}$, —$NR^{222}(C=NR^{333})NR^{222a}R^{333a}$, —$NR^{222}(C=NR^{333})OR^{222a}$, —$NR^{222}(C=NR^{333})SR^{333a}$, —O(C=O)$OR^{222}$, —O(C=O)$NR^{222}R^{333}$, —O(C=O)$SR^{222}$, —S(C=O)

$OR^{222}$, or $-S(C=O)NR^{222}R^{333}$ substituents; or hetaryl-$(C_{0-10})$alkyl, hetaryl-$(C_{2-10})$alkenyl, or hetaryl-$(C_{2-10})$alkynyl, any of which is optionally substituted with one or more independent halo, $-CF_3$, $-OCF_3$, $-OR^{222}$, $-NR^{222}$, $R^{333}(R^{333a})_{j3a}$, $-C(O)R^{222}$, $-CO_2R^{222}$, $-CONR^{222}R^{333}$, $-NO_2$, $-CN$, $-S(O)_{j3a}R^{222}$, $-SO_2NR^{222}R^{333}$, $NR^{222}(C=O)R^{333}$, $NR^{222}(C=O)OR^{333}$, $NR^{222}(C=O)NR^{222}R^{333}$, $NR^{222}S(O)_{j3a}R^{333}$, $-(C=S)OR^{222}$, $-(C=O)SR^{222}$, $-NR^{222}(C=NR^{333})NR^{222a}R^{333a}$, $-NR^{222}(C=NR^{333})OR^{222a}$, $-NR^{222}(C=NR^{333})SR^{333a}$, $-O(C=O)OR^{222}$, $-O(C=O)NR^{222}R^{333}$, $-O(C=O)SR^{222}$, $-S(C=O)OR^{222}$, or $-S(C=O)NR^{222}R^{333}$ substituents;

$G^{11}$ is halo, oxo, $-CF_3$, $-OCF_3$, $-OR^{21}$, $-NR^{21}R^{31}(R^{3a1})_{j4}$, $-C(O)R^{21}$, $-CO_2R^{21}$, $-CONR^{21}R^{31}$, $-NO_2$, $-CN$, $-S(O)_{j4}R^{21}$, $-SO_2NR^{21}R^{31}$, $NR^{21}(C=O)R^{31}$, $NR^{21}(C=O)OR^{31}$, $NR^{21}(C=O)NR^{21}R^{31}$, $NR^{21}S(O)_{j4}R^{31}$, $-(C=S)OR^{21}$, $-(C=O)SR^{21}$, $-NR^{21}(C=NR^{31})NR^{2a1}R^{3a1}$, $-NR^{21}(C=NR^{31})OR^{2a1}$, $-NR^{21}(C=NR^{31})SR^{3a1}$, $-O(C=O)OR^{21}$, $-O(C=O)NR^{21}R^{31}$, $-O(C=O)SR^{21}$, $-S(C=O)OR^{21}$, $-S(C=O)NR^{21}R^{31}$, $-P(O)OR^{21}OR^{31}$, $(C_{0-10})$alkyl, $(C_{2-10})$alkenyl, $(C_{2-10})$alkynyl, $(C_{1-10})$ alkoxy$(C_{1-10})$alkyl, $(C_{1-10})$alkoxy$(C_{2-10})$alkenyl, $(C_{1-10})$alkoxy$(C_{2-10})$alkynyl, $(C_{1-10})$ alkylthio$(C_{1-10})$alkyl, $(C_{1-10})$alkylthio$(C_{2-10})$alkenyl, $(C_{1-10})$alkylthio$(C_{2-10})$alkynyl, cyclo$(C_{3-8})$alkyl, cyclo$(C_{3-8})$alkenyl, cyclo$(C_{3-8})$alkyl$(C_{1-10})$alkyl, cyclo$(C_{3-8})$alkenyl$(C_{1-10})$ alkyl, cyclo$(C_{3-8})$alkyl$(C_{2-10})$alkenyl, cyclo$(C_{3-8})$alkenyl$(C_{2-10})$alkenyl, cyclo $(C_{3-8})$ alkyl$(C_{2-10})$ alkynyl, cyclo$(C_{3-8})$alkenyl$(C_{2-10})$ alkynyl, heterocyclyl-$(C_{0-10})$alkyl, heterocyclyl-$(C_{2-10})$alkenyl, or heterocyclyl-$(C_{2-10})$alkynyl, any of which is optionally substituted with one or more independent halo, oxo, $-CF_3$, $-OCF_3$, $-OR^{2221}$, $-NR^{2221}R^{3331}(R^{3331})_{j4a}$, $C(O)R^{2221}$, $-CO_2R^{2221}$, $-CONR^{2221}R^{3331}$, $-NO_2$, $-CN$, $-S(O)_{j4a}R^{2221}$, $-SO_2NR^{2221}R^{3331}$, $NR^{2221}(C=O)R^{3331}$, $NR^{2221}(C=O)OR^{3331}$, $NR^{2221}(C=O)NR^{2221}R^{3331}$, $NR^{2221}S(O)_{j4a}R^{3331}$, $-C(C=S)OR^{2221}$, $-(C=O)SR^{2221}$, $-NR^{2221}(C=NR^{3331})NR^{222a1}R^{333a1}$, $-NR^{2221}(C=NR^{3331})OR^{222a1}$, $-NR^{2221}(C=NR^{3331})SR^{333a1}$, $-O(C=O)OR^{2221}$, $-O(C=O)NR^{2221}R^{3331}$, $-O(C=O)SR^{2221}$, $-S(C=O)OR^{2221}$, $-P(O)OR^{2221}OR^{3331}$, or $-S(C=O)NR^{2221}R^{3331}$ substituents; or aryl-$(C_{0-10})$alkyl, aryl-$(C_{2-10})$alkenyl, or aryl-$(C_{2-10})$alkynyl, any of which is optionally substituted with one or more independent halo, $-CF_3$, $-OCF_3$, $-OR^{2221}$, $-NR^{2221}R^{3331}(R^{333a1})_{j5a}$, $-C(O)R^{2221}$, $-CO_2R^{2221}$, $-CONR^{2221}R^{3331}$, $-NO_2$, $-CN$, $-S(O)_{j5a}R^{2221}$, $-SO_2NR^{2221}R^{3331}$, $NR^{2221}(C=O)R^{3331}$, $NR^{2221}(C=O)OR^{3331}$, $NR^{2221}(C=O)NR^{2221}R^{3331}$, $NR^{2221}S(O)_{j5a}R^{3331}$, $-(C=O)OR^{2221}$, $-(C=O)SR^{2221}$, $-NR^{2221}(C=NR^{3331})NR^{222a1}R^{333a1}$, $-NR^{2221}(C=NR^{3331})OR^{222a1}$, $-NR^{2221}(C=NR^{3331})SR^{333a1}$, $-O(C=O)OR^{2221}$, $-O(C=O)NR^{2221}R^{3331}$, $-O(C=O)SR^{2221}$, $-S(C=O)OR^{2221}$, $-P(O)OR^{2221}R^{3331}$, or $-S(C=O)NR^{2221}R^{3331}$ substituents; or hetaryl-$(C_{0-10})$ alkyl, hetaryl-$(C_{2-10})$alkenyl, or hetaryl-$(C_{2-10})$alkynyl, any of which is optionally substituted with one or more independent halo, $-CF_3$, $-OCF_3$, $-OR^{2221}$, $-NR^{2221}R^{3331}(R^{333a1})_{j6a}$, $-C(O)R^{2221}$, $-CO_2R^{2221}$, $-CONR^{2221}R^{3331}$, $-NO_2$, $-CN$, $-S(O)_{j6a}R^{2221}$, $-SO_2NR^{2221}R^{3331}$, $NR^{2221}(C=O)R^{3331}$, $NR^{2221}(C=O)OR^{3331}$, $NR^{2221}(C=O)NR^{2221}R^{3331}$, $NR^{2221}S(O)_{j6a}R^{3331}$, $-(C=S)OR^{2221}$, $-(C=O)SR^{2221}$, $-NR^{2221}(C=NR^{3331})NR^{222a1}R^{333a1}$, $-NR^{2221}(C=NR^{3331})OR^{222a1}$, $-NR^{2221}(C=NR^{3331})SR^{333a1}$, $-O(C=O)OR^{2221}$, $-O(C=O)NR^{2221}R^{3331}$, $-O(C=O)SR^{2221}$, $-S(C=O)OR^{2221}$, $-P(O)OR^{2221}OR^{3331}$, or $-S(C=O)NR^{2221}R^{3331}$ substituents; or $G^{11}$ is taken together with the carbon to which it is attached to form a double bond which is substituted with $R^5$ and $G^{111}$;

$R^2$, $R^{2a}$, $R^3$, $R^{3a}$, $R^{222}$, $R^{222}a$, $R^{333}$, $R^{333a}$, $R^{21}$, $R^{2a1}$, $R^{31}$, $R^{3a1}$, $R^{2221}$, $R^{222a1}$, $R^{3331}$, and $R^{333a1}$ are each independently equal to $(C_{0-10})$alkyl, $(C_{2-10})$alkenyl, $(C_{2-10})$alkynyl, $(C_{1-10})$alkoxy$(C_{1-10})$alkyl, $(C_{1-10})$alkoxy$(C_{2-10})$alkenyl, $(C_{1-10})$alkoxy$(C_{2-10})$alkynyl, $(C_{1-10})$alkylthio$(C_{1-10})$alkyl, $(C_{1-10})$alkylthio$(C_{2-10})$alkenyl, $(C_{1-10})$alkylthio$(C_{2-10})$alkynyl, cyclo$(C_{3-8})$alkyl, cyclo$(C_{3-8})$alkenyl, cyclo$(C_{3-8})$alkyl$(C_{1-10})$alkyl, cyclo$(C_{3-8})$alkenyl$(C_{1-10})$alkyl, cyclo$(C_{3-8})$alkyl$(_{2-10})$alkenyl, cyclo$(C_{3-8})$alkenyl $(C_{2-10})$alkenyl, cyclo$(C_{3-8})$alkyl$(C_{2-10})$alkynyl, cyclo$(C_{3-8})$alkenyl$(C_{2-10})$alkynyl, heterocyclyl-$(C_{0-10})$alkyl, heterocyclyl-$(C_{2-10})$alkenyl, or heterocyclyl-$(C_{2-10})$alkynyl, any of which is optionally substituted by one or more $G^{111}$ substituents; or aryl-$(C_{0-10})$alkyl, aryl-$(C_{2-10})$alkenyl, or aryl-$(C_{2-10})$alkynyl, hetaryl-$(C_{0-10})$alkyl, hetaryl-$(C_{2-10})$alkenyl, or hetaryl-$(C_{2-10})$alkynyl, any of which is optionally substituted by one or more $G^{111}$ substituents; or in the case of $-NR^2R^3(R^{3a})_{j1}$ or $-NR^{222}R^{333}(R^{333}a)_{j1a}$ or $-NR^{222}R^{333}(R^{333}a)_{j2a}$ or $-NR^{2221}R^{3331}(R^{333a1})_{j3a}$ or $-NR^{2221}R^{3331}(R^{333a1})_{j4a}$ or $-NR^{2221}R^{3331}(R^{333a1})_{j5a}$ or $-NR^{2221}R^{3331}(R^{333a1})_{j6a}$, $R^2$ and $R^3$ or $R^{222}$ and $R^{333}3$ or $R^{2221}$ and $R^{3331}$ taken together with the nitrogen atom to which they are attached form a 3-10 membered saturated ring, unsaturated ring, heterocyclic saturated ring, or heterocyclic unsaturated ring, wherein said ring is optionally substituted by one or more $G^{111}$ substituents;

$X^1$ and $Y^1$ are each independently $-O-$, $-NR^7-$, $-S(O)_{j7}-$, $-CR^5R^6-$, $-N(C(O)OR^7)-$, $-N(C(O)R^7)-$, $-N(SO_2R^7)-$, $-CH_2O-$, $-CH_2S-$, $-CH_2N(R^7)-$, $-CH(NR^7)-$, $-CH_2N(C(O)R^7)-$, $-CH_2N(C(O)OR^7)-$, $-CH_2N(SO_2R^7)-$, $-CH(NHR^7)-$, $-CH(NHC(O)R^7)-$, $-CH(NHSO_2R^7)-$, $-CH(NHC(O)OR^7)-$, $-CH(OC(O)R^7)-$, $-CH(OC(O)NHR^7)-$, $-CH=CH-$, $-C.ident.C-$, $-C(=NOR^7)-$, $-C(O)-$, $-CH(OR^7)-$, $-C(O)N(R^7)-$, $-N(R^7)C(O)-$, $-N(R^7)S(O)-$, $-N(R^7)S(O)_2-$, $-OC(O)N(R^7)-$, $-N(R^7)C(O)N(R^7)-$, $-NR^7C(O)O-$, $-S(O)N(R^7)-$, $-S(O)_2N(R^7)-$, $-N(C(O)R^7)S(O)-$, $-N(C(O)R^7)S(O)_2-$, $-N(R^7)S(O)N(R^7)-$, $-N(R^7)S(O)_2N(R^7)-$, $-C(O)N(R^7)C(O)-$, $-S(O)N(R^7)C(O)-$, $-S(O)_2N(R^7)C(O)-$, $-OS(O)N(R^7)-$, $-OS(O)_2N(R^7)-$, $-N(R^7)S(O)O-$, $-N(R^7)S(O)_2O-$, $-N(R^7)S(O)C(O)-$, $-N(R^7)S(O)_2C(O)-$, $-SON(C(O)R^7)-$, $-SO_2N(C(O)R^7)-$, $N(R^7)SON(R^7)-$, $-N(R^7)SO_2N(R^7)-$, $-C(O)O-$, $-N(R^7)P(OR^8)O-$, $-N(R^7)P(OR^8)-$, $-N(R^7)P(O)(OR^8)O-$, $-N(R^7)P(O)(OR^8)-$, $-N(C(O)R^7)P(OR^8)O-$, $-N(C(O)R^7)P(OR^8)-$, $-N(C(O)R^7)P(O)(OR^8)O-$, $-N(C(O)R^7)P(OR^8)-$, $-CH(R^7)S(O)-$, $-CH(R^7)S(O)_2-$, $-CH(R^7)N(C(O)OR^7)-$, $-CH(R^7)N(C(O)R^7)-$, $-CH(R^7)N(SO_2R^7)-$, $-CH(R^7)O-$, $-CH(R^7)S-$, $-CH(R^7)N(R^7)-$, $-CH(R^7)N(C(O)R^7)-$, $-CH(R^7)N(C(O)OR^7)-$, $-CH(R^7)N(SO_2R^7)-$, $-CH(R^7)C(=NOR^7)-$, $-CH(R^7)C(O)-$, $-CH(R^7)CH(OR^7)-$, $-CH(R^7)C(O)N(R^7)-$, $-CH(R^7)N(R^7)C(O)-$, $-CH(R^7)N(R^7)S(O)-$, $-CH(R^7)N(R^7)S(O)_2-$, $-CH(R^7)OC(O)N(R^7)-$, $-CH(R^7)N(R^7)C(O)N(R^7)-$, $-CH(R^7)NR^7C(O)O-$, $-CH(R^7)S(O)N(R^7)-$, $-CH(R^7)S(O)_2N(R^7)-$, $-CH(R^7)N(C(O)R^7)S(O)-$, $-CH(R^7)N(C(O)R^7)S(O)-$, $-CH(R^7)N(R^7)S(O)N(R^7)-$, $-CH(R^7)N(R^7)S(O)_2N(R^7)-$, $-CH(R^7)C(O)N(R^7)C(O)-$, $-CH(R^7)S(O)N(R^7)C(O)-$, $-CH(R^7)S(O)_2N(R^7)C(O)-$, $-CH(R^7)OS(O)N(R^7)-$, $-CH(R^7)OS(O)_2N$ (R$^7$)—, —CH(R$^7$)N(R$^7$)S(O)O—, —CH(R$^7$)N(R$^7$)S(O)$_2$O—, —CH(R$^7$)N(R$^7$)S(O)C(O)—, —CH(R$^7$)N(R$^7$)S(O)$_2$C(O)—, —CH(R$^7$)SON(C(O)R$^7$)—, —CH(R$^7$)SO$_2$N(C(O)R$^7$)—, —CH(R$^7$)N(R$^7$)SON(R$^7$)—, —CH(R$^7$)N(R$^7$)SO$_2$N(R$^7$)—, —CH(R$^7$)C(O)O—, —CH(R$^7$)N(R$^7$)P(OR$^8$)O—, —CH(R$^7$)N(R$^7$)P(OR$^8$)—, —CH(R$^7$)N(R$^7$)P(O)(OR$^8$)O—, —CH(R$^7$)N(R$^7$)P(O)(OR$^8$)—, —CH(R$^7$)N(C(O)R$^7$)P(OR$^8$)O—, —CH(R$^7$)N(C(O)R$^7$)P(OR$^8$)—, —CH(R$^7$)N(C(O)R$^7$)P(O)(OR$^8$)O—, or —CH(R$^7$)N(C(O)R$^7$)P(OR$^8$)—;

or X$^1$ and Y$^1$ are each independently represented by one of the following structural formulas:

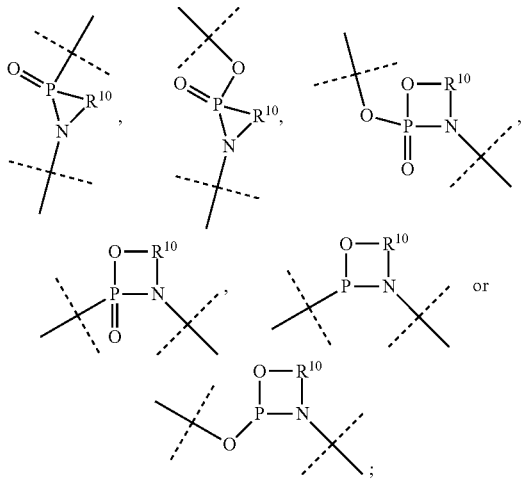

R$^{10}$, taken together with the phosphinamide or phosphonamide, is a 5-, 6-, or 7-membered aryl, heteroaryl or heterocyclyl ring system;

R$^5$, R$^6$, and G$^{111}$ are each independently a (C$_{0-10}$)alkyl, (C$_{2-10}$)alkenyl, (C$_{2-10}$)alkynyl, (C$_{1-10}$)alkoxy(C$_{1-10}$)alkyl, (C$_{1-10}$)alkoxy(C$_{2-10}$)alkenyl, (C$_{1-10}$)alkoxy(C$_{2-10}$)alkynyl, (C$_{1-10}$)alkylthio(C$_{1-10}$)alkyl, (C$_{1-10}$)alkylthio(C$_{2-10}$)alkenyl, (C$_{1-10}$)alkylthio(C$_{2-10}$)alkynyl, cyclo(C$_{3-8}$)alkyl, cyclo(C$_{3-8}$)alkenyl, cyclo(C$_{3-8}$)alkyl(C$_{1-10}$)alkyl, cyclo(C$_{3-8}$)alkenyl(C$_{1-10}$)alkyl, cyclo(C$_{3-8}$)alkyl(C$_{2-10}$)alkenyl, cyclo(C$_{3-8}$)alkenyl(C$_{2-10}$)alkenyl, cyclo(C$_{3-8}$)alkyl(C$_{2-10}$)alkynyl, cyclo(C$_{3-8}$)alkenyl(C$_{2-10}$)alkynyl, heterocyclyl-(C$_{0-10}$)alkyl, heterocyclyl-(C$_{2-10}$)alkenyl, or heterocyclyl-(C$_{2-10}$)alkynyl, any of which is optionally substituted with one or more independent halo, —CF$_3$, —OCF$_3$, —OR$^{77}$, —NR$^{77}$R$^{87}$, —C(O)R$^{77}$, —CO$_2$R$^{77}$, —CONR$^{77}$R$^{87}$, —NO$_2$, —CN, —S(O)$_{j5a}$R$^{77}$, —SO$_2$NR$^{77}$R$^{87}$, NR$^{77}$(C=O)R$^{87}$, NR$^{77}$(C=O)OR$^{87}$, NR$^{77}$(C=O)NR$^{78}$R$^{87}$, NR$^{77}$S(O)$_{j5a}$R$^{87}$, —(C=S)OR$^{77}$, —(C=O)SR$^{77}$, —NR$^{77}$(C=NR$^{87}$)NR$^{78}$R$^{88}$, —NR$^{77}$(C=NR$^{87}$)OR$^{78}$, —NR$^{77}$(C=NR$^{87}$)SR$^{78}$, —O(C=O)OR$^{77}$, —O(C=O)NR$^{77}$R$^{87}$, —O(C=O)SR$^{77}$, —S(C=O)OR$^{77}$, —P(O)OR$^{77}$OR$^{87}$, or —S(C=O)NR$^{77}$R$^{87}$ substituents; or aryl-(C$_{0-10}$)alkyl, aryl-(C$_{2-10}$)alkenyl, or aryl-(C$_{2-10}$)alkynyl, any of which is optionally substituted with one or more independent halo, —CF$_3$, —OCF$_3$, —OR$^{77}$, —NR$^{77}$R$^{87}$, —C(O)R$^{77}$, —CO$_2$R$^{77}$, —CONR$^{77}$R$^{87}$, —NO$_2$, —CN, —S(O)$_{j5a}$R$^{77}$, —SO$_2$NR$^{77}$R$^{87}$, NR$^{77}$(C=O)R$^{87}$, NR$^{77}$(C=O)OR$^{87}$, NR$^{77}$(C=O)NR$^{78}$R$^{87}$, NR$^{77}$S(O)$_{j5a}$R$^{87}$, —(C=S)OR$^{77}$, —(C=O)SR$^{77}$, —NR$^{77}$(C=NR$^{87}$)NR$^{78}$R$^{88}$, —NR$^{77}$(C=NR$^{87}$)OR$^{78}$, —NR$^{77}$(C=NR$^{87}$)SR$^{78}$, —O(C=O)OR$^{77}$, —O(C=O)NR$^{77}$R$^{87}$, —O(C=O)SR$^{77}$, —S(C=O)OR$^{77}$, —P(O)OR$^{77}$R$^{87}$, or —S(C=O)NR$^{77}$R$^{87}$ substituents; or hetaryl-(C$_{0-10}$)alkyl, hetaryl-(C$_{2-10}$)alkenyl, or hetaryl-(C$_{2-10}$)alkynyl, any of which is optionally substituted with one or more independent halo, —CF$_3$, —OCF$_3$, —OR$^{77}$, —NR$^{77}$R$^{87}$, —C(O)R$^{77}$, —CO$_2$R$^{77}$, —CONR$^{77}$R$^{87}$, —NO$_2$, —CN, —S(O)$_{j5a}$R$^{77}$, —SO$_2$NR$^{77}$R$^{87}$, NR$^{77}$(C=O)R$^{87}$, NR$^{77}$(C=O)OR$^{87}$, NR$^{77}$(C=O)NR$^{78}$R$^{87}$, NR$^{77}$S(O)$_{j5a}$R$^{87}$, —(C=S)OR$^{77}$, —(C=O)SR$^{77}$, —NR$^{77}$(C=NR$^{87}$)NR$^{78}$R$^{88}$, —NR$^{77}$(C=NR$^{87}$)OR$^{78}$, —NR$^{77}$(C=NR$^{87}$)SR$^{78}$, —O(C=O)OR$^{77}$, —O(C=O)NR$^{77}$R$^{87}$, —O(C=O)SR$^{77}$, —S(C=O)OR$^{77}$, —P(O)OR$^{77}$R$^{87}$, or —S(C=O)NR$^{77}$R$^{87}$ substituents; or R$^5$ with R$^6$ taken together with the respective carbon atom to which they are attached, form a 3-10 membered saturated or unsaturated ring, wherein said ring is optionally substituted with R$^{69}$; or R$^5$ with R$^6$ taken together with the respective carbon atom to which they are attached, form a 3-10 membered saturated or unsaturated heterocyclic ring, wherein said ring is optionally substituted with R$^{69}$;

R$^7$ and R$^8$ are each independently H, acyl, alkyl, alkenyl, aryl, heteroaryl, heterocyclyl or cycloalkyl, any of which is optionally substituted by one or more G$^{111}$ substituents;

R$^4$ is H, alkyl, alkenyl, alkynyl, aryl, heteroaryl, cycloalkyl, heterocyclyl, cycloalkenyl, or heterocycloalkenyl, any of which is optionally substituted by one or more G$^{41}$ substituents;

R$^{69}$ is equal to halo, —OR$^{78}$, —SH, —NR$^{78}$R$^{88}$, —CO$_2$R$^{78}$, —CONR$^{78}$R$^{88}$, —NO$_2$, —CN, —S(O)$_{j8}$R$^{78}$, —SO$_2$NR$^{78}$R$^{88}$, (C$_{0-10}$)alkyl, (C$_{2-10}$)alkenyl, (C$_{2-10}$)alkynyl, (C$_{1-10}$)alkoxy(C$_{1-10}$)alkyl, (C$_{1-10}$)alkoxy(C$_{2-10}$)alkenyl, (C$_{1-10}$)alkoxy(C$_{2-10}$)alkynyl, (C$_{1-10}$)alkylthio(C$_{1-10}$)alkyl, (C$_{1-10}$)alkylthio(C$_{2-10}$)alkenyl, (C$_{1-10}$)alkylthio(C$_{2-10}$)alkynyl, cyclo(C$_{3-8}$)alkyl, cyclo(C$_{3-8}$)alkenyl, cyclo(C$_{3-8}$)alkyl(C$_{1-10}$)alkyl, cyclo(C$_{3-8}$)alkenyl(C$_{1-10}$)alkyl, cyclo(C$_{3-8}$)alkyl(C$_{2-10}$)alkenyl, cyclo(C$_{3-8}$)alkenyl(C$_{2-10}$)alkenyl, cyclo(C$_{3-8}$)alkyl(C$_{2-10}$)alkynyl, cyclo(C$_{3-8}$)alkenyl(C$_{2-10}$)alkynyl, heterocyclyl-(C$_{0-10}$)alkyl, heterocyclyl-(C$_{2-10}$)alkenyl, or heterocyclyl-(C$_{2-10}$)alkynyl, any of which is optionally substituted with one or more independent halo, cyano, nitro, —OR$^{778}$, —SO$_2$NR$^{778}$R$^{888}$, or —NR$^{778}$R$^{888}$ substituents; or aryl-(C$_{0-10}$)alkyl, aryl-(C$_{2-10}$)alkenyl, or aryl-(C$_{2-10}$)alkynyl, any of which is optionally substituted with one or more independent halo, cyano, nitro, —OR$^{778}$, (C$_{1-10}$)alkyl, (C$_{2-10}$)alkenyl, (C$_{2-10}$)alkynyl, halo(C$_{1-10}$)alkyl, halo(C$_{2-10}$)alkenyl, halo(C$_{2-10}$)alkynyl, —COOH, (C$_{1-4}$)alkoxycarbonyl, —CONR$^{778}$R$^{888}$, —SO$_2$NR$^{778}$R$^{888}$, or —NR$^{778}$R$^{888}$ substituents; or hetaryl-(C$_{0-10}$)alkyl, hetaryl-(C$_{2-10}$)alkenyl, or hetaryl-(C$_{2-10}$)alkynyl, any of which is optionally substituted with one or more independent halo, cyano, nitro, —OR$^{778}$, (C$_{1-10}$)alkyl, (C$_{2-10}$)alkenyl, (C$_{2-10}$)alkynyl, halo(C$_{1-10}$)alkyl, halo(C$_{2-10}$)alkenyl, halo(C$_{2-10}$)alkynyl, —COOH, (C$_{1-4}$)alkoxycarbonyl, —CONR$^{778}$R$^{888}$, —SO$_2$NR$^{778}$R$^{888}$, or —NR$^{778}$R$^{888}$ substituents; or mono(C$_{1-6}$alkyl)amino(C$_{1-6}$)alkyl, di((C$_{1-6}$)alkyl)amino(C$_{1-6}$)alkyl, mono(aryl)amino(C$_{1-6}$)alkyl, di(aryl)amino(C$_{1-6}$)alkyl, or —N((C$_{1-6}$)alkyl)-(C$_{1-6}$)alkyl-aryl, any of which is optionally substituted with one or more independent halo, cyano, nitro, —OR$^{778}$, (C$_{1-10}$)alkyl, (C$_{2-10}$)alkenyl, (C$_{2-10}$)alkynyl, halo(C$_{1-10}$)alkyl, halo(C$_{2-10}$)alkenyl, halo(C$_{2-10}$)alkynyl, —COOH, (C$_{1-4}$)alkoxycarbonyl, —CONR$^{778}$R$^{888}$SO$_2$NR$^{778}$R$^{888}$, or —NR$^{778}$R$^{888}$ substituents; or in the case of —NR$^{78}$R$^{88}$, R$^{78}$ and R$^{88}$ taken together with the nitrogen atom to which they are attached form a 3-10 membered saturated ring, unsaturated ring, heterocyclic saturated ring, or heterocyclic unsaturated ring, wherein said ring is optionally substituted with one or more independent halo, cyano, hydroxy, nitro, $(C_{1-10})$ alkoxy, $-SO_2NR^{778}R^{888}$, or $-NR^{778}R^{888}$ substituents;

$R^{77}$, $R^{78}$, $R^{87}$, $R^{88}$, $R^{778}$, and $R^{888}$ are each independently $(C_{0-10})$alkyl, $(C_{2-10})$alkenyl, $(C_{2-10})$alkynyl, $(C_{1-10})$ alkoxy$(C_{1-10})$alkyl, $(C_{1-10})$alkoxy$C_{2-10}$)alkenyl, $(C_{1-10})$ alkoxy$(C_{2-10})$alkynyl, $(C_{1-10})$alkylthio$(C_{1-10})$alkyl, $(C_{1-10})$alkylthio$(C_{2-10})$alkenyl, $(C_{1-10})$alkylthio$(C_{2-10})$ alkynyl, cyclo$(C_{3-8})$alkyl, cyclo$(C_{3-8})$alkenyl, cyclo$(C_{3-8})$ alkyl$(C_{1-10})$alkyl, cyclo$(C_{3-8})$alkenyl$(C_{1-10})$alkyl, cyclo $(C_{3-8})$alkyl$(C_{2-10})$alkenyl, cyclo$(C_{3-8})$alkenyl$(C_{2-10})$ alkenyl, cyclo$(C_{3-8})$alkyl$(C_{2-10})$alkynyl, cyclo$(C_{3-8})$ alkenyl$(C_{2-10})$alkynyl, heterocyclyl-$(C_{0-10})$alkyl, heterocyclyl-$(C_{2-10})$alkenyl, heterocyclyl-$(C_{2-10})$alkynyl, $(C_{1-10})$alkylcarbonyl, $(C_{2-10})$alkenylcarbonyl, $(C_{2-10})$ alkynylcarbonyl, $(C_{1-10})$alkoxycarbonyl, $(C_{1-10})$alkoxycarbonyl$(C_{1-10})$alkyl, mono$(C_{1-6})$alkylaminocarbonyl, di$(C_{1-6})$alkylaminocarbonyl, mono(aryl)aminocarbonyl, di(aryl)aminocarbonyl, or $(C_{1-10})$alkyl(aryl)aminocarbonyl, any of which is optionally substituted with one or more independent halo, cyano, hydroxy, nitro, $(C_{1-10})$ alkoxy, $-SO_2N((C_{0-4})$alkyl$)((C_{0-4})$alkyl$)$, or $-N((C_{0-4})$ alkyl$)((C_{0-4})$alkyl$)$ substituents; or aryl-$(C_{0-10})$alkyl, aryl-$(C_{2-10})$alkenyl, or aryl-$(C_{2-10})$alkynyl, any of which is optionally substituted with one or more independent halo, cyano, nitro, $-O((C_{0-4})$alkyl$)$, $(C_{1-10})$alkyl, $(C_{2-10})$alkenyl, $(C_{2-10})$alkynyl, halo$(C_{1-10})$alkyl, halo$(C_{2-10})$alkenyl, halo$(C_{2-10})$alkynyl, $-COOH$, $(C_{1-4})$alkoxycarbonyl, $-CON((C_{0-4})$alkyl$)((C_{0-10})$alkyl$)$, $-SO_2N((C_{0-4})$alkyl$)$ $((C_{0-4})$alkyl$)$, or $-N((C_{0-4})$alkyl$)((C_{0-4})$alkyl$)$ substituents; or hetaryl-$(C_{0-10})$alkyl, hetaryl-$(C_{2-10})$alkenyl, or hetaryl-$(C_{2-10})$alkynyl, any of which is optionally substituted with one or more independent halo, cyano, nitro, $-O((C_{0-4})$alkyl$)$, $(C_{1-10})$alkyl, $(C_{2-10})$alkenyl, $(C_{2-10})$ alkynyl, halo$(C_{1-10})$alkyl, halo$(C_{2-10})$alkenyl, halo$(C_{2-10})$ alkynyl, $-COOH$, $(C_{1-4})$alkoxycarbonyl, $-CON((C_{0-4})$ alkyl$)((C_{0-4})$alkyl$)$, $-SO_2N((C_{0-4})$alkyl$)((C_{0-4})$alkyl$)$, or $-N((C_{0-4})$alkyl$)((C_{0-4})$alkyl$)$ substituents; or mono $((C_{1-6})$alkyl$)$amino$(C_{1-6})$alkyl, di$((C_{1-6})$alkyl$)$amino $(C_{1-6})$alkyl, mono(aryl)amino$(C_{1-6})$alkyl, di(aryl)amino $(C_{1-6})$alkyl, or $-N((C_{1-6})$alkyl$)$-$(C_{1-6})$alkyl-aryl, any of which is optionally substituted with one or more independent halo, cyano, nitro, $-O((C_{0-4})$alkyl$)$, $(C_{1-10})$alkyl, $(C_{2-10})$alkenyl, $(C_{2-10})$alkynyl, halo$(C_{1-10})$alkyl, halo $(C_{2-10})$alkenyl, halo$(C_{2-10})$alkynyl, $-COOH$, $(C_{1-4})$ alkoxycarbonyl, $-CON((C_{0-4})$alkyl$)((C_{0-4})$alkyl$)$, $-SO_2N((C_{0-4})$alkyl$)((C_{0-4})$alkyl$)$, or $-N((C_{0-4})$alkyl$)$ $((C_{0-4})$alkyl$)$ substituents; and n, m, j1, j1a, j2a, j3a, j4, j4a, j5a, j6a, j7, and j8 are each independently equal to 0, 1, or 2.

In an embodiment, the BTK inhibitor is a compound selected from the structures disclosed in U.S. Pat. Nos. 8,450,335 and 8,609,679, and U.S. Patent Application Publication Nos. 2010/0029610 A1, 2012/0077832 A1, 2013/0065879 A1, 2013/0072469 A1, and 2013/0165462 A1, the disclosures of which are incorporated by reference herein. In an embodiment, the BTK inhibitor is a compound of Formula (X) or Formula (XI):

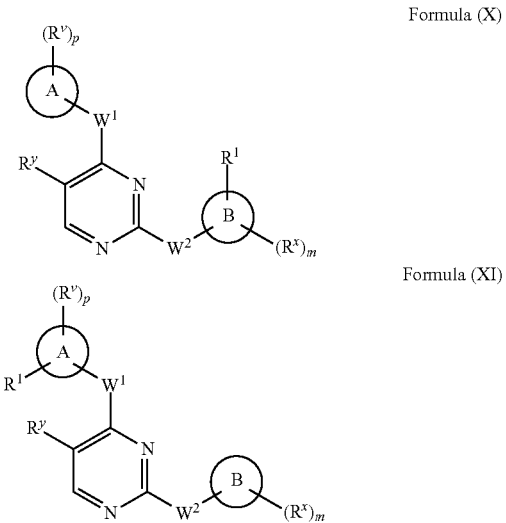

or a pharmaceutically acceptable salt, solvate, hydrate, cocrystal, or prodrug thereof, wherein:

Ring A is an optionally substituted group selected from phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur;

Ring B is an optionally substituted group selected from phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur;

$R^1$ is a warhead group;

$R^y$ is hydrogen, halogen, $-CN$, $-CF_3$, $C_{1-4}$ aliphatic, $C_{1-4}$ haloaliphatic, $-OR$, $-C(O)R$, or $-C(O)N(R)_2$;

each R group is independently hydrogen or an optionally substituted group selected from $C_{1-6}$ aliphatic, phenyl, a 4-7 membered heterocyclic ring having 1-2 heteroatoms independently selected from nitrogen, oxygen, or sulfur, or a 5-6 membered monocyclic heteroaryl ring having 1-4 heteroatoms independently selected from nitrogen, oxygen, or sulfur;

$W^1$ and $W^2$ are each independently a covalent bond or a bivalent $C_{1-3}$ alkylene chain wherein one methylene unit of $W^1$ or $W^2$ is optionally replaced by $-NR^2-$, $-N(R^2)$ $C(O)-$, $-C(O)N(R^2)-$, $-N(R^2)SO_2-$, $-SO_2N$ ($R^2$)—, —O—, —C(O)—, —OC(O)—, —C(O)O—, —S—, —SO— or —SO$_2$—;

$R^2$ is hydrogen, optionally substituted C$_{1-6}$ aliphatic, or —C(O)R, or:

$R^2$ and a substituent on Ring A are taken together with their intervening atoms to form a 4-6 membered saturated, partially unsaturated, or aromatic fused ring, or:

$R^2$ and $R^y$ are taken together with their intervening atoms to form a 4-7 membered partially unsaturated or aromatic fused ring;

m and p are independently 0-4; and $R^x$ and $R^v$ are independently selected from —R, halogen, —OR, —O(CH$_2$)$_q$OR, —CN, —NO$_2$, —SO$_2$R, —SO$_2$N(R)$_2$, —SOR, —C(O)R, —CO$_2$R, —C(O)N(R)$_2$, —NRC(O)R, —NRC(O)NR$_2$, —NRSO$_2$R, or —N(R)$_2$, wherein q is 1-4; or:

$R^x$ and $R^1$ when concurrently present on Ring B are taken together with their intervening atoms to form a 5-7 membered saturated, partially unsaturated, or aryl ring having 0-3 heteroatoms independently selected from nitrogen, oxygen, or sulfur, wherein said ring is substituted with a warhead group and 0-3 groups independently selected from oxo, halogen, —CN, or C$_{1-6}$ aliphatic; or $R^v$ and $R^1$ when concurrently present on Ring A are taken together with their intervening atoms to form a 5-7 membered saturated, partially unsaturated, or aryl ring having 0-3 heteroatoms independently selected from nitrogen, oxygen, or sulfur, wherein said ring is substituted with a warhead group and 0-3 groups independently selected from oxo, halogen, —CN, or C$_{1-6}$ aliphatic.

In an embodiment, the BTK inhibitor is a compound of Formula (X) or Formula (XI), wherein:

Ring A is an optionally substituted group selected from phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur;

Ring B is an optionally substituted group selected from phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur;

$R^1$ is -L-Y, wherein:

L is a covalent bond or a bivalent C$_{1-8}$ saturated or unsaturated, straight or branched, hydrocarbon chain, wherein one, two, or three methylene units of L are optionally and independently replaced by cyclopropylene, —NR—, —N(R)C(O)—, —C(O)N(R)—, —N(R)SO$_2$—, —SO$_2$N(R)—, —O—, —C(O)—, —OC(O)—, —C(O)O—, —S—, —SO—, —SO$_2$—, —C(=S)—, —C(=NR)—, —N=N—, or —C(=N$_2$)—;

Y is hydrogen, C$_{1-6}$ aliphatic optionally substituted with oxo, halogen, or CN, or a 3-10 membered monocyclic or bicyclic, saturated, partially unsaturated, or aryl ring having 0-3 heteroatoms independently selected from nitrogen, oxygen, or sulfur, and wherein said ring is substituted with at 1-4 groups independently selected from -Q-Z, oxo, NO$_2$, halogen, CN, or C$_{1-6}$ aliphatic, wherein:

Q is a covalent bond or a bivalent C$_{1-6}$ saturated or unsaturated, straight or branched, hydrocarbon chain, wherein one or two methylene units of Q are optionally and independently replaced by —NR—, —S—, —O—, —C(O)—, —SO—, or —SO$_2$—; and Z is hydrogen or C$_{1-6}$ aliphatic optionally substituted with oxo, halogen, or CN;

$R^y$ is hydrogen, halogen, —CN, —CF$_3$, C$_{1-4}$ aliphatic, C$_{1-4}$ haloaliphatic, —OR, —C(O)R, or —C(O)N(R)$_2$;

each R group is independently hydrogen or an optionally substituted group selected from C$_{1-6}$ aliphatic, phenyl, a 4-7 membered heterocyclic ring having 1-2 heteroatoms independently selected from nitrogen, oxygen, or sulfur, or a 5-6 membered monocyclic heteroaryl ring having 1-4 heteroatoms independently selected from nitrogen, oxygen, or sulfur;

$W^1$ and $W^2$ are each independently a covalent bond or a bivalent C$_{1-3}$ alkylene chain wherein one methylene unit of $W^1$ or $W^2$ is optionally replaced by —NR$^2$—, —N(R$^2$)C(O)—, —C(O)N(R$^2$)—, —N(R$^2$)SO$_2$—, —SO$_2$N(R$^2$)—, —O—, —C(O)—, —OC(O)—, —C(O)O—, —S—, —SO— or —SO$_2$—;

$R^2$ is hydrogen, optionally substituted C$_{1-6}$ aliphatic, or —C(O)R, or:

$R^2$ and a substituent on Ring A are taken together with their intervening atoms to form a 4-6 membered partially unsaturated or aromatic fused ring; or $R^2$ and $R^y$ are taken together with their intervening atoms to form a 4-6 membered saturated, partially unsaturated, or aromatic fused ring;

m and p are independently 0-4; and $R^x$ and $R^v$ are independently selected from —R, halogen, —OR, —O(CH$_2$)$_q$OR, —CN, —NO$_2$, —SO$_2$R, —SO$_2$N(R)$_2$, —SOR, —C(O)R, —CO$_2$R, —C(O)N(R)$_2$, —NRC(O)R, —NRC(O)NR$_2$, —NRSO$_2$R, or —(R)$_2$, or:

$R^x$ and $R^1$ when concurrently present on Ring B are taken together with their intervening atoms to form a 5-7 membered saturated, partially unsaturated, or aryl ring having 0-3 heteroatoms independently selected from nitrogen, oxygen, or sulfur, wherein said ring is substituted with a warhead group and 0-3 groups independently selected from oxo, halogen, —CN, or C$_{1-6}$ aliphatic; or $R^v$ and $R^1$ when concurrently present on Ring A are taken together with their intervening atoms to form a 5-7 membered saturated, partially unsaturated, or aryl ring having 0-3 heteroatoms independently selected from nitrogen, oxygen, or sulfur, wherein said ring is substituted with a warhead group and 0-3 groups independently selected from oxo, halogen, —CN, or C$_{1-6}$ aliphatic.

As defined generally above, Ring A is an optionally substituted group selected from phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur. In certain embodiments, Ring A is an optionally substituted phenyl group. In some embodiments, Ring A is an optionally substituted naphthyl ring or a bicyclic 8-10 membered heteroaryl ring having 1-4 heteroatoms independently selected from nitrogen, oxygen, or sulfur. In certain other embodiments, Ring A is an optionally substituted 3-7 membered carbocyclic ring. In other embodiments, Ring A is an optionally substituted 4-7 membered heterocyclic ring having 1-3 heteroatoms independently selected from nitrogen, oxygen, or sulfur.

In certain embodiments, Ring A is substituted as defined herein. In some embodiments, Ring A is substituted with one, two, or three groups independently selected from halogen, $R^o$, or —$(CH_2)_{0-4}OR^o$, or —$O(CH_2)_{0-4}R^o$, wherein each $R^o$ is as defined herein. Exemplary substituents on Ring A include Br, I, Cl, methyl, —$CF_3$, —C≡CH, —$OCH_2$phenyl, —$OCH_2$(fluorophenyl), or —$OCH_2$pyridyl.

In an embodiment, the BTK inhibitor is a compound of Formula (XII), also known as CC-292 (Celgene):

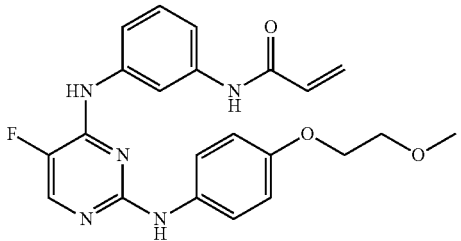

Formula (XII)

or a pharmaceutically acceptable salt, solvate, hydrate, cocrystal, or prodrug thereof, or a besylate salt thereof. The preparation of this compound is described in U.S. Patent Application Publication No. 2010/0029610 A1 at Example 20. The preparation of the besylate salt of this compound is described in U.S. Patent Application Publication No. 2012/0077832 A1. In an embodiment, the BTK inhibitor is a compound selected from the structures disclosed in U.S. Patent Application Publication No. 2010/0029610 A1 or No. 2012/0077832 A1, the disclosures of which are incorporated by reference herein.

In an embodiment, the BTK inhibitor is N-(3-((5-fluoro-2-((4-(2-methoxyethoxy)phenyl)amino)pyrimidin-4-yl)amino)phenyl)acrylamide or a pharmaceutically acceptable salt, solvate, hydrate, cocrystal, or prodrug thereof, or a hydrochloride salt thereof. The preparation of this compound is described in U.S. Patent Application Publication No. 2012/0077832 A1.

In an embodiment, the BTK inhibitor is (N-(3-(5-fluoro-2-(4-(2-methoxyethoxy)phenylamino)pyrimidin-4-ylamino) phenyl)acrylamide), or a pharmaceutically acceptable salt, solvate, hydrate, cocrystal, or prodrug thereof, or a besylate salt thereof. The preparation of this compound is described in U.S. Patent Application Publication No. 2010/0029610 A1 at Example 20. The preparation of its besylate salt is described in U.S. Patent Application Publication No. 2012/0077832 A1.

In an embodiment, the BTK inhibitor is a compound of Formula (XIII):

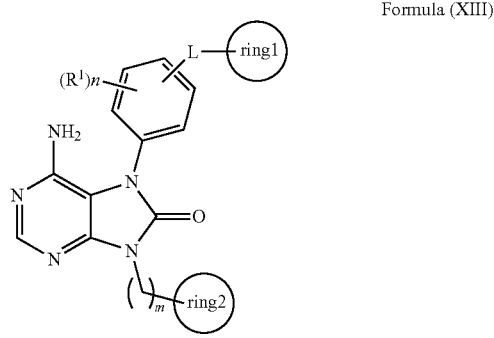

Formula (XIII)

or a pharmaceutically acceptable salt, hydrate, solvate, cocrystal, or prodrug thereof, wherein L represents (1) —O—, (2) —S—, (3) —SO—, (4) —$SO_2$— (5) —NH—, (6) —C(O)—, (7) —$CH_2O$—, (8) —O—$CH_2$—, (9) —$CH_2$—, or (10) —CH(OH)—;

$R^1$ represents (1) a halogen atom, (2) a $C_{1-4}$ alkyl group, (3) a $C_{1-4}$ alkoxy group, (4) a $C_{1-4}$ haloalkyl group, or (5) a $C_{1-4}$ haloalkoxy group;

ring1 represents a 4- to 7-membered cyclic group, which may be substituted by from one to five substituents each independently selected from the group consisting of (1) halogen atoms, (2) $C_{1-4}$ alkyl groups, (3) $C_{1-4}$ alkoxy groups, (4) nitrile, (5) $C_{1-4}$ haloalkyl groups, and (6) $C_{1-4}$ haloalkoxy groups, wherein when two or more substituents are present on ring1, these substituents may form a 4- to 7-membered cyclic group together with the atoms in ring1 to which these substituents are bound;

ring2 represents a 4- to 7-membered saturated heterocycle, which may be substituted by from one to three —K—R;

K represents (1) a bond, (2) a $C_{1-4}$ alkylene, (3) —C(O)—, (4) —C(O)—$CH_2$—, (5) —$CH_2$—C(O)—, (6) —C(O)O—, or (7) —$SO_2$— (wherein the bond on the left is bound to the ring2);

$R^2$ represents (1) a $C_{1-4}$ alkyl, (2) a $C_{2-4}$ alkenyl, or (3) a $C_{2-4}$ alkynyl group, each of which may be substituted by from one to five substituents each independently selected from the group consisting of (1) $NR^3R^4$, (2) halogen atoms, (3) $CONR^5R^6$, (4) $CO_2R^7$, and (5) $OR^8$;

$R^3$ and $R^4$ each independently represent (1) a hydrogen atom, or (2) a $C_{1-4}$ alkyl group which may be substituted by $OR^9$ or $CONR^{10}R^{11}$; $R^3$ and $R^4$ may, together with the nitrogen atom to which they are bound, form a 4- to 7-membered nitrogenous saturated heterocycle, which may be substituted by an oxo group or a hydroxyl group;

$R^5$ and $R^6$ each independently represent (1) a hydrogen atom, (2) a $C_{1-4}$ alkyl group, or (3) a phenyl group;

$R^7$ represents (1) a hydrogen atom or (2) a $C_{1-4}$ alkyl group;

$R^8$ represents (1) a hydrogen atom, (2) a $C_{1-4}$ alkyl group, (3) a phenyl group, or (4) a benzotriazolyl group; $R^9$ represents (1) a hydrogen atom or (2) a $C_{1-4}$ alkyl group;

$R^{10}$ and $R^{11}$ each independently represent (1) a hydrogen atom or (2) a $C_{1-4}$ alkyl group;

n represents an integer from 0 to 4;

m represents an integer from 0 to 2; and when n is two or more, the $R^1$'s may be the same as each other or may differ from one another).

In an embodiment, the BTK inhibitor is a compound of Formula (XIV):

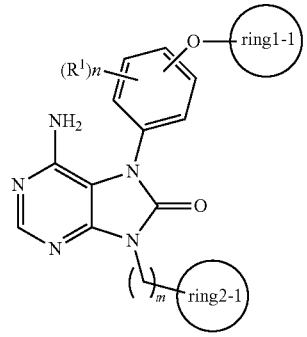

Formula (XIV)

or a pharmaceutically acceptable salt, hydrate, solvate, cocrystal, or prodrug thereof, wherein $R^1$ represents (1) a halogen atom, (2) a $C_{1-4}$ alkyl group, (3) a $C_{1-4}$ alkoxy group, (4) a $C_{1-4}$ haloalkyl group, or (5) a $C_{1-4}$ haloalkoxy group;

ring1 represents a benzene, cyclohexane, or pyridine ring, each of which may be substituted by from one to five substituents each independently selected from the group consisting of (1) halogen atoms, (2) $C_{1-4}$ alkyl groups, (3) $C_{1-4}$ alkoxy groups, (4) nitrile, (5) $CF_3$;

ring2 represents a 4- to 7-membered nitrogenous saturated heterocycle, which may be substituted by from one to three —K—$R^2$; wherein K represents (1) a bond, (2) a $C_{1-4}$ alkylene, (3) —C(O)—, (4) —C(O)CH$_2$—, (5) —CH$_2$—C(O)—, (6) —C(O)O—, or (7) —SO$_2$— (wherein the bond on the left is bound to the ring2);

$R^2$ represents (1) a $C_{1-4}$ alkyl, (2) a $C_{2-4}$ alkenyl, or (3) a $C_{2-4}$ alkynyl group, each of which may be substituted by from one to five substituents each independently selected from the group consisting of (1) $NR^3R^4$, (2) halogen atoms, (3) $CONR^5R^6$, (4) $CO_2R^7$, and (5) $OR^8$;

$R^3$ and $R^4$ each independently represent (1) a hydrogen atom, or (2) a $C_{1-4}$ alkyl group which may be substituted by $OR^9$ or $CONR^{10}R^{11}$; $R^3$ and $R^4$ may, together with the nitrogen atom to which they are bound, form a 4- to 7-membered nitrogenous saturated heterocycle, which may be substituted by an oxo group or a hydroxyl group;

$R^5$ and $R^6$ each independently represent (1) a hydrogen atom, (2) a $C_{1-4}$ alkyl group, or (3) a phenyl group;

$R^7$ represents (1) a hydrogen atom or (2) a $C_{1-4}$ alkyl group;

$R^8$ represents (1) a hydrogen atom, (2) a $C_{1-4}$ alkyl group, (3) a phenyl group, or (4) a benzotriazolyl group; $R^9$ represents (1) a hydrogen atom or (2) a $C_{1-4}$ alkyl group;

$R^{10}$ and $R^{11}$ each independently represent (1) a hydrogen atom or (2) a $C_{1-4}$ alkyl group;

n represents an integer from 0 to 4;

m represents an integer from 0 to 2; and when n is two or more, the $R^1$'s may be the same as each other or may differ from one another).

In an embodiment, the BTK inhibitor is a compound of Formula (XV):

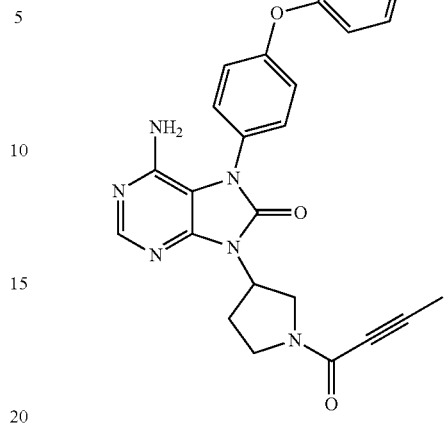

Formula (XV)

or a pharmaceutically acceptable salt, solvate, hydrate, cocrystal, or prodrug thereof, or a hydrochloride salt thereof. The preparation of this compound is described in International Patent Application Publication No. WO 2013/081016 A1. In an embodiment, the BTK inhibitor is 6-amino-9-(1-(but-2-ynoyl)pyrrolidin-3-yl)-7-(4-phenoxyphenyl)-7,9-dihydro-8H-purin-8-one or a pharmaceutically acceptable salt, solvate, hydrate, cocrystal, or prodrug thereof, or a hydrochloride salt thereof. In an embodiment, the BTK inhibitor is 6-amino-9-[(3S)-1-(2-butynoyl)-3-pyrrolidinyl]-7-(4-phenoxyphenyl)-7,9-dihydro-8H-purin-8-one or a pharmaceutically acceptable salt, solvate, hydrate, cocrystal, or prodrug thereof, or a hydrochloride salt thereof.

The R-enantiomer of Formula (XV) is also known as ONO-4059, and is given by Formula (XVI):

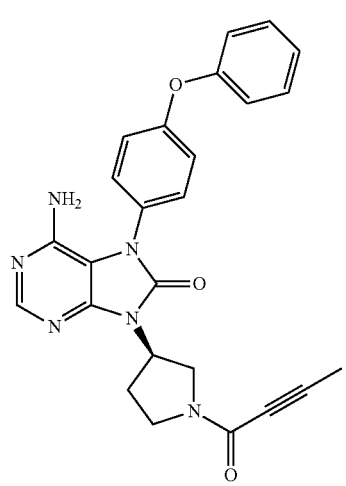

Formula (XVI)

or a pharmaceutically acceptable salt, solvate, hydrate, cocrystal, or prodrug thereof, or a hydrochloride salt thereof.

In an embodiment, the BTK inhibitor is 6-amino-9-[(3R)-1-(2-butynoyl)-3-pyrrolidinyl]-7-(4-phenoxyphenyl)-7,9-dihydro-8H-purin-8-one or a pharmaceutically acceptable salt, solvate, hydrate, cocrystal, or prodrug thereof, or a hydrochloride salt thereof.

The preparation of Formula (XVI) is described in International Patent Application Publication No. WO 2013/

081016 A1. In brief, the BTK inhibitor of Formula (XVI) can be prepared by the following procedure.

Step 1: A solution of dibenzylamine (10.2 g) in dichloromethane (30 mL) is dripped into a solution of 4,6-dichloro-5-nitropyrimidine (10 g) in dichloromethane (70 mL) on an ice bath. Then triethylamine (14.4 mL) is added, and the mixture is stirred for 1 hour. Water is added to the reaction mixture, the organic layer is washed with a saturated aqueous sodium chloride solution and dried over anhydrous sodium sulfate, and the solvent is concentrated under reduced pressure to obtain N,N-dibenzyl-6-chloro-5-nitropyrimidine-4-amine (19.2 g).

Step 2: The compound prepared in Step 1 (19 g) and tert-butyl (3R)-3-aminopyrrolidine-1-carboxylate (10.5 g) are dissolved in dioxane (58 mL). Triethylamine (8.1 mL) is added, and the mixture is stirred for 5 hours at 50° C. The reaction mixture is returned to room temperature, the solvent is distilled off, water is added, and extraction is performed with ethyl acetate. The organic layer is washed with saturated aqueous sodium chloride solution, then dried over anhydrous sodium sulfate, and the solvent is distilled off. The residue is purified by silica gel column chromatography to obtain tert-butyl (3R)-3-{[6-(dibenzylamino)-5-nitropyrimidin-4-yl]amino}pyrrolidine-1-carboxylate (27.0 g).

Step 3: An ethyl acetate (360 mL) solution of the compound prepared in Step 2 (17.5 g) is dripped into a mixture of zinc (23.3 g) and a 3.0 M aqueous ammonium chloride solution (11.4 g) on an ice bath, and the temperature is immediately raised to room temperature. After stirring for 2 hours, the reaction mixture is filtered through CELITE and the solvent is distilled off. The residue is purified by silica gel column chromatography to obtain tert-butyl (3R)-3-{[5-amino-6-(dibenzylamino)pyrimidin-4-yl]amino}pyrrolidine-1-carboxylate (12.4 g).

Step 4: The compound prepared in Step 3 (8.4 g) and 1,1'-carbonyl diimidazole (5.9 g) are dissolved in tetrahydrofuran (120 mL) and the solution is stirred for 15 hours at 60° C. The solvent is distilled off from the reaction mixture, water is added, and extraction with ethyl acetate is performed. The organic layer is washed with saturated aqueous sodium chloride solution, dried over anhydrous sodium sulfate, and the solvent is distilled off. The residue is purified by silica gel column chromatography to obtain tert-butyl (3R)-3-[6-(dibenzylamino)-8-oxo-7,8-dihydro-9H-purin-9-yl]pyrrolidin-1-carboxylate (7.8 g).

Step 5: The compound prepared in Step 4 (7.8 g) is dissolved in methanol (240 mL) and ethyl acetate (50 mL), 20% Pearlman's catalyst (Pd(OH)$_2$/C) (8.0 g, 100 wt %) is added, hydrogen gas replacement is carried out, and stirring is performed for 7.5 hours at 60° C. The reaction mixture is filtered through CELITE and the solvent is distilled off to obtain tert-butyl (3R)-3-(6-amino-8-oxo-7,8-dihydro-9H-purin-9-yl)pyrrolidine-1-carboxylate (5.0 g).

Step 6: At room temperature p-phenoxy phenyl boronic acid (2.1 g), copper(II) acetate (1.48 g), molecular sieve 4A (2.5 g), and pyridine (0.82 mL) are added to a dichloromethane suspension (200 mL) of the compound prepared in Step 5 (2.5 g), followed by stirring for 21 hours. The reaction mixture is filtered through CELITE and the residue is purified by silica gel column chromatography to obtain tert-butyl (3R)-3-[6-amino-8-oxo-7-(4-phenoxyphenyl)-7,8-dihydro-9H-purin-9-yl]pyrrolidine-1-carboxylate (1.3 g).

Step 7: At room temperature 4 N HCl/dioxane (13 mL) is added to a methanol (13 mL) suspension of the compound prepared in Step 6 (1.3 g 2.76 mmol, 1.0 equivalent), and the mixture is stirred for 1 hour. The solvent is then distilled off to obtain (3R)-6-amino-9-pyrrolidin-3-yl-7-(4-phenoxyphenyl)-7,9-dihydro-8H-purin-8-one dihydrochloride (1.5 g).

Step 8: After 2-butynoic acid (34 mg), 1-ethyl-3-(3-dimethylaminopropyl) carbodiimide hydrochloride (EDC) (78 mg), 1-hydroxybenzotriazole (HOBt) (62 mg), and triethylamine (114 mL) are added to a solution of the compound prepared in Step 7 (100 mg) in dimethyl formamide (3 mL), the mixture is stirred at room temperature for 3 hours. Water is added to the reaction mixture and extraction with ethyl acetate is performed. The organic layer is washed with saturated sodium carbonate solution and saturated aqueous sodium chloride solution, then dried over anhydrous sodium sulfate, and the solvent is distilled off. The residue is purified by thin layer chromatography (dichloromethane:methanol:28% ammonia water=90:10:1) to obtain 6-amino-9-[(3R)-1-(2-butynoyl)-3-pyrrolidinyl]-7-(4-phenoxyphenyl)-7,9-dihydro-8H-purin-8-one (Formula (XVI)) (75 mg).

The hydrochloride salt of the compound of Formula (XVI) can be prepared as follows: 6-amino-9-[(3R)-1-(2-butynoyl)-3-pyrrolidinyl]-7-(4-phenoxyphenyl)-7,9-dihydro-8H-purin-8-one (3.0 g) (which may be prepared as described above) is placed in a 300 mL 3-neck pear-shaped flask, ethyl acetate (30 mL) and 1-propanol (4.5 mL) are added, and the external temperature is set at 70° C. (internal temperature 61° C.). After it is confirmed that the compound prepared in Step 8 has dissolved completely, 10% HCl/methanol (3.5 mL) is added, and after precipitation of crystals is confirmed, the crystals are ripened by the following sequence: external temperature 70° C. for 30 min, external temperature 60° C. for 30 min, external temperature 50° C. for 60 min, external temperature 40° C. for 30 min, room temperature for 30 min, and an ice bath for 30 min. The resulting crystals are filtered, washed with ethyl acetate (6 mL), and dried under vacuum at 50° C. to obtain white crystals of 6-amino-9-[(3R)-1-(2-butynoyl)-3-pyrrolidinyl]-7-(4-phenoxyphenyl)-7,9-dihydro-8H-purin-8-one hydrochloride (2.76 g).

In an embodiment, the BTK inhibitor is a compound selected from the structures disclosed in U.S. Patent Application Publication No. US 2014/0330015 A1, the disclosure of which is incorporated by reference herein.

In an embodiment, the BTK inhibitor is a compound of Formula (XVII):

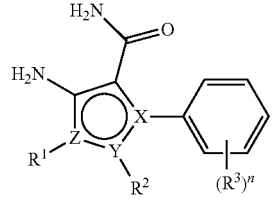

Formula (XVII)

or a pharmaceutically acceptable salt, solvate, hydrate, cocrystal, or prodrug thereof, or a hydrochloride salt thereof, wherein:

X—Y—Z is N—C—C and $R^2$ is present, or C—N—N and $R^2$ is absent;

$R^1$ is a 3-8 membered, N-containing ring, wherein the N is unsubstituted or substituted with $R^4$;

$R^2$ is H or lower alkyl, particularly methyl, ethyl, propyl or butyl; or $R^1$ and $R^2$ together with the atoms to which they are attached, form a 4-8 membered ring, preferably a 5-6 membered ring, selected from cycloalkyl, saturated or unsaturated heterocycle, aryl, and heteroaryl rings unsubstituted or substituted with at least one substituent L-$R^4$;

$R^3$ is in each instance, independently halogen, alkyl, S-alkyl, CN, or $OR^5$;

n is 1, 2, 3, or 4, preferably 1 or 2;

L is a bond, NH, heteroalkyl, or heterocyclyl;

$R^4$ is COR', $CO_2R'$, or $SO_2R'$, wherein R' is substituted or unsubstituted alkyl, substituted or unsubstituted alkenyl, substituted or unsubstituted alkynyl;

$R^5$ is H or unsubstituted or substituted heteroalkyl, alkyl, cycloalkyl, saturated or unsaturated heterocyclyl, aryl, or heteroaryl.

In some embodiments, the BTK inhibitor is one of the following particular embodiments of Formula (XVII):

X—Y—Z is C—N—N and $R^2$ is absent; and $R^1$ is 3-8 membered, N-containing ring, N-substituted with $R^4$;

X—Y—Z is N—C—C and $R^2$ is present, $R^1$ is 3-8 membered, N-containing ring, N-substituted with $R^4$; and $R^2$ is H or lower alkyl;

X—Y—Z is N—C—C and $R^2$ is present; and $R^1$ and $R^2$ together with the atoms to which they are attached, form a 4-8 membered ring selected from cycloalkyl, saturated or unsaturated heterocycle, aryl, and heteroaryl rings unsubstituted or substituted with at least one substituent L-$R^4$, wherein preferred rings of $R^1$ and $R^2$ are 5-6-membered, particularly dihydropyrrole, tetrahydropyridine, tetrahydroazepine, phenyl, or pyridine;

X—Y—Z is N—C—C and $R^2$ is present; and $R^1$ and $R^2$ together with the atoms to which they are attached, form a 5-6 membered ring, preferably (a) phenyl substituted with a single -L-$R^4$, or (b) dihydropyrrole or tetrahydropyridine, N-substituted with a single -L-$R^4$ wherein L is bond;

$R^1$ is piperidine or azaspiro[3.3]heptane, preferably N-substituted with $R^4$;

$R^4$ is COR' or $SO_2R'$, particularly wherein R' is substituted or unsubstituted alkenyl, particularly substituted or unsubstituted ethenyl; or $R^5$ is unsubstituted or substituted alkyl or aryl, particularly substituted or unsubstituted phenyl or methyl, such as cyclopropyl-substituted methyl with or tetrabutyl-substituted phenyl.

In some embodiments, the BTK inhibitor is one of the following particular embodiments of Formula (XVII):

$R^1$ is piperidine or azaspiro[3.3]heptane, N-substituted with $R^4$, wherein $R^4$ is H, COR' or $SO_2R'$, and R' is substituted or unsubstituted alkenyl, particularly substituted or unsubstituted ethenyl;

$R^3$ is —$OR^5$, $R^5$ is phenyl, and n is 1;

$R^1$ and $R^2$, together with the atoms to which they are attached, form a 5-6 membered ring, preferably (a) phenyl substituted with a single -L-$R^4$, or (b) dihydropyrrole or tetrahydropyridine, N-substituted with a single -L-$R^4$ wherein L is bond; $R^3$ is —$OR^5$; n is 1; $R^4$ is COR', and R' is ethenyl; and $R^5$ is phenyl; and X—Y—Z is C—N—N and $R^2$ is absent; $R^1$ is piperidine, N-substituted with $R^4$; $R^3$ is —$OR^5$; n is 1; $R^4$ is COR', and R' is unsubstituted or substituted alkenyl, particularly ethenyl; and $R^5$ is substituted or unsubstituted aryl, particularly phenyl.

In an embodiment, the BTK inhibitor is a compound of Formula (XVIII), Formula (XIX), or Formula (XX):

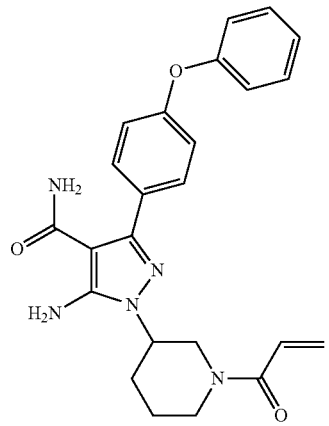

Formula (XVIII)

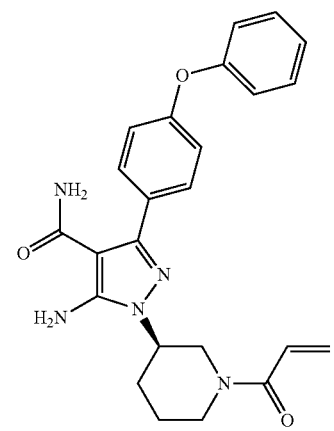

Formula (XIX)

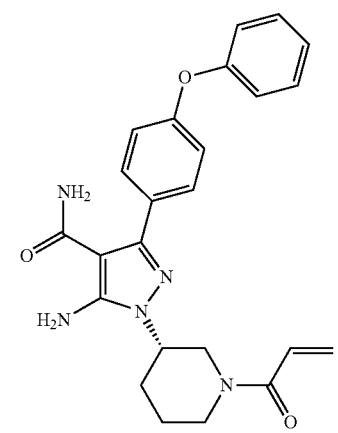

Formula (XX)

or a pharmaceutically acceptable salt, solvate, hydrate, cocrystal, or prodrug thereof, or a hydrochloride salt thereof. Formula (XIX) is also known as BGB-3111. The preparation of these compounds is described in International Patent Application Publication No. WO 2014/173289 A1 and U.S. Patent Application Publication No. US 2015/0005277 A1.

In brief, the BTK inhibitor of Formula (XVIII) can be prepared by the following procedure.

Step 1. Preparation of 2-(hydroxy(4-phenoxyphenyl)methylene)malononitrile

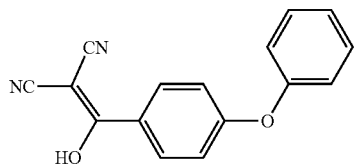 [SMILES: N#CC(C#N)=C(O)c1ccc(Oc2ccccc2)cc1]

A solution of 4-phenoxybenzoic acid (300 g, 1.4 mol) in SOCl$_2$ (1.2 L) is stirred at 80° C. under N$_2$ for 3 hours. The mixture is concentrated in vacuum to give the intermediate (315 g) which is used for next step without further purification.

To a solution of propanedinitrile (89.5 g, 1355 mmol) and DIEA (350 g, 2710 mmol) in THF (800 mL) is added dropwise a solution of the intermediate (315 g) in toluene (800 mL) at 0-5° C. over 2 hours. The resultant mixture is allowed to warm to RT and stirred for 16 hours. The reaction is quenched with water (2.0 L) and extracted with of EA (2.0 L×3). The combined organic layers are washed with 1000 mL of 3 N HCl aqueous solution, brine (2.0 L×3), dried over Na$_2$SO$_4$ and concentrated to give the crude product (330 g, 93%).

Step 2. Preparation of 2-(Methoxy(4-phenoxyphenyl)methylene)malononitrile

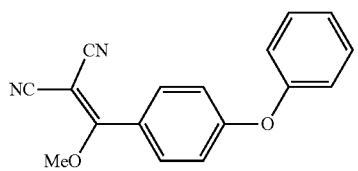 [SMILES: COC(=C(C#N)C#N)c1ccc(Oc2ccccc2)cc1]

A solution of 2-(hydroxy(4-phenoxyphenyl)methylene)malononitrile (50 g, 190.8 mmol) in CH(OMe)$_3$ (500 mL) is heated to 75° C. for 16 hours. Then the mixture is concentrated to a residue and washed with MeOH (50 mL) to give 25 g (47.5%) of 2-(methoxy(4-phenoxyphenyl)methylene)malononitrile as a yellow solid.

Step 3. Preparation of 5-amino-3-(4-phenoxyphenyl)-1H-pyrazole-4-carbonitrile

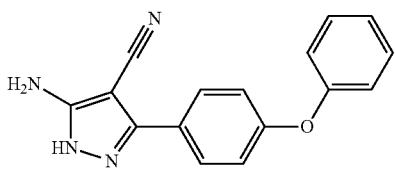 [SMILES: N#Cc1c(-c2ccc(Oc3ccccc3)cc2)n[nH]c1N]

To a solution of 2-(methoxy(4-phenoxyphenyl)methylene)malononitrile (80 g, 290 mmol) in ethanol (200 mL) is added hydrazine hydrate (20 mL). The mixture is stirred at RT for 16 hours then is concentrated to give the crude product and washed with MeOH (30 mL) to afford 55 g (68.8%) of 5-amino-3-(4-phenoxyphenyl)-1H-pyrazole-4-carbonitrile as an off-white solid.

Step 4. Preparation of tert-butyl 3-(tosyloxy)piperidine-1-carboxylate

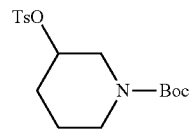 [SMILES: Cc1ccc(S(=O)(=O)OC2CCCN(C(=O)OC(C)(C)C)C2)cc1]

To a solution of tert-butyl 3-hydroxypiperidine-1-carboxylate (1.05 g, 5.0 mmol) in pyridine (8 mL) is added TsCl (1.425 g, 7.5 mmol). The mixture is stirred at RT under N$_2$ for two days. The mixture is concentrated and partitioned between 100 mL of EA and 100 mL of HCl (1 N) aqueous solution. The organic layer is separated from aqueous layer, washed with saturated NaHCO$_3$ aqueous solution (100 mL×2), brine (100 mL×3) and dried over Na$_2$SO$_4$. The organic layer is concentrated to afford 1.1 g (60%) of tert-butyl 3-(tosyloxy)piperidine-1-carboxylate as a colorless oil.

Step 5. Preparation of tert-butyl 3-(5-amino-4-cyano-3-(4-phenoxyphenyl)-1H-pyrazol-1-yl)piperidine-1-carboxylate

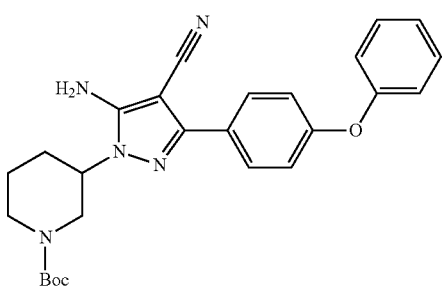 [SMILES: CC(C)(C)OC(=O)N1CCCC(n2nc(-c3ccc(Oc4ccccc4)cc3)c(C#N)c2N)C1]

To a solution of tert-butyl 3-(tosyloxy)piperidine-1-carboxylate (355 mg, 1.0 mmol) and 5-amino-3-(4-phenoxyphenyl)-1H-pyrazole-4-carbonitrile (276 mg, 1.0 mmol) in 5 mL of DMF is added Cs$_2$CO$_3$ (650 mg, 2.0 mmol). The mixture is stirred at RT for 16 hours, 75° C. for 3 hours and 60° C. for 16 hours. The mixture is concentrated washed with brine (100 mL×3) and dried over Na$_2$SO$_4$. The material is concentrated and purified by chromatography column on silica gel (eluted with petroleum ether/ethyl actate=3/1) to afford 60 mg (13%) of tert-butyl 3-(5-amino-4-cyano-3-(4-phenoxyphenyl)-1H-pyrazol-1-yl)piperidine-1-carboxylate as a yellow oil.

Step 6. Preparation of tert-butyl 3-(5-amino-4-carbamoyl-3-(4-phenoxyphenyl)-1H-pyrazol-1-yl)piperidine-1-carboxylate

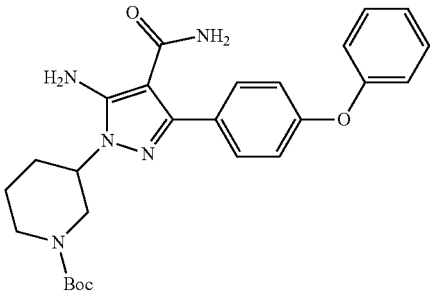 [SMILES: CC(C)(C)OC(=O)N1CCCC(n2nc(-c3ccc(Oc4ccccc4)cc3)c(C(N)=O)c2N)C1]

To a solution of tert-butyl 3-(5-amino-4-cyano-3-(4-phenoxyphenyl)-1H-pyrazol-1-yl)piperidine-1-carboxylate (100 mg, 0.22 mmol) in DMSO (2 mL) and ethanol (2 mL) was added the solution of NaOH (200 mg, 5 mmol) in water (1 mL) and H$_2$O$_2$ (1 mL). The mixture is stirred at 60° C. for 15 min and concentrated to remove EtOH, after which 10 mL of water and 50 mL of ethyl acetate are added. The organic layer is separated from aqueous layer, washed with brine (30 mL×3) and dried over Na$_2$SO$_4$. After concentration, 50 mg of residue is used directly in the next step, wherein 50 mg of residue is purified by pre-TLC (eluted with petroleum ether/ethyl actate=1/1) to afford 12 mg (30%) of tert-butyl 3-(5-amino-4-carbamoyl-3-(4-phenoxyphenyl)-1H-pyrazol-1-yl)piperidine-1-carboxylate as a white solid.

Step 7. Preparation of 5-amino-3-(4-phenoxyphenyl)-1-(piperidin-3-yl)-1H-pyrazole-4-carboxamide

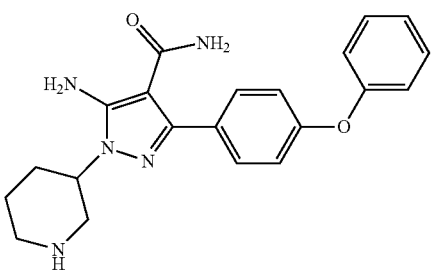 [SMILES: NC(=O)c1c(-c2ccc(Oc3ccccc3)cc2)nn(C2CCCNC2)c1N]

To a solution of tert-butyl 3-(5-amino-4-carbamoyl-3-(4-phenoxyphenyl)-1H-pyrazol-1-yl)piperidine-1-carboxylate (50 mg, 0.11 mmol) in ethyl acetate (1 mL) is added concentrated HCl (0.75 mL). The mixture is stirred at RT for 1 hour. Then saturated NaHCO$_3$ is added until pH>7, followed by ethyl acetate (50 mL). The organic layer is separated from aqueous layer, washed with brine (50 mL×3) and dried over Na$_2$SO$_4$. The resulting product is concentrated and purified by Pre-TLC (eluted with dichloromethane/MeOH/NH$_3$—H$_2$O=5/1/0.01) to afford 10 mg (25%) of 5-amino-3-(4-phenoxyphenyl)-1-(piperidin-3-yl)-1H-pyrazole-4-carboxamide as a white solid.

Step 8. Preparation of 1-(1-acryloylpiperidin-3-yl)-5-amino-3-(4-phenoxyphenyl)-1H-pyrazole-4-carboxamide

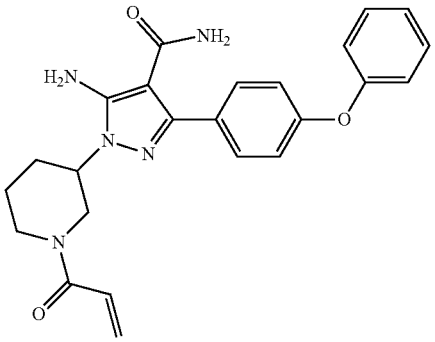 [SMILES: C=CC(=O)N1CCCC(n2nc(-c3ccc(Oc4ccccc4)cc3)c(C(N)=O)c2N)C1]

To a solution of 5-amino-3-(4-phenoxyphenyl)-1-(piperidin-3-yl)-1H-pyrazole-4-carboxamide (63 mg, 0.17 mmol) in dichloromethane (4 mL) is added pyridine (27 mg, 0.34 mmol). Then a solution of acryloyl chloride (12 mg, 0.17 mmol) in dichloromethane (1 mL) was added dropwise. After stirring at RT for 4 hours, the mixture is partitioned between 100 mL of dichloromethane and 100 mL of brine. The organic layer is separated from aqueous layer, washed with brine (100 mL×2) and dried over Na$_2$SO$_4$. Concentrated and purified by Pre-TLC (eluted with dichloromethane/MeOH=10/1) to afford 4 mg (5.5%) of 1-(1-acryloylpiperidin-3-yl)-5-amino-3-(4-phenoxyphenyl)-1H-pyrazole-4-carboxamide as a white solid.

The enantiomers of Formula (XVIII) provided by the procedure above may be prepared from 5-amino-3-(phenoxyphenyl)-1H-pyrazole-4-carbonitrile and (S)-tert-butyl 3-hydroxypiperidine-1-carboxylate using a similar procedure (step 4 to 8) for Formula (XIX), or from (R)-tert-butyl 3-hydroxypiperidine-1-carboxylate using a similar procedure (step 4 to 8) for Formula (XX). Under appropriate conditions recognized by one of ordinary skill in the art, a racemic mixture of Formula (XVIII) may be separated by chiral HPLC, the crystallization of chiral salts, or other means described above to yield Formula (XIX) and Formula (XX) of high enantiomeric purity.

In an embodiment, the BTK inhibitor is a compound selected from the structures disclosed in U.S. Patent Application Publication No. US 2015/0005277A1, the disclosure of which is incorporated by reference herein.

Other BTK inhibitors suitable for use in the described combinations also include, but are not limited to, those described in International Patent Application Publication Nos. WO 2013/010868, WO 2012/158843, WO 2012/135944, WO 2012/135937, U.S. Patent Application Publication No. 2011/0177011, and U.S. Pat. Nos. 8,501,751, 8,476,284, 8,008,309, 7,960,396, 7,825,118, 7,732,454, 7,514,444, 7,459,554, 7,405,295, and 7,393,848, the disclosures of each of which are incorporated herein by reference.

Pharmaceutical Compositions

In selected embodiments, the invention provides pharmaceutical compositions for treating solid tumor cancers, lymphomas and leukemia.

The pharmaceutical compositions are typically formulated to provide a therapeutically effective amount of a BTK inhibitor as the active ingredients, or a pharmaceutically acceptable salt, ester, prodrug thereof, solvate, hydrate or derivative thereof. Where desired, the pharmaceutical compositions contain a pharmaceutically acceptable salt and/or coordination complex thereof, and one or more pharmaceutically acceptable excipients, carriers, including inert solid diluents and fillers, diluents, including sterile aqueous solution and various organic solvents, permeation enhancers, solubilizers and adjuvants.

The pharmaceutical compositions are administered as a BTK inhibitor. Where desired, other agent(s) may be mixed into a preparation or both components may be formulated into separate preparations for use in combination separately or at the same time.

In selected embodiments, the concentration of each of the BTK inhibitors provided in the pharmaceutical compositions of the invention is independently less than, for example, 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002% or 0.0001% w/w, w/v or v/v, relative to the total mass or volume of the pharmaceutical composition.

In selected embodiments, the concentration of each of the BTK inhibitors provided in the pharmaceutical compositions of the invention is independently greater than 90%, 80%, 70%, 60%, 50%, 40%, 30%, 20%, 19.75%, 19.50%, 19.25% 19%, 18.75%, 18.50%, 18.25% 18%, 17.75%, 17.50%, 17.25% 17%, 16.75%, 16.50%, 16.25% 16%, 15.75%, 15.50%, 15.25% 15%, 14.75%, 14.50%, 14.25% 14%, 13.75%, 13.50%, 13.25% 13%, 12.75%, 12.50%, 12.25% 12%, 11.75%, 11.50%, 11.25% 11%, 10.75%, 10.50%, 10.25% 10%, 9.75%, 9.50%, 9.25% 9%, 8.75%, 8.50%, 8.25% 8%, 7.75%, 7.50%, 7.25% 7%, 6.75%, 6.50%, 6.25% 6%, 5.75%, 5.50%, 5.25% 5%, 4.75%, 4.50%, 4.25%, 4%, 3.75%, 3.50%, 3.25%, 3%, 2.75%, 2.50%, 2.25%, 2%, 1.75%, 1.50%, 125%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002% or 0.0001% w/w, w/v, or v/v, relative to the total mass or volume of the pharmaceutical composition.

In selected embodiments, the concentration of each of the BTK inhibitors of the invention is independently in the range from approximately 0.0001% to approximately 50%, approximately 0.001% to approximately 40%, approximately 0.01% to approximately 30%, approximately 0.02% to approximately 29%, approximately 0.03% to approximately 28%, approximately 0.04% to approximately 27%, approximately 0.05% to approximately 26%, approximately 0.06% to approximately 25%, approximately 0.07% to approximately 24%, approximately 0.08% to approximately 23%, approximately 0.09% to approximately 22%, approximately 0.1% to approximately 21%, approximately 0.2% to approximately 20%, approximately 0.3% to approximately 19%, approximately 0.4% to approximately 18%, approximately 0.5% to approximately 17%, approximately 0.6% to approximately 16%, approximately 0.7% to approximately 15%, approximately 0.8% to approximately 14%, approximately 0.9% to approximately 12% or approximately 1% to approximately 10% w/w, w/v or v/v, relative to the total mass or volume of the pharmaceutical composition.

In selected embodiments, the concentration of each of the BTK inhibitors of the invention is independently in the range from approximately 0.001% to approximately 10%, approximately 0.01% to approximately 5%, approximately 0.02% to approximately 4.5%, approximately 0.03% to approximately 4%, approximately 0.04% to approximately 3.5%, approximately 0.05% to approximately 3%, approximately 0.06% to approximately 2.5%, approximately 0.07% to approximately 2%, approximately 0.08% to approximately 1.5%, approximately 0.09% to approximately 1%, approximately 0.1% to approximately 0.9% w/w, w/v or v/v, relative to the total mass or volume of the pharmaceutical composition.

In selected embodiments, the amount of each of the BTK inhibitors of the invention is independently equal to or less than 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g or 0.0001 g.

In selected embodiments, the amount of each of the BTK inhibitors of the invention is independently more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5, or 3 g.

Each of the BTK inhibitors according to the invention is effective over a wide dosage range. For example, in the treatment of adult humans, dosages independently range from 0.01 to 1000 mg, from 0.5 to 100 mg, from 1 to 50 mg per day, and from 5 to 40 mg per day are examples of dosages that may be used. The exact dosage will depend upon the route of administration, the form in which the compound is administered, the gender and age of the subject to be treated, the body weight of the subject to be treated, and the preference and experience of the attending physician.

Described below are non-limiting pharmaceutical compositions and methods for preparing the same.

Pharmaceutical Compositions for Oral Administration

In selected embodiments, the invention provides a pharmaceutical composition for oral administration containing the BTK inhibitor, and a pharmaceutical excipient suitable for oral administration.

In selected embodiments, the invention provides a solid pharmaceutical composition for oral administration containing: (i) an effective amount of a BTK inhibitor and (ii) a pharmaceutical excipient suitable for oral administration. In selected embodiments, the composition further contains (iii) an effective amount of another therapeutic agent.

In selected embodiments, the pharmaceutical composition may be a liquid pharmaceutical composition suitable for oral consumption. Pharmaceutical compositions of the invention suitable for oral administration can be presented as discrete dosage forms, such as capsules, sachets, or tablets, or liquids or aerosol sprays each containing a predetermined amount of an active ingredient as a powder or in granules, a solution, or a suspension in an aqueous or non-aqueous liquid, an oil-in-water emulsion, or a water-in-oil liquid emulsion. Such dosage forms can be prepared by any of the methods of pharmacy, but all methods include the step of bringing the active ingredient(s) into association with the carrier, which constitutes one or more necessary ingredients. In general, the compositions are prepared by uniformly and intimately admixing the active ingredient(s) with liquid carriers or finely divided solid carriers or both, and then, if necessary, shaping the product into the desired presentation. For example, a tablet can be prepared by compression or molding, optionally with one or more accessory ingredients. Compressed tablets can be prepared by compressing in a suitable machine the active ingredient in a free-flowing form such as powder or granules, optionally mixed with an excipient such as, but not limited to, a binder, a lubricant, an inert diluent, and/or a surface active or dispersing agent. Molded tablets can be made by molding in a suitable machine a mixture of the powdered compound moistened with an inert liquid diluent.

The invention further encompasses anhydrous pharmaceutical compositions and dosage forms since water can facilitate the degradation of some compounds. For example, water may be added (e.g., 5%) in the pharmaceutical arts as a means of simulating long-term storage in order to determine characteristics such as shelf-life or the stability of formulations over time. Anhydrous pharmaceutical compositions and dosage forms of the invention can be prepared using anhydrous or low moisture containing ingredients and low moisture or low humidity conditions. Pharmaceutical compositions and dosage forms of the invention which contain lactose can be made anhydrous if substantial contact with moisture and/or humidity during manufacturing, packaging, and/or storage is expected. An anhydrous pharmaceutical composition may be prepared and stored such that its anhydrous nature is maintained. Accordingly, anhydrous compositions may be packaged using materials known to prevent exposure to water such that they can be included in suitable formulary kits. Examples of suitable packaging include, but are not limited to, hermetically sealed foils, plastic or the like, unit dose containers, blister packs, and strip packs.

Each of the BTK inhibitors as active ingredients can be combined in an intimate admixture with a pharmaceutical carrier according to conventional pharmaceutical compounding techniques. The carrier can take a wide variety of forms depending on the form of preparation desired for administration. In preparing the compositions for an oral dosage form, any of the usual pharmaceutical media can be employed as carriers, such as, for example, water, glycols, oils, alcohols, flavoring agents, preservatives, coloring agents, and the like in the case of oral liquid preparations (such as suspensions, solutions, and elixirs) or aerosols; or carriers such as starches, sugars, micro-crystalline cellulose, diluents, granulating agents, lubricants, binders, and disintegrating agents can be used in the case of oral solid preparations, in some embodiments without employing the use of lactose. For example, suitable carriers include powders, capsules, and tablets, with the solid oral preparations. If desired, tablets can be coated by standard aqueous or nonaqueous techniques.

Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, microcrystalline cellulose, and mixtures thereof.

Examples of suitable fillers for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof.

Disintegrants may be used in the compositions of the invention to provide tablets that disintegrate when exposed to an aqueous environment. Too much of a disintegrant may produce tablets which disintegrate in the bottle. Too little may be insufficient for disintegration to occur, thus altering the rate and extent of release of the active ingredients from the dosage form. Thus, a sufficient amount of disintegrant that is neither too little nor too much to detrimentally alter the release of the active ingredient(s) may be used to form the dosage forms of the compounds disclosed herein. The amount of disintegrant used may vary based upon the type of formulation and mode of administration, and may be readily discernible to those of ordinary skill in the art. About 0.5 to about 15 weight percent of disintegrant, or about 1 to about 5 weight percent of disintegrant, may be used in the pharmaceutical composition. Disintegrants that can be used to form pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums or mixtures thereof.

Lubricants which can be used to form pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyllaureate, agar, or mixtures thereof. Additional lubricants include, for example, a syloid silica gel, a coagulated aerosol of synthetic silica, or mixtures thereof. A lubricant can optionally be added, in an amount of less than about 1 weight percent of the pharmaceutical composition.

When aqueous suspensions and/or elixirs are desired for oral administration, the essential active ingredient therein may be combined with various sweetening or flavoring agents, coloring matter or dyes and, if so desired, emulsifying and/or suspending agents, together with such diluents as water, ethanol, propylene glycol, glycerin and various combinations thereof.

The tablets can be uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Surfactants which can be used to form pharmaceutical compositions and dosage forms of the invention include, but are not limited to, hydrophilic surfactants, lipophilic surfactants, and mixtures thereof. That is, a mixture of hydrophilic surfactants may be employed, a mixture of lipophilic surfactants may be employed, or a mixture of at least one hydrophilic surfactant and at least one lipophilic surfactant may be employed.

A suitable hydrophilic surfactant may generally have an HLB value of at least 10, while suitable lipophilic surfactants may generally have an HLB value of or less than about 10. An empirical parameter used to characterize the relative hydrophilicity and hydrophobicity of non-ionic amphiphilic compounds is the hydrophilic-lipophilic balance ("HLB" value). Surfactants with lower HLB values are more lipophilic or hydrophobic, and have greater solubility in oils, while surfactants with higher HLB values are more hydrophilic, and have greater solubility in aqueous solutions. Hydrophilic surfactants are generally considered to be those compounds having an HLB value greater than about 10, as well as anionic, cationic, or zwitterionic compounds for which the HLB scale is not generally applicable. Similarly, lipophilic (i.e., hydrophobic) surfactants are compounds having an HLB value equal to or less than about 10. However, HLB value of a surfactant is merely a rough guide generally used to enable formulation of industrial, pharmaceutical and cosmetic emulsions.

Hydrophilic surfactants may be either ionic or non-ionic. Suitable ionic surfactants include, but are not limited to, alkylammonium salts; fusidic acid salts; fatty acid derivatives of amino acids, oligopeptides, and polypeptides; glyceride derivatives of amino acids, oligopeptides, and polypeptides; lecithins and hydrogenated lecithins; lysolecithins and hydrogenated lysolecithins; phospholipids and derivatives thereof; lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Within the aforementioned group, ionic surfactants include, by way of example: lecithins, lysolecithin, phospholipids, lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Ionic surfactants may be the ionized forms of lecithin, lysolecithin, phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholylsarcosine, caproate, caprylate, caprate, laurate, myristate, palmitate, oleate, ricinoleate, linoleate, linolenate, stearate, lauryl sulfate, teracecyl sulfate, docusate, lauroyl carnitines, palmitoyl carnitines, myristoyl carnitines, and salts and mixtures thereof.

Hydrophilic non-ionic surfactants may include, but not limited to, alkylglucosides; alkylmaltosides; alkylthioglucosides; lauryl macrogolglycerides; polyoxyalkylene alkyl ethers such as polyethylene glycol alkyl ethers; polyoxyalkylene alkylphenols such as polyethylene glycol alkyl phenols; polyoxyalkylene alkyl phenol fatty acid esters such as polyethylene glycol fatty acids monoesters and polyethylene glycol fatty acids diesters; polyethylene glycol glycerol fatty acid esters; polyglycerol fatty acid esters; polyoxyalkylene sorbitan fatty acid esters such as polyethylene glycol sorbitan fatty acid esters; hydrophilic transesterification products of a polyol with at least one member of the group consisting of glycerides, vegetable oils, hydrogenated vegetable oils, fatty acids, and sterols; polyoxyethylene sterols, derivatives, and analogues thereof; polyoxyethylated vitamins and derivatives thereof; polyoxyethylene-polyoxypropylene block copolymers; and mixtures thereof; polyethylene glycol sorbitan fatty acid esters and hydrophilic transesterification products of a polyol with at least one member of the group consisting of triglycerides, vegetable oils, and hydrogenated vegetable oils. The polyol may be glycerol, ethylene glycol, polyethylene glycol, sorbitol, propylene glycol, pentaerythritol, or a saccharide.

Other hydrophilic-non-ionic surfactants include, without limitation, PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phyto sterol, PEG-30 soya sterol, PEG-20 trioleate, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-10 oleate, Tween 40, Tween 60, sucrose monostearate, sucrose monolaurate, sucrose monopalmitate, PEG 10-100 nonyl phenol series, PEG 15-100 octyl phenol series, and poloxamers.

Suitable lipophilic surfactants include, by way of example only: fatty alcohols; glycerol fatty acid esters; acetylated glycerol fatty acid esters; lower alcohol fatty acids esters; propylene glycol fatty acid esters; sorbitan fatty acid esters; polyethylene glycol sorbitan fatty acid esters; sterols and sterol derivatives; polyoxyethylated sterols and sterol derivatives; polyethylene glycol alkyl ethers; sugar esters; sugar ethers; lactic acid derivatives of mono- and di-glycerides; hydrophobic transesterification products of a polyol with at least one member of the group consisting of glycerides, vegetable oils, hydrogenated vegetable oils, fatty acids and sterols; oil-soluble vitamins/vitamin derivatives; and mixtures thereof. Within this group, preferred lipophilic surfactants include glycerol fatty acid esters, propylene glycol fatty acid esters, and mixtures thereof, or are hydrophobic transesterification products of a polyol with at least one member of the group consisting of vegetable oils, hydrogenated vegetable oils, and triglycerides.

In an embodiment, the composition may include a solubilizer to ensure good solubilization and/or dissolution of the compound of the present invention and to minimize precipitation of the compound of the present invention. This can be especially important for compositions for non-oral use— e.g., compositions for injection. A solubilizer may also be added to increase the solubility of the hydrophilic drug and/or other components, such as surfactants, or to maintain the composition as a stable or homogeneous solution or dispersion.

Examples of suitable solubilizers include, but are not limited to, the following: alcohols and polyols, such as ethanol, isopropanol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose and other cellulose derivatives, cyclodextrins and cyclodextrin derivatives; ethers of polyethylene glycols having an average molecular weight of about 200 to about 6000, such as tetrahydrofurfuryl alcohol PEG ether (glycofurol) or methoxy PEG; amides and other nitrogen-containing compounds such as 2-pyrrolidone, 2-piperidone, ε-caprolactam, N-alkylpyrrolidone, N-hydroxyalkylpyrrolidone, N-alkylpiperidone, N-alkylcaprolactam, dimethylacetamide and polyvinylpyrrolidone; esters such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, .epsilon.-caprolactone and isomers thereof, δ-valerolactone and isomers thereof, β-butyrolactone and isomers thereof; and other solubilizers known in the art, such as dimethyl acetamide, dimethyl isosorbide, N-methyl pyrrolidones, monooctanoin, diethylene glycol monoethyl ether, and water.

Mixtures of solubilizers may also be used. Examples include, but not limited to, triacetin, triethylcitrate, ethyl oleate, ethyl caprylate, dimethylacetamide, N-methylpyrrolidone, N-hydroxyethylpyrrolidone, polyvinylpyrrolidone, hydroxypropyl methylcellulose, hydroxypropyl cyclodextrins, ethanol, polyethylene glycol 200-100, glycofurol, transcutol, propylene glycol, and dimethyl isosorbide. Particularly preferred solubilizers include sorbitol, glycerol, triacetin, ethyl alcohol, PEG-400, glycofurol and propylene glycol.

The amount of solubilizer that can be included is not particularly limited. The amount of a given solubilizer may be limited to a bioacceptable amount, which may be readily determined by one of skill in the art. In some circumstances, it may be advantageous to include amounts of solubilizers far in excess of bioacceptable amounts, for example to maximize the concentration of the drug, with excess solubilizer removed prior to providing the composition to a patient using conventional techniques, such as distillation or evaporation. Thus, if present, the solubilizer can be in a weight ratio of 10%, 25%, 50%, 100%, or up to about 200% by weight, based on the combined weight of the drug, and other excipients. If desired, very small amounts of solubilizer may also be used, such as 5%, 2%, 1% or even less. Typically, the solubilizer may be present in an amount of about 1% to about 100%, more typically about 5% to about 25% by weight.

The composition can further include one or more pharmaceutically acceptable additives and excipients. Such additives and excipients include, without limitation, detackifiers, anti-foaming agents, buffering agents, polymers, antioxidants, preservatives, chelating agents, viscomodulators, tonicifiers, flavorants, colorants, odorants, opacifiers, suspending agents, binders, fillers, plasticizers, lubricants, and mixtures thereof.

In addition, an acid or a base may be incorporated into the composition to facilitate processing, to enhance stability, or for other reasons. Examples of pharmaceutically acceptable bases include amino acids, amino acid esters, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrocalcite, magnesium aluminum hydroxide, diisopropylethylamine, ethanolamine, ethylenediamine, triethanolamine, triethylamine, triisopropanolamine, trimethylamine, tris(hydroxymethyl) aminomethane (TRIS) and the like. Also suitable are bases that are salts of a pharmaceutically acceptable acid, such as acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid, and the like. Salts of polyprotic acids, such as sodium phosphate, disodium hydrogen phosphate, and sodium dihydrogen phosphate can also be used. When the base is a salt, the cation can be any convenient and pharmaceutically acceptable cation, such as ammonium, alkali metals and alkaline earth metals. Example may include, but not limited to, sodium, potassium, lithium, magnesium, calcium and ammonium.

Suitable acids are pharmaceutically acceptable organic or inorganic acids. Examples of suitable inorganic acids include hydrochloric acid, hydrobromic acid, hydriodic acid, sulfuric acid, nitric acid, boric acid, phosphoric acid, and the like. Examples of suitable organic acids include acetic acid, acrylic acid, adipic acid, alginic acid, alkanesulfonic acids, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid and uric acid.

Pharmaceutical Compositions for Injection

In selected embodiments, the invention provides a pharmaceutical composition for injection containing the BTK inhibitors and a pharmaceutical excipient suitable for injection. Components and amounts of agents in the compositions are as described herein.

The forms in which the compositions of the present invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Aqueous solutions in saline are also conventionally used for injection. Ethanol, glycerol, propylene glycol and liquid polyethylene glycol (and suitable mixtures thereof), cyclodextrin derivatives, and vegetable oils may also be employed. The proper fluidity can be maintained, for example, by the use of a coating, such as lecithin, for the maintenance of the required particle size in the case of dispersion and by the use of surfactants. The prevention of the action of microorganisms can be brought about by various antibacterial and antifungal agents, for example, parabens, chlorobutanol, phenol, sorbic acid and thimerosal.

Sterile injectable solutions are prepared by incorporating the BTK inhibitors in the required amounts in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, certain desirable methods of preparation are spray-drying, vacuum-drying and freeze-drying (lyophilization) techniques which yield a powder of the active ingredient plus any additional desired ingredient from a previously sterile-filtered solution thereof. Other lyophilized or spray-dried antibody formulations known to those of skill in the art may also be employed with the present invention. Such formulations include those disclosed in U.S. Pat. Nos. 5,908,826, 6,267,958, 7,682,609, 7,592,004, and 8,298,530, and U.S. Patent Application Publication No. 2010/0158925, the teachings of which are specifically incorporated by reference herein.

Pharmaceutical Compositions for Topical Delivery

In some embodiments, the invention provides a pharmaceutical composition for transdermal delivery containing the BTK inhibitors and a pharmaceutical excipient suitable for transdermal delivery.

Compositions of the present invention can be formulated into preparations in solid, semi-solid, or liquid forms suitable for local or topical administration, such as gels, water soluble jellies, creams, lotions, suspensions, foams, powders, slurries, ointments, solutions, oils, pastes, suppositories, sprays, emulsions, saline solutions, dimethylsulfoxide (DMSO)-based solutions. In general, carriers with higher densities are capable of providing an area with a prolonged exposure to the active ingredients. In contrast, a solution formulation may provide more immediate exposure of the active ingredient to the chosen area.

The pharmaceutical compositions also may comprise suitable solid or gel phase carriers or excipients, which are compounds that allow increased penetration of, or assist in the delivery of, therapeutic molecules across the stratum corneum permeability barrier of the skin. There are many of these penetration-enhancing molecules known to those trained in the art of topical formulation. Examples of such carriers and excipients include, but are not limited to, humectants (e.g., urea), glycols (e.g., propylene glycol), alcohols (e.g., ethanol), fatty acids (e.g., oleic acid), surfactants (e.g., isopropyl myristate and sodium lauryl sulfate), pyrrolidones, glycerol monolaurate, sulfoxides, terpenes (e.g., menthol), amines, amides, alkanes, alkanols, water, calcium carbonate, calcium phosphate, various sugars, starches, cellulose derivatives, gelatin, and polymers such as polyethylene glycols.

Another formulation for use in the methods of the present invention employs transdermal delivery devices ("patches"). Such transdermal patches may be used to provide continuous or discontinuous infusion of the BTK inhibitors in controlled amounts, either with or without another agent.

The construction and use of transdermal patches for the delivery of pharmaceutical agents is well known in the art. See, e.g., U.S. Pat. Nos. 5,023,252; 4,992,445 and 5,001,139. Such patches may be constructed for continuous, pulsatile, or on demand delivery of pharmaceutical agents.

Other Pharmaceutical Compositions

Pharmaceutical compositions may also be prepared from compositions described herein and one or more pharmaceutically acceptable excipients suitable for sublingual, buccal, rectal, intraosseous, intraocular, intranasal, epidural, or intraspinal administration. Preparations for such pharmaceutical compositions are well-known in the art. See, e.g., Anderson, et al., *Handbook of Clinical Drug Data*, Tenth Edition, McGraw-Hill, 2002; and Pratt and Taylor, eds., *Principles of Drug Action*, Third Edition, Churchill Livingston, N.Y., 1990, each of which is incorporated by reference herein in its entirety.

Administration of the BTK inhibitors or pharmaceutical compositions of these compounds can be effected by any method that enables delivery of the compounds to the site of action. These methods include oral routes, intraduodenal routes, parenteral injection (including intravenous, intraarterial, subcutaneous, intramuscular, intravascular, intraperitoneal or infusion), topical (e.g., transdermal application), rectal administration, via local delivery by catheter or stent or through inhalation. The combination of compounds can also be administered intraadiposally or intrathecally.

Parenteral administration forms include solutions or suspensions of active compound in sterile aqueous solutions, for example, aqueous propylene glycol or dextrose solutions. Such dosage forms can be suitably buffered, if desired.

The invention also provides kits. The kits include the BTK inhibitors, either alone or in combination in suitable packaging, and written material that can include instructions for use, discussion of clinical studies and listing of side effects. Such kits may also include information, such as scientific literature references, package insert materials, clinical trial results, and/or summaries of these and the like, which indicate or establish the activities and/or advantages of the composition, and/or which describe dosing, administration, side effects, drug interactions, or other information useful to the health care provider. Such information may be based on the results of various studies, for example, studies using experimental animals involving in vivo models and studies based on human clinical trials. The kit may further contain another therapeutic agent. In selected embodiments, the BTK inhibitors and the agent are provided as separate compositions in separate containers within the kit. In selected embodiments, the BTK inhibitors and the agent are provided as a single composition within a container in the kit. Suitable packaging and additional articles for use (e.g., measuring cup for liquid preparations, foil wrapping to minimize exposure to air, and the like) are known in the art and may be included in the kit. Kits described herein can be provided, marketed and/or promoted to health providers, including physicians, nurses, pharmacists, formulary officials, and the like. Kits may also, in selected embodiments, be marketed directly to the consumer.

Dosages and Dosing Regimens

The amounts of BTK inhibitors administered will be dependent on the mammal being treated, the severity of the disorder or condition, the rate of administration, the disposition of the compounds and the discretion of the prescribing physician. However, an effective dosage is in the range of about 0.001 to about 100 mg per kg body weight per day, such as about 1 to about 35 mg/kg/day, in single or divided doses. For a 70 kg human, this would amount to about 0.05 to 7 g/day, such as about 0.05 to about 2.5 g/day. In some instances, dosage levels below the lower limit of the aforesaid range may be more than adequate, while in other cases still larger doses may be employed without causing any harmful side effect—e.g., by dividing such larger doses into several small doses for administration throughout the day.

In selected embodiments, the BTK inhibitor is administered in a single dose. Typically, such administration may be by injection, for example by intravenous injection, in order to introduce the agents quickly. However, other routes may be used as appropriate. A single dose of the BTK inhibitor may also be used for treatment of an acute condition.

In selected embodiments, the BTK inhibitor is administered in multiple doses. Dosing may be about once, twice, three times, four times, five times, six times, or more than six times per day. Dosing may be about once a month, once every two weeks, once a week, or once every other day. In other embodiments, the BTK inhibitor is administered about once per day to about 6 times per day. In another embodiment the administration of the combination of the BTK inhibitor continues for less than about 7 days. In yet another embodiment the administration continues for more than about 6, 10, 14, 28 days, two months, six months, or one year. In some cases, continuous dosing is achieved and maintained as long as necessary.

Administration of the BTK inhibitors of the invention may continue as long as necessary. In selected embodiments, the BTK inhibitor is administered for more than 1, 2, 3, 4, 5, 6, 7, 14, or 28 days. In some embodiments, the BTK inhibitor is administered for less than 28, 14, 7, 6, 5, 4, 3, 2, or 1 day. In selected embodiments, the BTK inhibitor is administered chronically on an ongoing basis—e.g., for the treatment of chronic effects.

In some embodiments, an effective dosage of each of the BTK inhibitors is in the range of about 1 mg to about 500 mg, about 10 mg to about 300 mg, about 20 mg to about 250 mg, about 25 mg to about 200 mg, about 10 mg to about 200 mg, about 20 mg to about 150 mg, about 30 mg to about 120 mg, about 10 mg to about 90 mg, about 20 mg to about 80 mg, about 30 mg to about 70 mg, about 40 mg to about 60 mg, about 45 mg to about 55 mg, about 48 mg to about 52 mg, about 50 mg to about 150 mg, about 60 mg to about 140 mg, about 70 mg to about 130 mg, about 80 mg to about 120 mg, about 90 mg to about 110 mg, about 95 mg to about 105 mg, about 150 mg to about 250 mg, about 160 mg to about 240 mg, about 170 mg to about 230 mg, about 180 mg to about 220 mg, about 190 mg to about 210 mg, about 195 mg to about 205 mg, or about 198 to about 202 mg. In some embodiments, an effective dosage of each of the BTK inhibitors is about 25 mg, about 50 mg, about 75 mg, about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, or about 500 mg. In some embodiments, an effective dosage of each of the BTK inhibitors is 25 mg, 50 mg, 75 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, or 500 mg.

In some embodiments, an effective dosage of each of the BTK inhibitors is in the range of about 0.01 mg/kg to about 4.3 mg/kg, about 0.15 mg/kg to about 3.6 mg/kg, about 0.3 mg/kg to about 3.2 mg/kg, about 0.35 mg/kg to about 2.85 mg/kg, about 0.15 mg/kg to about 2.85 mg/kg, about 0.3 mg to about 2.15 mg/kg, about 0.45 mg/kg to about 1.7 mg/kg, about 0.15 mg/kg to about 1.3 mg/kg, about 0.3 mg/kg to about 1.15 mg/kg, about 0.45 mg/kg to about 1 mg/kg, about 0.55 mg/kg to about 0.85 mg/kg, about 0.65 mg/kg to about 0.8 mg/kg, about 0.7 mg/kg to about 0.75 mg/kg, about 0.7 mg/kg to about 2.15 mg/kg, about 0.85 mg/kg to about 2 mg/kg, about 1 mg/kg to about 1.85 mg/kg, about 1.15 mg/kg to about 1.7 mg/kg, about 1.3 mg/kg mg to about 1.6 mg/kg, about 1.35 mg/kg to about 1.5 mg/kg, about 2.15 mg/kg to about 3.6 mg/kg, about 2.3 mg/kg to about 3.4 mg/kg, about 2.4 mg/kg to about 3.3 mg/kg, about 2.6 mg/kg to about 3.15 mg/kg, about 2.7 mg/kg to about 3 mg/kg, about 2.8 mg/kg to about 3 mg/kg, or about 2.85 mg/kg to about 2.95 mg/kg. In some embodiments, an effective dosage of each of the BTK inhibitors is about 0.35 mg/kg, about 0.7 mg/kg, about 1 mg/kg, about 1.4 mg/kg, about 1.8 mg/kg, about 2.1 mg/kg, about 2.5 mg/kg, about 2.85 mg/kg, about 3.2 mg/kg, or about 3.6 mg/kg.

In some embodiments, a inhibitor of each of the BTK inhibitors is adminstered at a dosage of 10 to 400 mg BID, including a dosage of 5 mg, 10 mg, 12.5 mg, 25 mg, 50 mg, 75 mg, 100 mg, 150 mg, 175 mg, 200 mg, 225 mg, 250 mg, 275 mg, 300 mg, 325 mg, 350 mg, 375 mg, 400 mg, 425 mg, 450 mg, 475 mg, and 500 mg BID.

An effective amount of the BTK inhibitor may be administered in either single or multiple doses by any of the accepted modes of administration of agents having similar utilities, including rectal, buccal, intranasal and transdermal routes, by intra-arterial injection, intravenously, intraperitoneally, parenterally, intramuscularly, subcutaneously, orally, topically, or as an inhalant.

The effective amount of the BTK inhibitor is in the range of from about 1 mg to about 300 mg, more preferably from about 1 mg to about 200 mg, more preferably from about 1 mg to about 100 mg, and even more preferably from about 1 mg to about 50 mg, on a daily or twice daily basis.

Methods of Treatment

In selected embodiments, the invention relates to a method of treating a disorder associated with overexpression of CXCR4, dysregulated signaling of CXCR4, or pathogenesis mediated by the CXCR4/SDF-1 signaling pathway in a mammal that comprises administering to said mammal a therapeutically effective amount of a BTK inhibitor, or a pharmaceutically acceptable salt or ester, prodrug thereof, solvate or hydrate of the BTK inhibitor.

In selected embodiments, the invention relates to a method of treating, with a BTK inhibitor, a disorder associated with overexpression of CXCR4, dysregulated signaling of CXCR4, or pathogenesis mediated by the CXCR4/SDF-1 signaling pathway in a mammal selected from the group consisting of bladder cancer, head and neck cancer, pancreatic ductal adenocarcinoma (PDA), pancreatic cancer, colon carcinoma, mammary carcinoma, breast cancer, fibrosarcoma, mesothelioma, renal cell carcinoma, lung carcinoma, thyoma, prostate cancer, colorectal cancer, ovarian cancer, acute myeloid leukemia, thymus cancer, brain cancer, squamous cell cancer, skin cancer, eye cancer, retinoblastoma, melanoma, intraocular melanoma, oral cavity and oropharyngeal cancers, gastric cancer, stomach cancer, cervical cancer, head, neck, renal cancer, kidney cancer, liver cancer, ovarian cancer, prostate cancer, colorectal cancer, esophageal cancer, testicular cancer, gynecological cancer, thyroid cancer, acquired immune deficiency syndrome (AIDS)-related cancers (e.g., lymphoma and Kaposi's sarcoma), viral-induced cancers such as cervical carcinoma (human papillomavirus), B-cell lymphoproliferative disease and nasopharyngeal carcinoma (Epstein-Barr virus), Kaposi's Sarcoma and primary effusion lymphomas (Kaposi's sarcoma herpesvirus), hepatocellular carcinoma (hepatitis B and hepatitis C viruses), T-cell leukemias (Human T-cell leukemia virus-1), glioblastoma, esophogeal tumors, hematological neoplasms, non-small-cell lung cancer, chronic myelocytic leukemia, diffuse large B-cell lymphoma, esophagus tumor, follicle center lymphoma, head and neck tumor, hepatitis C virus infection, hepatocellular carcinoma, Hodgkin's disease, metastatic colon cancer, multiple myeloma, non-Hodgkin's lymphoma, indolent non-Hodgkin's lymphoma, ovary tumor, pancreas tumor, renal cell carcinoma, small-cell lung cancer, stage IV melanoma, osteosarcoma, sarcoma, glioblastoma multiforme, rheumatoid arthritis, lupus, IgA nephropathy, membranous nephropathy, pemphigus, cancer metastatis, human papillomavirus-induced disorders, and WHIM syndrome (warts, hypogammaglobulinemia, bacterial infections, and pathognomonic myelokathexis).

In selected embodiments, the invention relates to a method of treating an inflammatory, immune, or autoimmune disorder associated with overexpression of CXCR4, dysregulated signaling of CXCR4, or pathogenesis mediated by the CXCR4/SDF-1 signaling pathway in a mammal with a BTK inhibitor. In selected embodiments, the invention also relates to a method of treating a disease with a BTK inhibitor, wherein the disease is selected from the group consisting of tumor angiogenesis, chronic inflammatory disease, rheumatoid arthritis, atherosclerosis, inflammatory bowel disease, skin diseases such as psoriasis, eczema, and scleroderma, diabetes, diabetic retinopathy, retinopathy of prematurity, age-related macular degeneration, hemangioma, glioma and melanoma, ulcerative colitis, atopic dermatitis, pouchitis, spondylarthritis, uveitis, Behcet's disease, polymyalgia rheumatica, giant-cell arteritis, sarcoidosis, Kawasaki disease, juvenile idiopathic arthritis, hidratenitis suppurativa, Sjögren's syndrome, psoriatic arthritis, juvenile rheumatoid arthritis, ankylosing spondylitis, Crohn's Disease, lupus, and lupus nephritis.

In selected embodiments, the invention relates to a method of treating with a BTK inhibitor a disorder associated with overexpression of CXCR4, dysregulated signaling of CXCR4, or pathogenesis mediated by the CXCR4/SDF-1 signaling pathway including but not limited to acute myeloid leukemia, thymus cancer, brain cancer, lung cancer, squamous cell cancer, skin cancer, eye cancer, retinoblastoma, intraocular melanoma, oral cavity and oropharyngeal cancer, bladder cancer, gastric cancer, stomach cancer, pancreatic cancer, bladder cancer, breast cancer, cervical, head cancer, neck cancer, renal cancer, kidney cancer, liver cancer, ovarian cancer, prostate cancer, colorectal cancer, esophageal cancer, testicular cancer, gynecological cancer, thyroid cancer, and CNS, PNS, AIDS-related (e.g., lymphoma and Kaposi's sarcoma) or viral-induced cancers. In some embodiments, said pharmaceutical composition is for the treatment of a non-cancerous hyperproliferative disorder such as benign hyperplasia of the skin (e.g., psoriasis), restenosis, or prostate (e.g., benign prostatic hypertrophy (BPH)).

Efficacy of the compounds and combinations of compounds described herein in treating, preventing and/or managing the indicated diseases or disorders can be tested using various models known in the art. For example, models for determining efficacy of treatments for overexpression of CXCR4, dysregulated signaling of CXCR4, or pathogenesis mediated by the CXCR4/SDF-1 signaling pathway are described, e.g., in Bachelerie, *Disease Markers,* 2010, 29, 189-198. Models for determining efficacy of treatments for pancreatic cancer are described in Herreros-Villanueva, et al., *World J. Gastroenterol.* 2012, 18, 1286-1294. Models for determining efficacy of treatments for breast cancer are described e.g. in Fantozzi, *Breast Cancer Res.* 2006, 8, 212. Models for determining efficacy of treatments for ovarian cancer are described, e.g., in Mullany, et al., *Endocrinology* 2012, 153, 1585-92; and Fong et al., *J. Ovarian Res.* 2009, 2, 12. Models for determining efficacy of treatments for melanoma are described, e.g., in Damsky, et al., *Pigment Cell & Melanoma Res.* 2010, 23, 853-859. Models for determining efficacy of treatments for lung cancer are described, e.g., in Meuwissen, et al., *Genes & Development,* 2005, 19, 643-664. Models for determining efficacy of treatments for lung cancer are described, e.g., in Kim, *Clin. Exp. Otorhinolaryngol.* 2009, 2, 55-60; and Sano, *Head Neck Oncol.* 2009, 1, 32. Models for determining efficacy of treatments for colorectal cancer, including the CT26 model, are described below in the examples.

Efficacy of the compounds and combinations of compounds described herein in treating, preventing and/or managing other indicated diseases or disorders described here can also be tested using various models known in the art. Efficacy in treating, preventing and/or managing asthma can be assessed using the ova induced asthma model described, for example, in Lee, et al., *J. Allergy Clin. Immunol.* 2006, 118, 403-9. Efficacy in treating, preventing and/or managing arthritis (e.g., rheumatoid or psoriatic arthritis) can be assessed using the autoimmune animal models described in, for example, Williams, et al., *Chem. Biol.* 2010, 17, 123-34, WO 2009/088986, WO 2009/088880, and WO 2011/008302. Efficacy in treating, preventing and/or managing psoriasis can be assessed using transgenic or knockout mouse model with targeted mutations in epidermis, vasculature or immune cells, mouse model resulting from spontaneous mutations, and immuno-deficient mouse model with xenotransplantation of human skin or immune cells, all of which are described, for example, in Boehncke, et al., *Clinics in Dermatology,* 2007, 25, 596-605. Efficacy in treating, preventing and/or managing fibrosis or fibrotic conditions can be assessed using the unilateral ureteral obstruction model of renal fibrosis, which is described, for example, in Chevalier, et al., *Kidney International* 2009, 75, 1145-1152; the bleomycin induced model of pulmonary fibrosis described in, for example, Moore, et al., *Am. J. Physiol. Lung. Cell. Mol. Physiol.* 2008, 294, L152-L160; a variety of liver/biliary fibrosis models described in, for example, Chuang, et al., *Clin. Liver Dis.* 2008, 12, 333-347 and Omenetti, et al., *Laboratory Investigation,* 2007, 87, 499-514 (biliary duct-ligated model); or any of a number of myelofibrosis mouse models such as described in Varicchio, et al., *Expert Rev. Hematol.* 2009, 2, 315-334. Efficacy in treating, preventing and/or managing scleroderma can be assessed using a mouse model induced by repeated local injections of bleomycin described, for example, in Yamamoto, et al., *J. Invest. Dermatol.* 1999, 112, 456-462. Efficacy in treating, preventing and/or managing dermatomyositis can be assessed using a myositis mouse model induced by immunization with rabbit myosin as described, for example, in Phyanagi, et al., *Arthritis & Rheumatism,* 2009, 60(10), 3118-3127. Efficacy in treating, preventing and/or managing lupus can be assessed using various animal models described, for example, in Ghoreishi, et al., *Lupus,* 2009, 19, 1029-1035; Ohl, et al., *J. Biomed. & Biotechnol.,* Article ID 432595 (2011); Xia, et al., *Rheumatology,* 2011, 50, 2187-2196; Pau, et al., *PLoS ONE,* 2012, 7(5), e36761; Mustafa, et al., *Toxicology,* 2011, 90, 156-168; Ichikawa, et al., *Arthritis & Rheumatism,* 2012, 62(2), 493-503; Rankin, et al., *J. Immunology,* 2012, 188, 1656-1667. Efficacy in treating, preventing and/or managing Sjögren's syndrome can be assessed using various mouse models described, for example, in Chiorini, et al., *J. Autoimmunity,* 2009, 33, 190-196.

Methods of Treating Patients Sensitive to Bleeding Events

In selected embodiments, the invention provides a method of treating a treating a disorder associated with overexpression of CXCR4, dysregulated signaling of CXCR4, or pathogenesis mediated by the CXCR4/SDF-1 signaling pathway in a human sensitive to bleeding events, comprising the step of administering a therapeutically effective dose of a BTK inhibitor or a pharmaceutically-acceptable salt, cocrystal, hydrate, solvate, or prodrug thereof. In a preferred embodiment, the invention provides a method of treating a treating a disorder associated with overexpression of CXCR4, dysregulated signaling of CXCR4, or pathogenesis mediated by the CXCR4/SDF-1 signaling pathway in a human sensitive to bleeding events, comprising the step of administering a therapeutically effective dose of a BTK inhibitor, or a pharmaceutically-acceptable salt, cocrystal, hydrate, solvate, or prodrug thereof.

In selected embodiments, the invention provides a method of treating a disorder associated with overexpression of CXCR4, dysregulated signaling of CXCR4, or pathogenesis mediated by the CXCR4/SDF-1 signaling pathway in a human sensitive to bleeding events, comprising the step of administering a therapeutically effective dose of a BTK inhibitor, wherein the BTK inhibitor is Formula (II), and wherein the disorder is selected from the group consisting of bladder cancer, squamous cell carcinoma including head and neck cancer, pancreatic ductal adenocarcinoma (PDA), pancreatic cancer, colon carcinoma, mammary carcinoma, breast cancer, fibrosarcoma, mesothelioma, renal cell carcinoma, lung carcinoma, thyoma, prostate cancer, colorectal cancer, ovarian cancer, acute myeloid leukemia, thymus cancer, brain cancer, squamous cell cancer, skin cancer, eye cancer, retinoblastoma, melanoma, intraocular melanoma, oral cavity and oropharyngeal cancers, gastric cancer, stomach cancer, cervical cancer, head, neck, renal cancer, kidney cancer, liver cancer, ovarian cancer, prostate cancer, colorectal cancer, esophageal cancer, testicular cancer, gynecological cancer, thyroid cancer, acquired immune deficiency syndrome (AIDS)-related cancers (e.g., lymphoma and Kaposi's sarcoma), viral-induced cancer, glioblastoma, esophogeal tumors, hematological neoplasms, non-small-cell lung cancer, chronic myelocytic leukemia, diffuse large B-cell lymphoma, esophagus tumor, follicle center lymphoma, head and neck tumor, hepatitis C virus infection, hepatocellular carcinoma, Hodgkin's disease, metastatic colon cancer, multiple myeloma, non-Hodgkin's lymphoma, indolent non-Hogkin's lymphoma, ovary tumor, pancreas tumor, renal cell carcinoma, small-cell lung cancer, stage IV melanoma, chronic lymphocytic leukemia, B-cell acute lymphoblastic leukemia (ALL), mature B-cell ALL, follicular lymphoma, mantle cell lymphoma, and Burkitt's lymphoma.

In selected embodiments, the invention provides a method of treating a disorder associated with overexpression of CXCR4, dysregulated signaling of CXCR4, or pathogenesis mediated by the CXCR4/SDF-1 signaling pathway in a human sensitive to platelet-mediated thrombosis comprising the step of administering a therapeutically effective dose of a BTK inhibitor, wherein the BTK inhibitor is Formula (II), or a pharmaceutically-acceptable salt, cocrystal, hydrate, solvate, or prodrug thereof.

In selected embodiments, the invention provides a method of treating a disorder associated with overexpression of CXCR4, dysregulated signaling of CXCR4, or pathogenesis mediated by the CXCR4/SDF-1 signaling pathway in a human sensitive to platelet-mediated thrombosis, comprising the step of administering a therapeutically effective dose of a BTK inhibitor, or a pharmaceutically-acceptable salt, cocrystal, hydrate, solvate, or prodrug thereof. In a preferred embodiment, the invention provides a method of treating a disorder associated with overexpression of CXCR4, dysregulated signaling of CXCR4, or pathogenesis mediated by the CXCR4/SDF-1 signaling pathway in a human sensitive to platelet-mediated thrombosis, comprising the step of administering a therapeutically effective dose of a BTK inhibitor, wherein the BTK inhibitor is Formula (II), or a pharmaceutically-acceptable salt, cocrystal, hydrate, solvate, or prodrug thereof. In a preferred embodiment, the invention provides a method of treating a disorder associated with overexpression of CXCR4, dysregulated signaling of CXCR4, or pathogenesis mediated by the CXCR4/SDF-1 signaling pathway in a human sensitive to platelet-mediated thrombosis, comprising the step of administering a therapeutically effective dose of a BTK inhibitor, wherein the BTK inhibitor is Formula (II), or a pharmaceutically-acceptable salt, cocrystal, hydrate, solvate, or prodrug thereof, further comprising the step of administering a therapeutically effective dose of an anticoagulant or antiplatelet agent. In a preferred embodiment, the invention provides a method of treating a disorder associated with overexpression of CXCR4, dysregulated signaling of CXCR4, or pathogenesis mediated by the CXCR4/SDF-1 signaling pathway in a human sensitive to platelet-mediated thrombosis, comprising the step of administering a therapeutically effective dose of a BTK inhibitor, wherein the BTK inhibitor is Formula (II), or a pharmaceutically-acceptable salt, cocrystal, hydrate, solvate, or prodrug thereof, further comprising the step of administering a therapeutically effective dose of an anticoagulant or antiplatelet agent.

In a preferred embodiment, the invention provides a method of treating a disorder associated with overexpression of CXCR4, dysregulated signaling of CXCR4, or pathogenesis mediated by the CXCR4/SDF-1 signaling pathway in a human sensitive to platelet-mediated thrombosis, comprising the step of administering a therapeutically effective dose of a BTK inhibitor, wherein the BTK inhibitor is Formula (II), or a pharmaceutically-acceptable salt, cocrystal, hydrate, solvate, or prodrug thereof, further comprising the step of administering a therapeutically effective dose of an anticoagulant or antiplatelet agent, wherein the anticoagulant or antiplatelet agent is selected from the group consisting of clopidogrel, prasugrel, ticagrelor, ticlopidine, warfarin, acenocoumarol, dicumarol, phenprocoumon, heparain, low molecular weight heparin, fondaparinux, and idraparinux.

In a preferred embodiment, the invention provides a method of treating a disorder associated with overexpression of CXCR4, dysregulated signaling of CXCR4, or pathogenesis mediated by the CXCR4/SDF-1 signaling pathway in a human sensitive to platelet-mediated thrombosis, comprising the step of administering a therapeutically effective dose of a BTK inhibitor, or a pharmaceutically-acceptable salt, cocrystal, hydrate, solvate, or prodrug thereof, further comprising the step of administering a therapeutically effective dose of an anticoagulant or antiplatelet agent, wherein the anticoagulant or antiplatelet agent is selected from the group consisting of clopidogrel, prasugrel, ticagrelor, ticlopidine, warfarin, acenocoumarol, dicumarol, phenprocoumon, heparain, low molecular weight heparin, fondaparinux, and idraparinux.

In selected embodiments, the invention provides a method of treating a disorder associated with overexpression of CXCR4, dysregulated signaling of CXCR4, or pathogenesis mediated by the CXCR4/SDF-1 signaling pathway in a human sensitive to platelet-mediated thrombosis, comprising the step of administering a therapeutically effective dose of a BTK inhibitor, wherein the BTK inhibitor is Formula (II), and wherein the disorder is selected from the group consisting of bladder cancer, squamous cell carcinoma including head and neck cancer, pancreatic ductal adenocarcinoma (PDA), pancreatic cancer, colon carcinoma, mammary carcinoma, breast cancer, fibrosarcoma, mesothelioma, renal cell carcinoma, lung carcinoma, thyoma, prostate cancer, colorectal cancer, ovarian cancer, acute myeloid leukemia, thymus cancer, brain cancer, squamous cell cancer, skin cancer, eye cancer, retinoblastoma, melanoma, intraocular melanoma, oral cavity and oropharyngeal cancers, gastric cancer, stomach cancer, cervical cancer, head, neck, renal cancer, kidney cancer, liver cancer, ovarian cancer, prostate cancer, colorectal cancer, esophageal cancer, testicular cancer, gynecological cancer, thyroid cancer, acquired immune deficiency syndrome (AIDS)-related cancers (e.g., lymphoma and Kaposi's sarcoma), viral-induced cancer, glioblastoma, esophogeal tumors, hematological neoplasms, non-small-cell lung cancer, chronic myelocytic leukemia, diffuse large B-cell lymphoma, esophagus tumor, follicle center lymphoma, head and neck tumor, hepatitis C virus infection, hepatocellular carcinoma, Hodgkin's disease, metastatic colon cancer, multiple myeloma, non-Hodgkin's lymphoma, indolent non-Hogkin's lymphoma, ovary tumor, pancreas tumor, renal cell carcinoma, small-cell lung cancer, stage IV melanoma, chronic lymphocytic leukemia, B-cell acute lymphoblastic leukemia (ALL), mature B-cell ALL, follicular lymphoma, mantle cell lymphoma, and Burkitt's lymphoma.

In selected embodiments, the invention provides a method of treating a disorder associated with overexpression of CXCR4, dysregulated signaling of CXCR4, or pathogenesis mediated by the CXCR4/SDF-1 signaling pathway in a human sensitive to platelet-mediated thrombosis, comprising the step of administering a therapeutically effective dose of a BTK inhibitor, wherein the BTK inhibitor is Formula (II), and wherein the disorder is selected from the group consisting of bladder cancer, squamous cell carcinoma including head and neck cancer, pancreatic ductal adenocarcinoma (PDA), pancreatic cancer, colon carcinoma, mammary carcinoma, breast cancer, fibrosarcoma, mesothelioma, renal cell carcinoma, lung carcinoma, thyoma, prostate cancer, colorectal cancer, ovarian cancer, acute myeloid leukemia, thymus cancer, brain cancer, squamous cell cancer, skin cancer, eye cancer, retinoblastoma, melanoma, intraocular melanoma, oral cavity and oropharyngeal cancers, gastric cancer, stomach cancer, cervical cancer, head, neck, renal cancer, kidney cancer, liver cancer, ovarian cancer, prostate cancer, colorectal cancer, esophageal cancer, testicular cancer, gynecological cancer, thyroid cancer, acquired immune deficiency syndrome (AIDS)-related cancers (e.g., lymphoma and Kaposi's sarcoma), viral-induced cancer, glioblastoma, esophogeal tumors, hematological neoplasms, non-small-cell lung cancer, chronic myelocytic leukemia, diffuse large B-cell lymphoma, esophagus tumor, follicle center lymphoma, head and neck tumor, hepatitis C virus infection, hepatocellular carcinoma, Hodgkin's disease, metastatic colon cancer, multiple myeloma, non-Hodgkin's lymphoma, indolent non-Hogkin's lymphoma, ovary tumor, pancreas tumor, renal cell carcinoma, small-cell lung cancer, stage IV melanoma, chronic lymphocytic leukemia, B-cell acute lymphoblastic leukemia (ALL), mature B-cell ALL, follicular lymphoma, mantle cell lymphoma, and Burkitt's lymphoma.

In selected embodiments, the BTK inhibitor and the anticoagulant or the antiplatelet active pharmaceutical ingredient are administered sequentially. In selected embodiments, the BTK inhibitor and the anticoagulant or the antiplatelet active pharmaceutical ingredient are administered concomittently. In selected embodiments, the BTK inhibitor is administered before the anticoagulant or the antiplatelet active pharmaceutical ingredient. In selected embodiments, the BTK inhibitor is administered after the anticoagulant or the antiplatelet active pharmaceutical ingredient.

Selected anti-platelet and anticoagulant active pharmaceutical ingredients for use in the methods of the present invention include, but are not limited to, cyclooxygenase inhibitors (e.g., aspirin), adenosine diphosphate (ADP) receptor inhibitors (e.g., clopidogrel and ticlopidine), phosphodiesterase inhibitors (e.g., cilostazol), glycoprotein IIb/IIIa inhibitors (e.g., abciximab, eptifibatide, and tirofiban), adenosine reuptake inhibitors (e.g., dipyridamole), and acetylsalicylic acid (aspirin). In other embodiments, examples of anti-platelet active pharmaceutical ingredients for use in the methods of the present invention include anagrelide, aspirin/extended-release dipyridamole, cilostazol, clopidogrel, dipyridamole, prasugrel, ticagrelor, ticlopidine, vorapaxar, tirofiban HCl, eptifibatide, abciximab, argatroban, bivalirudin, dalteparin, desirudin, enoxaparin, fondaparinux, heparin, lepirudin, apixaban, dabigatran etexilate mesylate, rivaroxaban, and warfarin.

In an embodiment, the invention includes a method of treating a disorder associated with overexpression of CXCR4 or dysregulated signaling of CXCR4, comprising the step of orally administering, to a human in need thereof, a Bruton's tyrosine kinase (BTK) inhibitor, wherein the BTK inhibitor is (S)-4-(8-amino-3-(1-(but-2-ynoyl)pyrrolidin-2-yl)imidazo[1,5-a]pyrazin-1-yl)-N-(pyridin-2-yl)benzamide or a pharmaceutically acceptable salt, solvate, hydrate, cocrystal, or prodrug thereof, further comprising the step of administering a therapeutically effective dose of an anticoagulant or antiplatelet active pharmaceutical ingredient, wherein the anticoagulant or antiplatelet active pharmaceutical ingredient is selected from the group consisting of acenocoumarol, anagrelide, anagrelide hydrochloride, abciximab, aloxiprin, antithrombin, apixaban, argatroban, aspirin, aspirin with extended-release dipyridamole, beraprost, betrixaban, bivalirudin, carbasalate calcium, cilostazol, clopidogrel, clopidogrel bisulfate, cloricromen, dabigatran etexilate, darexaban, dalteparin, dalteparin sodium, defibrotide, dicumarol, diphenadione, dipyridamole, ditazole, desirudin, edoxaban, enoxaparin, enoxaparin sodium, eptifibatide, fondaparinux, fondaparinux sodium, heparin, heparin sodium, heparin calcium, idraparinux, idraparinux sodium, iloprost, indobufen, lepirudin, low molecular weight heparin, melagatran, nadroparin, otamixaban, parnaparin, phenindione, phenprocoumon, prasugrel, picotamide, prostacyclin, ramatroban, reviparin, rivaroxaban, sulodexide, terutroban, terutroban sodium, ticagrelor, ticlopidine, ticlopidine hydrochloride, tinzaparin, tinzaparin sodium, tirofiban, tirofiban hydrochloride, treprostinil, treprostinil sodium, triflusal, vorapaxar, warfarin, warfarin sodium, ximelagatran, salts thereof, solvates thereof, hydrates thereof, and combinations thereof.

In selected embodiments, the invention provides a method of treating a disorder associated with overexpression of CXCR4, dysregulated signaling of CXCR4, or pathogenesis mediated by the CXCR4/SDF-1 signaling pathway in a human with a history of thrombosis, comprising the step of administering a therapeutically effective dose of a BTK inhibitor, or a pharmaceutically-acceptable salt, cocrystal, hydrate, solvate, or prodrug thereof. In selected embodiments, the invention provides a method of treating a disorder associated with overexpression of CXCR4, dysregulated signaling of CXCR4, or pathogenesis mediated by the CXCR4/SDF-1 signaling pathway in a human sensitive to platelet-mediated thrombosis, method of treating a cancer in a human with a history of thrombosis, comprising the step of administering a therapeutically effective dose of a BTK inhibitor, wherein the BTK inhibitor is a compound of Formula (II) or a pharmaceutically-acceptable salt, cocrystal, hydrate, solvate, or prodrug thereof. In selected embodiments, the invention provides a method of treating a disorder associated with overexpression of CXCR4, dysregulated signaling of CXCR4, or pathogenesis mediated by the CXCR4/SDF-1 signaling pathway in a human sensitive to platelet-mediated thrombosis, method of treating a cancer in a human with a history of thrombosis, comprising the step of administering a therapeutically effective dose of a BTK inhibitor, wherein the BTK inhibitor is a compound of Formula (XXVIII) or a pharmaceutically-acceptable salt, cocrystal, hydrate, solvate, or prodrug thereof.

In selected embodiments, the BTK inhibitor and the anticoagulant or the antiplatelet agent are administered sequentially. In selected embodiments, the BTK inhibitor and the anticoagulant or the antiplatelet agent are administered concomittently. In selected embodiments, the BTK inhibitor is administered before the anticoagulant or the antiplatelet agent. In selected embodiments, the BTK inhibitor is administered after the anticoagulant or the antiplatelet agent.

Preferred anti-platelet and anticoagulant agents for use in the methods of the present invention include, but are not limited to, cyclooxygenase inhibitors (e.g., aspirin), adenosine diphosphate (ADP) receptor inhibitors (e.g., clopidogrel and ticlopidine), phosphodiesterase inhibitors (e.g., cilostazol), glycoprotein IIb/IIIa inhibitors (e.g., abciximab, eptifibatide, and tirofiban), adenosine reuptake inhibitors (e.g., dipyridamole), and acetylsalicylic acid (aspirin). In other embodiments, examples of anti-platelet agents for use in the methods of the present invention include anagrelide, aspirin/extended-release dipyridamole, cilostazol, clopidogrel, dipyridamole, prasugrel, ticagrelor, ticlopidine, vorapaxar, tirofiban HCl, eptifibatide, abciximab, argatroban, bivalirudin, dalteparin, desirudin, enoxaparin, fondaparinux, heparin, lepirudin, apixaban, dabigatran etexilate mesylate, rivaroxaban, and warfarin.

EXAMPLES

The embodiments encompassed herein are now described with reference to the following examples. These examples are provided for the purpose of illustration only and the disclosure encompassed herein should in no way be construed as being limited to these examples, but rather should be construed to encompass any and all variations which become evident as a result of the teachings provided herein.

Example 1—Materials and Methods

Recombinant Human SDF-1 can be Purchased from ProSpec (East Brunswick, N.J.).

Antibodies: All phospho-specific antibodies can be purchased from BD BioScience (San Jose, Calif.) or Cell Signaling Technology (Danvers, Mass.). Mouse monoclonal antibody R-phycoerythrin-conjugated anti-human CXCR4 antibody (clone 12G5) is available from R&D Systems (Minneapolis, Minn.).

Table 2 shows phospho-specific antibodies. Each antibody is conjugated to either Alexa-488 or Alexa 647 fluorophores.

TABLE 2

| Phospho-specific antibodies. |
| --- |
| p-AKT (S473) |
| p-ERK1/2 (Thr202/Tyr204) |
| p-S6 Ribosomal Protein (Ser235/236) |
| p-GSK-3β (Ser9) |
| p-BTK (pY551) |
| p-CREB (pS133)/ATF-1 (pS63) |
| p-p38 MAPK (Thr180/Tyr182) |
| p-NF-κB p65 (Ser536) |
| PLC-γ2 (pY759) |

Cells: SJSA-1 (osteosarcoma), U-937 (leukemia), MOLM13 (leukemia), T24 (bladder cancer), and PC3 (prostate cancer) cell lines can be purchased through ATCC (Manassas, Va.).

Mice: Female BALB/c mice (6 to 8 weeks old) can be purchased from The Jackson Laboratory (Bar Harbor, Me.).

Example 2—CXCR4-SDF1 Phosphoflow Assay

The blocking potential of an agent to inhibit BTK activity is tested using a CXCR4-SDF1 assay. Cancer cells that express high levels of CXCR4 (e.g., SJSA-1 (osteosarcoma), U-973 (leukemia), MOLM13 (leukemia), T24 (bladder cancer), and PC3 (prostate cancer)) are stimulated with approximately 20 ng/ml CXCL12/SDF-1 for 0, 2, 5, 10 or 20 min in the absence and presence of the agent. A separate control sample is incubated with a BTK inhibitor (e.g., ASTX-1304). The signaling reaction is stopped by the addition of 2% paraformaldehyde fixative for 10 minutes at 37° C.

Cells are permeabilized with ice-cold 90% methanol for 1 hour on ice, and the supernatant removed by centrifugation for 5 minutes at 300×G. Permeabilized cells are resuspended with a PBS 1% BSA solution.

The cells are fixed cells in a staining cocktail that includes cell surface (anti-CXCR4 antibody) and phospho-specific antibodies (Table 2) conjugated to specific fluorescent dyes, and mean fluorescence intensity (MFI) obtained by flow cytometric analysis. MFI values are compared across the stimulation time course to calculate a fold-change based from the basal state MFI value (0 minute time point). Any fold change values >1.5 for a specific phospho-protein readout will be regarded as a positive signaling result.

The results show the signaling nodes activated by SDF-1 at the particular time points in each cancer cell line. Here, the importance of BTK activity on the CXCR4/SDF-1 driven signaling network in each CXCR4+ cancer cell line is investigated by including ASTX-1304, or other specific BTK inhibitors, across a range of concentrations. In addition, other specific kinase inhibitors, such as GDC-0941 (PI3K inhibitor), are tested separately and compared to the results using ASTX-1304. Additionally, the CXCR4 inhibitor, plerixafor, is included as a control for total blockade of SDF-1 induced signaling.

Example 3—Chemotaxis Studies

The invasion potential of cell lines that express high levels of CXCR4 (e.g., SJSA-1 (osteosarcoma), U-973 (leukemia), MOLM13 (leukemia), T24 (bladder cancer), and PC3 (prostate cancer)) is evaluated using Transwell chambers (1 cm² per well, Costar, Bodenheim Germany). The upper and lower culture are separated by an 8 µm pore-size polyvinylpyrrolidone-free polycarbonate filters (Nucleopore, Corning Costar Corp., Cambridge, Mass.). Briefly, the lower compartment of the chamber is loaded with aliquots of serum-free medium plus rhSDF-1 (100 ng/mL). Before the invasion assay, filters are coated with 100 µg/well Matrigel (Becton Dickinson) diluted in culture medium. Tumor cells are seeded onto the reconstituted basement for 24 hours ($5 \times 10^4$ cells per well) at 37° C. in humidified atmosphere with 5% $CO_2$. Cells that pass the synthetic basement are fixed with ethanol and stained with Giemsa solution (Diff-Quik kit, Baxter Diagnostics, Milan, Italy). Each experiment is performed in triplicate. Cells migrated to the underside of the filter are counted in five fields (magnification ×100) in each well by light microscopy. The effect of BTK inhibition on abating invasion is assessed by preincubating (≥30 minutes) the tumor cells with increasing concentrations (10 nM, 100 nM, and 1 µM) of ASTX-1304, or other BTK inhibitors, before seeding them onto the reconstituted basement. Results are expressed as the percentage of migrated cells.

Example 4—Adhesion Assays

Cancer cells (described above) are grown in 100 cc tissue culture plates and treated with increasing concentrations (10 nM, 100 nM, and 1 µM) of ASTX-1304, or other BTK inhibitors, or left untreated overnight. 8-strip wells coated with fibronectin, vitronectin, laminin, collagen type I or collagen type IV (Chemicon, Temecula, Calif.) is hydrated with 200 µl of PBS for 15 min. Cells are harvested by the addition of Cellstripper (Mediatech, Herndon, Va.) solution for 10 min. ASTX-1304 (or other BTK inhibitor)-treated and untreated cells are centrifuged and resuspended in media to a final concentration of 500,000 cells/ml. After removal of the PBS from the coated 8-well strips, 50,000 cells in a volume of 100 µl are added to each well, incubated for 1 h at 37° C. in a tissue culture incubator and the media removed. The wells are washed twice with PBS containing calcium and magnesium. 100 µl of crystal violet solution (0.2% dissolved in 10% ethanol) is added and incubated for 5 min at room temperature. The wells are washed three times gently with PBS containing calcium and magnesium and 100 µl of solubilization buffer is added (50% $NaH_2PO_4$ 0.1 M pH 4.5 and 50% ethanol). The absorbance is measured at 560 nm using a VERSAmax tunable microplate reader (Molecular Devices). Results are presented as optical density following crystal violet staining of cells that remained adherent to the plate.

Example 5—In Vivo Metastasis Study

To investigate the involvement of the CXCR4/SDF-1 axis during osteosarcoma metastatic process in vivo, one group (N=5) of BALB/c mice is given an injection of $10^6$ SJSA cells alone into the tail vein and another group (N=5) of mice is given an injection of SJSA cells and ASTX-1304 or other BTK inhibitors (25 mg/kg). The mice are given intravenous injections of ASTX-1304 once daily at the same concentration.

All mice are sacrificed 5 weeks after injection and lungs examined macroscopically and microscopically for the presence of metastases. For histology and immunohistochemistry evaluation, lungs are collected and fixed in 10% formalin and embedded in paraffin. Sections of 4 µm thickness will be stained with H&E for conventional histology.

Example 6—Kinome Screen

The preclinical selectivity and potency characteristics of the BTK inhibitor of Formula (II) were compared to BTK inhibitor ibrutinib (Formula (V)). In Table 3, a kinome screen (performed by Life Technologies or based on literature data) is shown that compares these compounds.

TABLE 3

Kinome Screen for BTK Inhibitors ($IC_{50}$, nM)

| 3F-Cys Kinase | Formula (II) | Ibrutinib (Formula (V)) |
| --- | --- | --- |
| Btk | 3.1 | 0.5 |
| Tec | 29 | 78 |
| Bmx | 39 | 0.80 |
| Itk | >1000 | 10.7 |
| Txk | 291 | 2.0 |
| EGFR | >1000 | 5.6 |
| ErbB2 | 912 | 9.4 |
| ErbB4 | 13.2 | 2.7 |
| Blk | >1000 | 0.5 |
| JAK-3 | >1000 | 16.1 |

The results shown in Table 3 are obtained from a 10 point biochemical assay generated from 10 point concentration curves.

Example 7—CXCR-4/SDF-1 Signaling Inhibition and CXCR-4 Surface Expression

Figure 2:
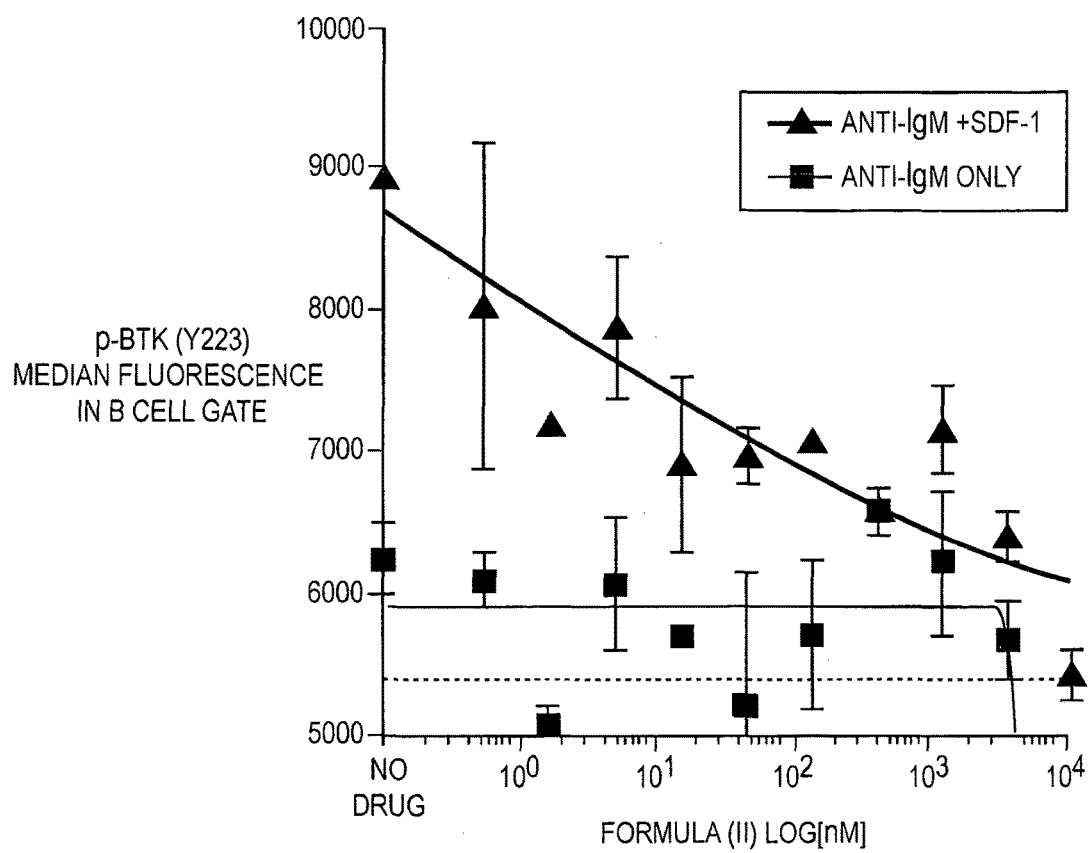
FIG. 2 illustrates $CD14^+$ monocyte cell fluorescence, showing that CXCR-4/SDF-1 signaling is inhibited by the BTK inhibitor of Formula (II).

Healthy PBMCs were incubated with and without Formula (II) at the shown concentrations for 2 hours and then stimulated with anti-IgM [10 ug/mL] or anti-IgM+SDF-1 [50 ng/mL] for 5 minutes at 37° C. Cells were then analyzed by phosphoflow cytometry and p-Btk(Y223) was measured in the CD20+ B cell gate and the $CD14^+$ monocyte gate separately. Results are shown in FIG. 1 and FIG. 2. In B cells, BTK phosphorylation in anti-IgM stimulated B cells is increased with the addition of SDF-1 (CXCL-12) in the "No drug" condition. The BTK phosphorylation is inhibited by the BTK inhibitor Formula (II) at low nM concentrations in both stimulation conditions. In monocytes, BTK phosphorylation is only observed when SDF-1 is present. Formula (II) at low nM concentrations in both stimulation conditions.

Figure 3:
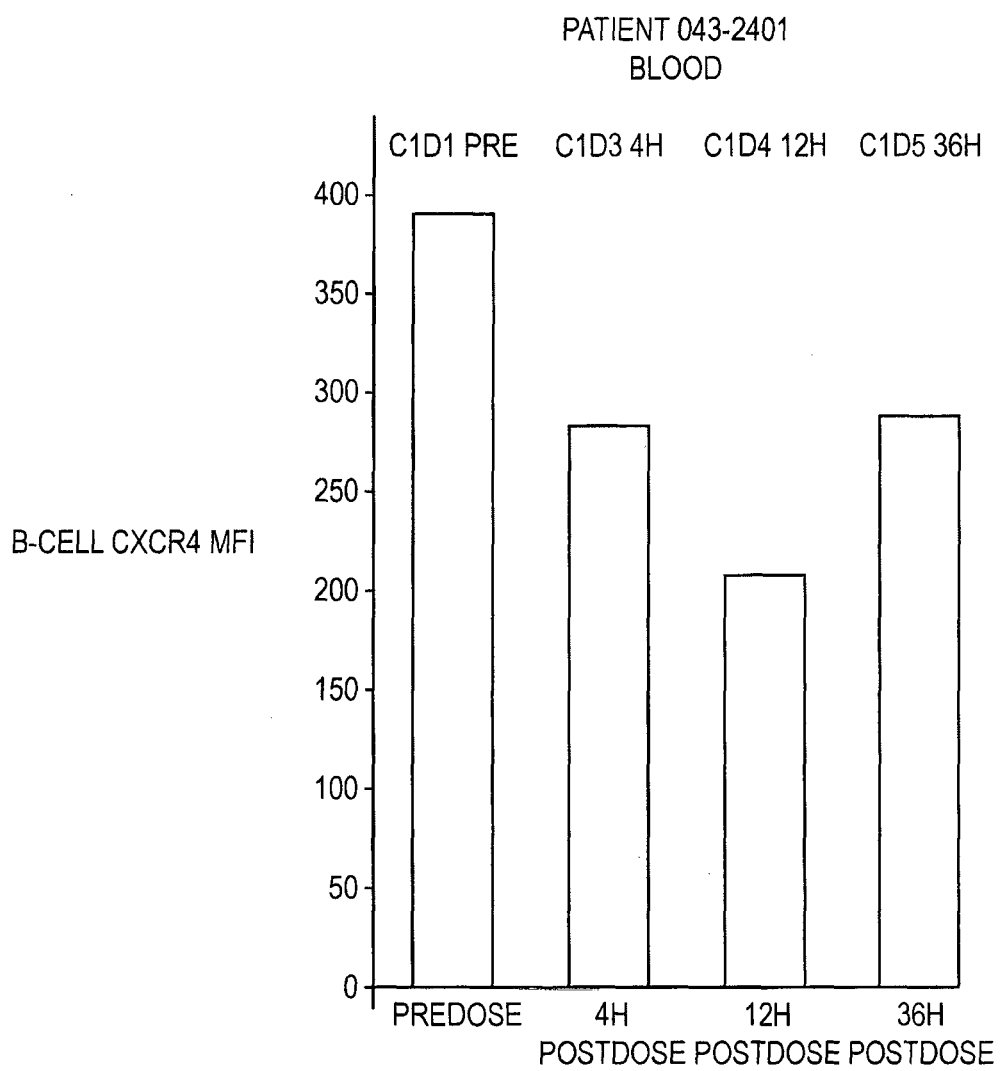
FIG. 3 illustrates CXCR4 surface expression in B-CLL (B cell chronic lymphocytic leukemia) following administration of the BTK inhibitor of Formula (II).
Figure 4:
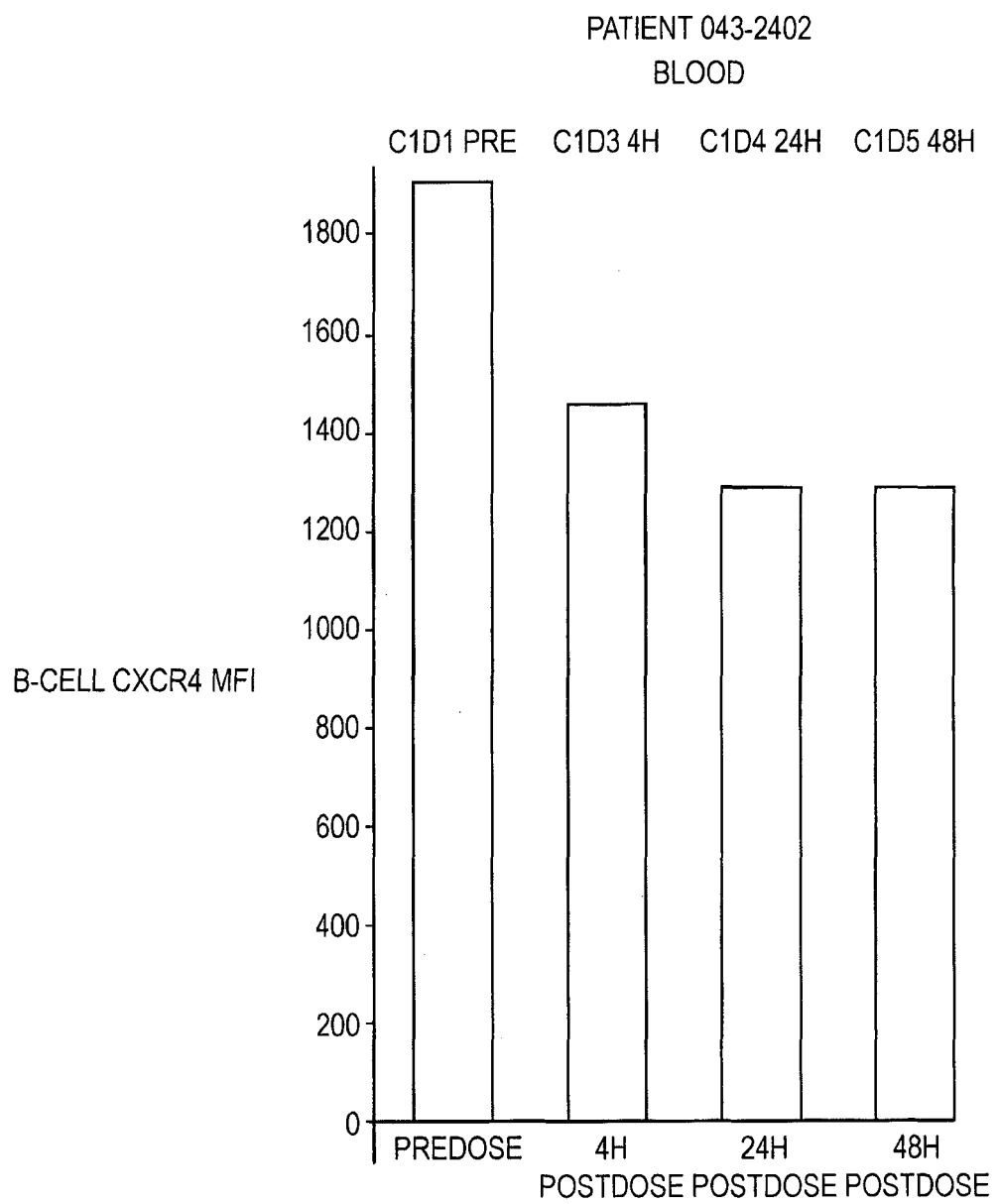
FIG. 4 illustrates CXCR4 surface expression in B-CLL following administration of the BTK inhibitor of Formula (II).

FIG. 3 and FIG. 4 show that CXCR4 surface expression is decreased in B-CLL (B cell chronic lymphocytic leukemia) following administration of the BTK inhibitor of Formula (II). CLL patients with the 17p deletion were administered Formula (II) at 100 mg BID (FIG. 3) and 200 mg QD (FIG. 4). Drug was given for 3 days. Blood was drawn predose, and then 4, 24, and 48 hours after the day 3 dose. The results show that in B-CLL cells, CXCR4 surface expression in samples after Formula (II) administration is reduced compared to the predose levels.

Figure 5:
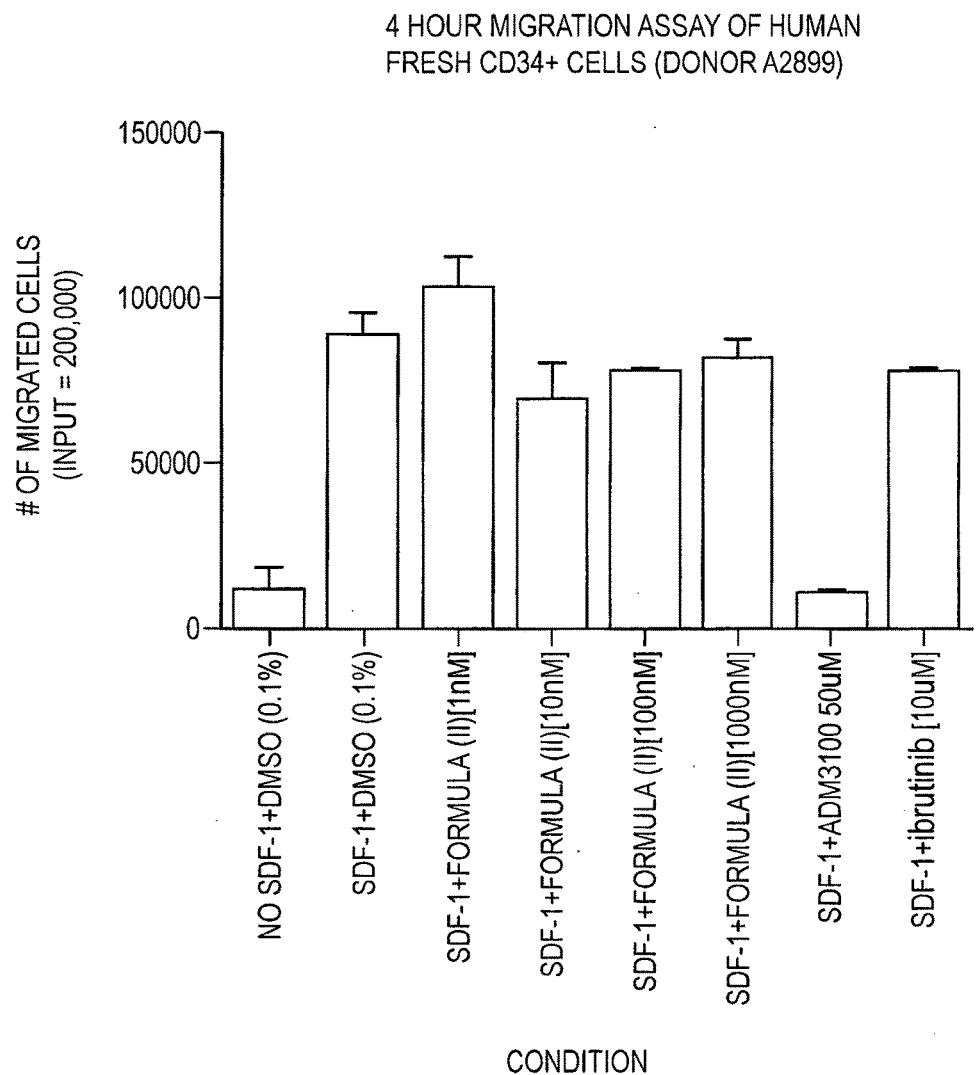
FIG. 5 illustrates that BTK inhibition is not impacting the ability of $CD34^+$ cells to migrate towards SDF-1 (CXCL-12) in fresh $CD34^+$ cells.
Figure 6:
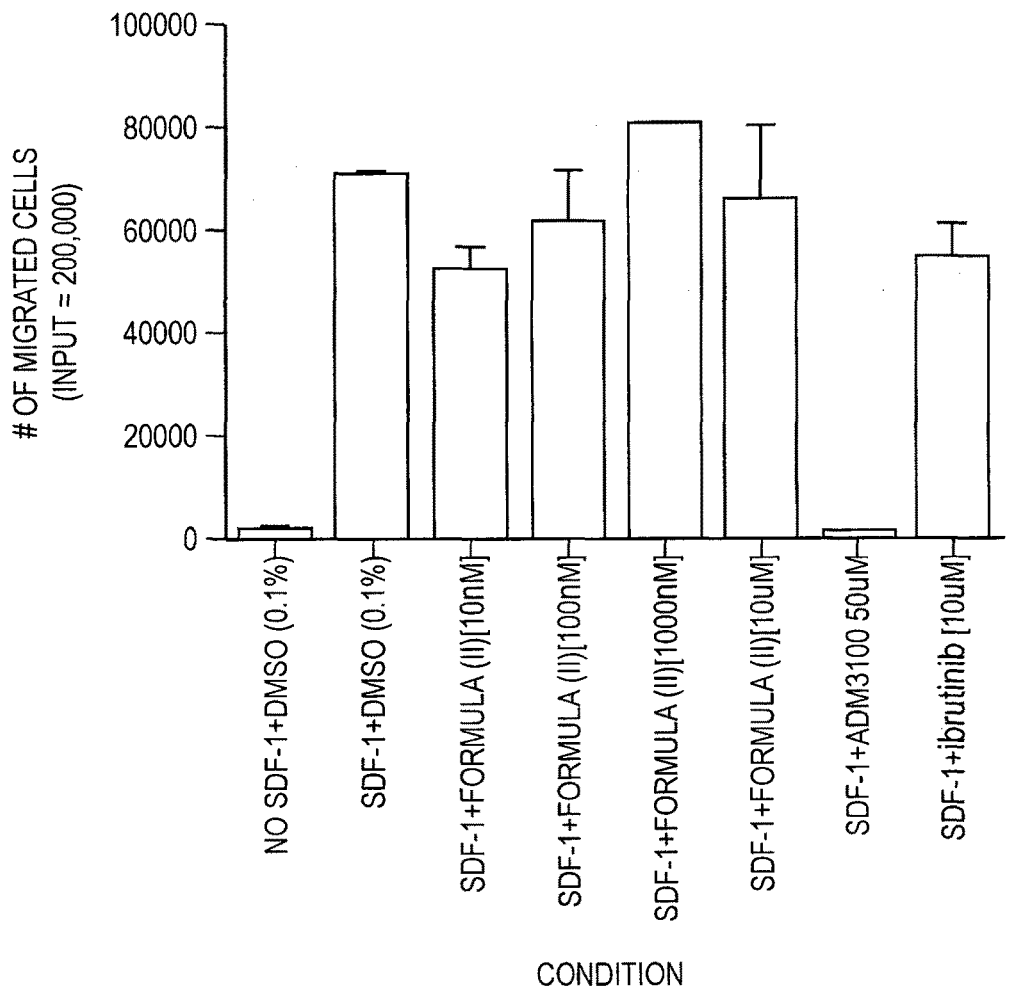
FIG. 6 illustrates that BTK inhibition is not impacting the ability of $CD34^+$ cells to migrate towards SDF-1 (CXCL-12) in cryopreserved $CD34^+$ cells.

FIG. 5 and FIG. 6 illustrate that BTK inhibition is not impacting the ability of $CD34^+$ cells to migrate towards SDF-1 (CXCL-12) in both fresh and cryopreserved $CD34^+$ cells.

Figure 7:
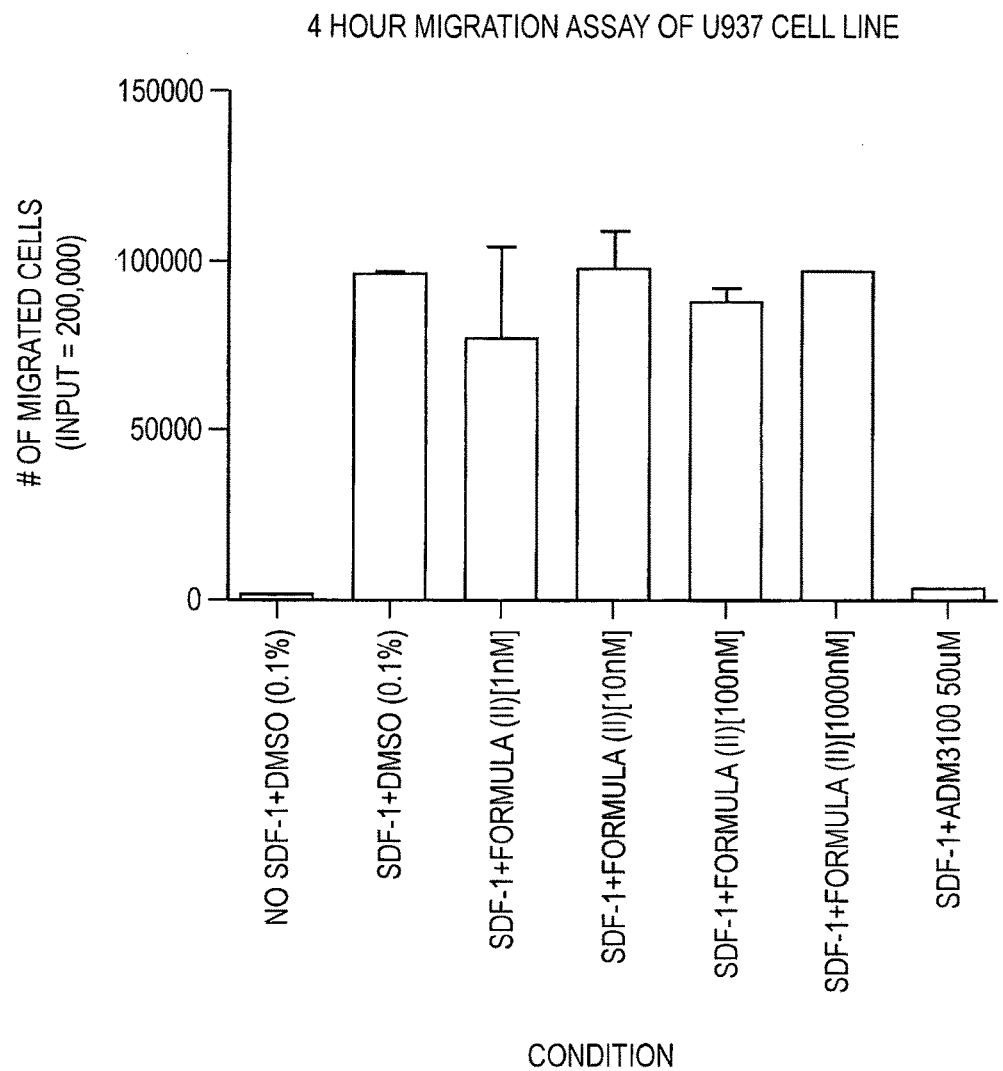
FIG. 7 illustrates that BTK inhibition is not impacting the ability of U937 cells to migrate towards SDF-1 (CXCL-12).

FIG. 7 illustrates that BTK inhibition is not impacting the ability of U937 cells to migrate towards SDF-1 (CXCL-12).

Figure 8:
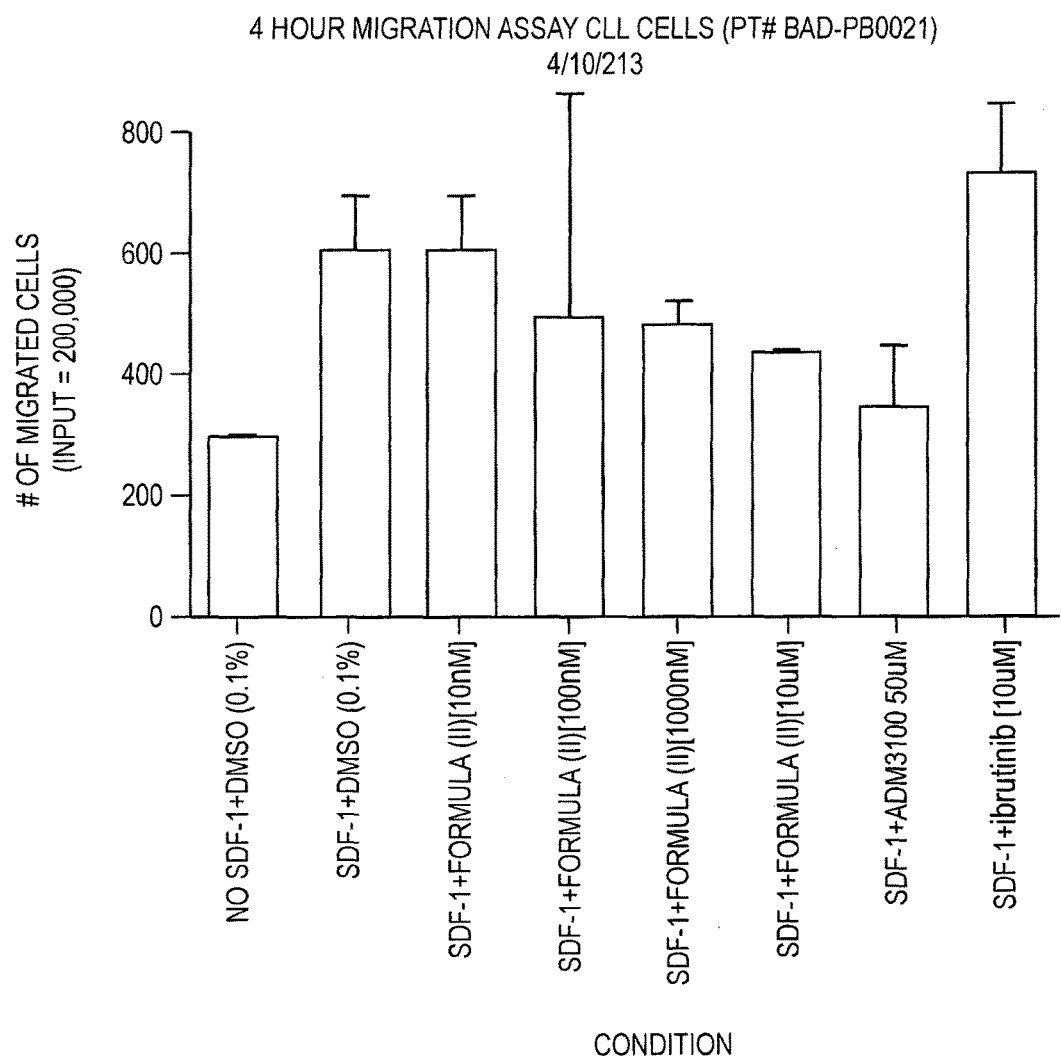
FIG. 8 illustrates that BTK inhibition is not impacting the ability of CLL cells to migrate towards SDF-1 (CXCL-12).

FIG. 8 illustrates that BTK inhibition is not impacting the ability of CLL cells to migrate towards SDF-1 (CXCL-12).

Figure 9:
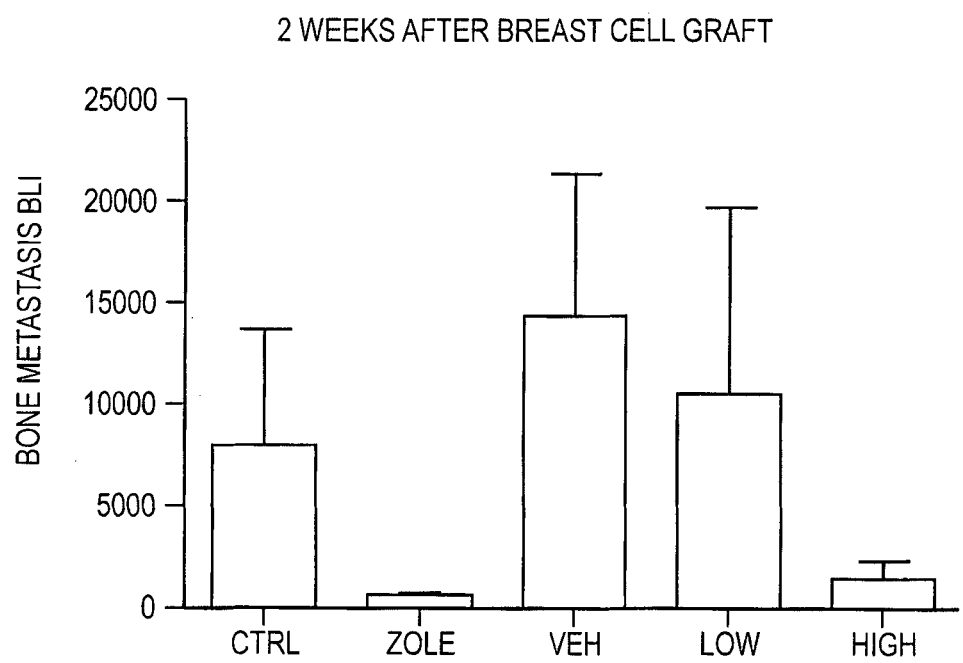
FIG. 9 illustrates the results of a RANK MDA-MB231 mouse experiment.

FIG. 9 illustrates the results of a RANK MDA-MB231 mouse experiment. The design of the study is as follows: regular water—control (N=5); 0 mg/kg/day (vehicle) Formula (II) peroral (PO) (N=5); ~10 mg/kg/day Formula (II) PO (N=5); ~50 mg/kg/day Formula (II) PO (N=5); 0.54 mg/kg zoledronate IV (N=5) [single dose]. The primary endpoint was bioluminescence imaging (weekly). The secondary endpoints were serum CTx (bone resorption) and serum P1NP (bone formation). The results show that Formula (II) exhibits dose-response reduction in bone metastases at 2 weeks of treatment, and also show that Formula (II) prevents metastasis by inhibiting the CXCR4/SDF1 axis.

SDF-1 binds to CXCR4 and amplifies B cell receptor-induced BTK phosphorylation. The contribution of SDF-1 in amplifying the BTK pathway in B cells may contribute to a prosurvival phenotype. This may be especially important in the anti-apoptotic phenotype of malignant cells (i.e., CLL B cells). BTK inhibition by Formula (II) inhibits the SDF-1/CXCR4 signaling in B cells.

Monocytes also express CXCR4 and express BTK. SDF-1 induced p-Btk can be measured by phosphoflow cytometry. Like in B cells, BTK inhibition by Formula (II) inhibits the SDF-1/CXCR4 signaling in monocytes.

BTK inhibition, by itself, does not appear to inhibit in vitro cell migration towards SDF-1, suggesting that non-BTK pathways may be more relevant for cell migration. However, BTK inhibition over a period of days results in decreased expression of CXCR4 in some patients, which would likely limit the migration potential towards SDF-1 and possibly the prosurvival signals as well.

We claim:

1. A method of treating nephropathy in a human subject having overexpression of CXCR4, comprising (i) measuring CXCR-4 expression in a tissue sample isolated from the human subject, and (ii) administering to the human subject a pharmaceutical composition comprising an amount of a compound of the formula:

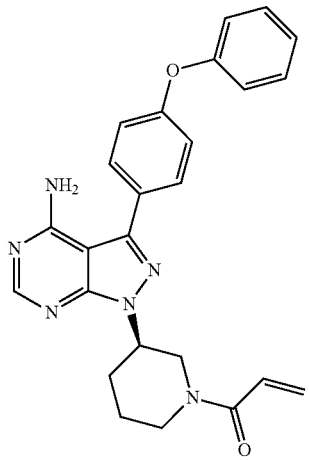 [SMILES: C=CC(=O)N1CCC[C@@H](n2nc(-c3ccc(Oc4ccccc4)cc3)c3c(N)ncnc32)C1]

or a pharmaceutically acceptable salt thereof effective to reduce expression of CXCR-4.

2. The method of claim 1, wherein the nephropathy is IgA nephropathy.

3. The method of claim 1, wherein the nephropathy is membranous nephropathy.

4. The method of claim 1, wherein the measuring CXCR-4 expression is done before administration of the pharmaceutical composition.

5. The method of claim 1, wherein the measuring CXCR-4 expression is done after administration of the composition.

6. The method of claim 4 or 5, wherein the CXCR-4 expression is measured on peripheral blood mononuclear cells isolated from the blood of the human subject.

7. The method of claim 1, wherein the pharmaceutical composition is administered orally.

8. The method of claim 7, wherein the pharmaceutical composition is formulated as a capsule.

9. The method of claim 8, wherein the capsule is a gelatin capsule.

10. The method of claim 8, wherein the capsule contains about 140 mg of the compound.

11. The method of claim 1, wherein the amount of the compound effective to reduce CXCR-4 expression is about 1 mg to about 500 mg daily.

12. The method of claim 1, wherein the amount of the compound effective to reduce CXCR-4 expression is about 10 mg to about 300 mg daily.

13. The method of claim 1, wherein the amount of the compound effective to reduce CXCR-4 expression is about 20 mg to about 250 mg daily.

14. The method of claim 1, wherein the amount of the compound effective to reduce CXCR-4 expression is about 10 mg to about 200 mg daily.

15. The method of claim 1, wherein the amount of the compound effective to reduce CXCR-4 expression is about 20 mg to about 150 mg daily.

16. The method of claim 1, wherein the pharmaceutical composition comprises a compound of the formula:

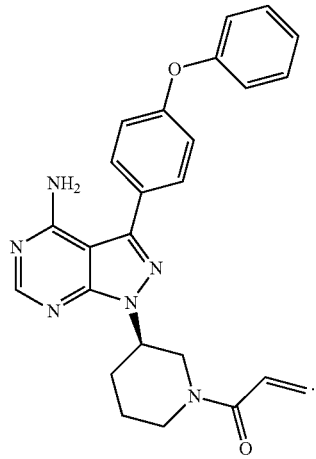 [SMILES: C=CC(=O)N1CCC[C@@H](n2nc(-c3ccc(Oc4ccccc4)cc3)c3c(N)ncnc32)C1]

17. The method of claim 1, wherein the pharmaceutical composition comprises a pharmaceutically acceptable salt of the compound of the formula:

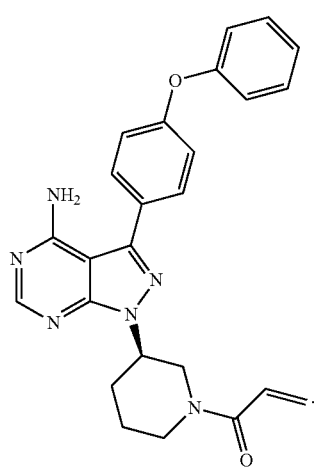 [SMILES: C=CC(=O)N1CCC[C@@H](n2nc(-c3ccc(Oc4ccccc4)cc3)c3c(N)ncnc32)C1]

* * * * *